(12) United States Patent
Bergmann et al.

(10) Patent No.: US 12,270,075 B2
(45) Date of Patent: Apr. 8, 2025

(54) TAGGED NUCLEOSIDE COMPOUNDS USEFUL FOR NANOPORE DETECTION

(71) Applicant: Roche Sequencing Solutions, Inc., Pleasanton, CA (US)

(72) Inventors: Frank Bergmann, Iffeldorf (DE); Peter J. Crisalli, Mountain View, CA (US); Sara Kelley, Pleasant Hill, CA (US); Omid Khakshoor, Lathrop, CA (US); Hannes Kuchelmeister, Munich (DE); Meng Taing, Hayward, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 1173 days.

(21) Appl. No.: 16/947,960

(22) Filed: Aug. 25, 2020

(65) Prior Publication Data
US 2020/0385803 A1    Dec. 10, 2020

Related U.S. Application Data

(63) Continuation of application No. PCT/EP2019/054791, filed on Feb. 27, 2019.

(60) Provisional application No. 62/773,995, filed on Nov. 30, 2018, provisional application No. 62/636,807, filed on Feb. 28, 2018.

(51) Int. Cl.
*C07H 19/00* (2006.01)
*C07H 21/00* (2006.01)
*C12Q 1/6869* (2018.01)
*C12Q 1/6874* (2018.01)

(52) U.S. Cl.
CPC ........... *C12Q 1/6874* (2013.01); *C07H 19/00* (2013.01); *C07H 21/00* (2013.01); *C12Q 1/6869* (2013.01)

(58) Field of Classification Search
None
See application file for complete search history.

(56) References Cited

U.S. PATENT DOCUMENTS

| 10,669,580 B2* | 6/2020 | Gremyachinskiy .. C12Q 1/6869 |
| 2013/0244340 A1 | 9/2013 | Davis et al. |
| 2013/0264207 A1 | 10/2013 | Ju et al. |
| 2014/0134616 A1 | 5/2014 | Davis et al. |

FOREIGN PATENT DOCUMENTS

| WO | 2013/154999 A2 | 10/2013 |
| WO | 2013191793 A1 | 12/2013 |
| WO | 2015/148402 A1 | 10/2015 |
| WO | 2016154215 A1 | 9/2016 |

OTHER PUBLICATIONS

Fuller et al., PNAS, 2016, pp. 5233-5238, vol. 113, No. 19. (Year: 2016).*
Fuller, C. et al, Real-time single-molecule electronic DNA sequencing by synthesis using polymer-tagged nucleotides on a nanopore array, PNAS, (2016), pp. 5233-5238, vol. 113, No. 19.
International Search Report and Written Opinion mailed Apr. 11, 2019 in connection with PCT/EP2019/054791 filed Feb. 27, 2019, 14 pages.
Kumar et al, PEG-Labeled Nucleotides and Nanopore Detection for Single Molecule DNA Sequencing by Synthesis, Scientific Reports, 2012, pp. 1-8, vol. 2.
Robertson et al, Single-molecular mass spectrometry in solution using a solitary nanopore, PNAS USA, May 15, 2007, pp. 8207-8211, vol. 104, No. 20.

* cited by examiner

*Primary Examiner* — Traviss C McIntosh, III
(74) *Attorney, Agent, or Firm* — FisherBroyles, LLP; Jason M. Pass; Adam K. Whiting

(57) ABSTRACT

The disclosure relates to tagged nucleoside compounds comprising a nucleotide polyphosphate covalently attached to a tag, wherein the compound is a polymerase substrate and the polymer moiety is capable of entering a nanopore linked to the polymerase and thereby altering the flow of ions through the nanopore. The disclosure also provides methods for preparing the tagged nucleoside compounds and for their use as tags in nanopore-based nucleic acid detection and sequencing.

26 Claims, 3 Drawing Sheets

Specification includes a Sequence Listing.

pUC19 Dumbbell DNA Template of SEQ ID NO:33
CAGTCAGTAGAGAGAGAGATCCTCTAGAGTCGACCTGCAGGCATGCAAGCTTGGCGTAATCATGGTCATAGCTGTTTCCTG
TGTGAAATTGTTATCCGCTCACAATTCCACACAACATACGAGCCGGAAGCATAAAGTGTAAAGCCTGGGGTGCCTAATGAG
TGAGCTAACTCACATTAATTGCGTTGCGCTCACTGCCCGCTTTCCAGTCGGGAAACCTGTCGTGCCAGCTGCATTAATGAA
TCGGCCAACGCGCGGGGAGAGGCGGTTTGCGTATTGGGCGCTCTTCCGCTTCCTCGCTCACTGACTCGCTGCGCTCGGTCG
TTCGGCTGCGGCGAGCGGTATCAGCTCACTCAAAGGCGGTAATACGGTTATCCACAGAATCAGGGGATAACGCAGGAAAGA
ACATGTGAGCAAAAGGCCAGCAAAAGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGACTATAAAGATACCAGGCGTTTCCCC
CTGGAAGCTCCCTCGTGCGCTCTCCTGTTCCGACCCTGCCGCTTACCGGATACCTGTCCGCCTTTCTCCCTTCGGGAAGCG
TGGCGCTTTCTCATAGCTCACGCTGTAGGTATCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAGTCCAACCCGGTAAGACACGACTTATCGCCAC
TGGCAGCAGCCACTGGTAACAGGATTAGCAGAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAAAACTCACGTTAAGGGATTTTGGTCATGAGAT
TATCAAAAAGGATCTTCACCTAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTCGTTCATCCATAGTTGCCTGAC
TCCCCGTCGTGTAGATAACTACGATACGGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCAGAAGTGGTCCTGCAACTTTATCCGCCT
CCATCCAGTCTATTAATTGTTGCCGGGAAGCTAGAGTAAGTAGTTCGCCAGTTAATAGTTTGCGCAACGTTGTTGCCATTG
CTACAGGCATCGTGGTGTCACGCTCGTCGTTTGGTATGGCTTCATTCAGCTCCGGTTCCCAACGATCAAGGCGAGTTACAT
GATCCCCCATGTTGTGCAAAAAAGCGGTTAGCTCCTTCGGTCCTCCGATCGTTGTCAGAAGTAAGTTGGCCGCAGTGTTAT
CACTCATGGTTATGGCAGCACTGCATAATTCTCTTACTGTCATGCCATCCGTAAGATGCTTTTCTGTGACTGGTGAGTACT
CAACCAAGTCATTCTGAGAATAGTGTATGCGGCGACCGAGTTGCTCTTGCCCGGCGTCAATACGGGATAATACCGCGCCAC
ATAGCAGAACTTTAAAAGTGCTCATCATTGGAAAACGTTCTTCGGGGCGAAAACTCTCAAGGATCTTACCGCTGTTGAGAT
CCAGTTCGATGTAACCCACTCGTGCACCCAACTGATCTTCAGCATCTTTTACTTTCACCAGCGTTTCTGGGTGAGCAAAAA
CAGGAAGGCAAAATGCCGCAAAAAAGGGAATAAGGGCGACACGGAAATGTTGAATACTCATACTCTTCCTTTTTCAATATT
ATTGAAGCATTTATCAGGGTTATTGTCTCATGAGCGGATACATATTTGAATGTATTTAGAAAAATAAACAAATAGGGGTTC
CGCGCACATTTCCCCGAAAAGTGCCACCTGACGTCTAAGAAACCATTATTATCATGACATTAACCTATAAAAATAGGCGTA
TCACGAGGCCCTTTCGTCTCGCGCGTTTCGGTGATGACGGTGAAAACCTCTGACACATGCAGCTCCCGGAGACGGTCACAG
CTTGTCTGTAAGCGGATGCCGGGAGCAGACAAGCCCGTCAGGGCGCGTCAGCGGGTGTTGGCGGGTGTCGGGGCTGGCTTA
ACTATGCGGCATCAGAGCAGATTGTACTGAGAGTGCACCATATGCGGTGTGAAATACCGCACAGATGCGTAAGGAGAAAAT
ACCGCATCAGGCGCCATTCGCCATTCAGGCTGCGCAACTGTTGGGAAGGGCGATCGGTGCGGGCCTCTTCGCTATTACGCC
AGCTGGCGAAAGGGGGATGTGCTGCAAGGCGATTAAGTTGGGTAACGCCAGGGTTTTCCCAGTCACGACGTTGTAAAACGA
CGGCCAGTGAATTCGAGCTCGGTACCCGGGGATCTCTCTCTCAAAAACGGAGGAGGAGGACAGTCAGTAGAGAGAGAGATC
CCCGGGTACCGAGCTCGAATTCACTGGCCGTCGTTTTACAACGTCGTGACTGGGAAAACCCTGGCGTTACCCAACTTAATC
GCCTTGCAGCACATCCCCCTTTCGCCAGCTGGCGTAATAGCGAAGAGGCCCGCACCGATCGCCCTTCCCAACAGTTGCGCA
GCCTGAATGGCGAATGGCGCCTGATGCGGTATTTTCTCCTTACGCATCTGTGCGGTATTTCACACCGCATATGGTGCACTC
TCAGTACAATCTGCTCTGATGCCGCATAGTTAAGCCAGCCCCGACACCCGCCAACACCCGCTGACGCGCCCTGACGGGCTT
GTCTGCTCCCGGCATCCGCTTACAGACAAGCTGTGACCGTCTCCGGGAGCTGCATGTGTCAGAGGTTTTCACCGTCATCAC
CGAAACGCGCGAGACGAAAGGGCCTCGTGATACGCCTATTTTTATAGGTTAATGTCATGATAATAATGGTTTCTTAGACGT
CAGGTGGCACTTTTCGGGGAAATGTGCGCGGAACCCCTATTTGTTTATTTTTCTAAATACATTCAAATATGTATCCGCTCA
TGAGACAATAACCCTGATAAATGCTTCAATAATATTGAAAAAGGAAGAGTATGAGTATTCAACATTTCCGTGTCGCCCTTA
TTCCCTTTTTTGCGGCATTTTGCCTTCCTGTTTTTGCTCACCCAGAAACGCTGGTGAAAGTAAAAGATGCTGAAGATCAGT
TGGGTGCACGAGTGGGTTACATCGAACTGGATCTCAACAGCGGTAAGATCCTTGAGAGTTTTCGCCCCGAAGAACGTTTTC
CAATGATGAGCACTTTTAAAGTTCTGCTATGTGGCGCGGTATTATCCCGTATTGACGCCGGGCAAGAGCAACTCGGTCGCC
GCATACACTATTCTCAGAATGACTTGGTTGAGTACTCACCAGTCACAGAAAAGCATCTTACGGATGGCATGACAGTAAGAG
AATTATGCAGTGCTGCCATAACCATGAGTGATAACACTGCGGCCAACTTACTTCTGACAACGATCGGAGGACCGAAGGAGC
TAACCGCTTTTTTGCACAACATGGGGGATCATGTAACTCGCCTTG

FIG. 2

```
ATCGTTGGGAACCGGAGCTGAATGAAGCCATACCAAACGACGAGCGTGACACCACGATGCCTGTAGCAATGGCAACAACGT
TGCGCAAACTATTAACTGGCGAACTACTTACTCTAGCTTCCCGGCAACAATTAATAGACTGGATGGAGGCGGATAAAGTTG
CAGGACCACTTCTGCGCTCGGCCCTTCCGGCTGGCTGGTTTATTGCTGATAAATCTGGAGCCGGTGAGCGTGGGTCTCGCG
GTATCATTGCAGCACTGGGGCCAGATGGTAAGCCCTCCCGTATCGTAGTTATCTACACGACGGGGAGTCAGGCAACTATGG
ATGAACGAAATAGACAGATCGCTGAGATAGGTGCCTCACTGATTAAGCATTGGTAACTGTCAGACCAAGTTTACTCATATA
TACTTTAGATTGATTTAAAACTTCATTTTTAATTTAAAAGGATCTAGGTGAAGATCCTTTTTGATAATCTCATGACCAAAA
TCCCTTAACGTGAGTTTTCGTTCCACTGAGCGTCAGACCCCGTAGAAAAGATCAAAGGATCTTCTTGAGATCCTTTTTTTC
TGCGCGTAATCTGCTGCTTGCAAACAAAAAAACCACCGCTACCAGCGGTGGTTTGTTTGCCGGATCAAGAGCTACCAACTC
TTTTTCCGAAGGTAACTGGCTTCAGCAGAGCGCAGATACCAAATACTGTTCTTCTAGTGTAGCCGTAGTTAGGCCACCACT
TCAAGAACTCTGTAGCACCGCCTACATACCTCGCTCTGCTAATCCTGTTACCAGTGGCTGCTGCCAGTGGCGATAAGTCGT
GTCTTACCGGGTTGGACTCAAGACGATAGTTACCGGATAAGGCGCAGCGGTCGGGCTGAACGGGGGGTTCGTGCACACAGC
CCAGCTTGGAGCGAACGACCTACACCGAACTGAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCGCACGAGGGAGCTTCCAGGGGGAAACGCCTGGT
ATCTTTATAGTCCTGTCGGGTTTCGCCACCTCTGACTTGAGCGTCGATTTTTGTGATGCTCGTCAGGGGGCGGAGCCTAT
GGAAAAACGCCAGCAACGCGGCCTTTTTACGGTTCCTGGCCTTTTGCTGGCCTTTTGCTCACATGTTCTTTCCTGCGTTAT
CCCCTGATTCTGTGGATAACCGTATTACCGCCTTTGAGTGAGCTGATACCGCTCGCCGCAGCCGAACGACCGAGCGCAGCG
AGTCAGTGAGCGAGGAAGCGGAAGAGCGCCCAATACGCAAACCGCCTCTCCCCGCGCGTTGGCCGATTCATTAATGCAGCT
GGCACGACAGGTTTCCCGACTGGAAAGCGGGCAGTGAGCGCAACGCAATTAATGTGAGTTAGCTCACTCATTAGGCACCCC
AGGCTTTACACTTTATGCTTCCGGCTCGTATGTTGTGTGGAATTGTGAGCGGATAACAATTTCACACAGGAAACAGCTATG
ACCATGATTACGCCAAGCTTGCATGCCTGCAGGTCGACTCTAGAGGATCTCTCTCTCAAAAACGGAGGAGGAGGA
```

FIG. 2, cont'd

SEQUENCE LISTING

```
<160> NUMBER OF SEQ ID NOS: 35

<210> SEQ ID NO 1
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: SpC2: abasic 2 carbon spacer.
<220> FEATURE:
<221> NAME/KEY: misc_feature
<222> LOCATION: (15)..(24)
<223> OTHER INFORMATION: N3CEdT: 3-N-cyanoethyl-dT.
<220> FEATURE:
<221> NAME/KEY: misc_feature
<222> LOCATION: (25)..(30)
<223> OTHER INFORMATION: SpC2: abasic 2 carbon spacer.
<220> FEATURE:
<221> NAME/KEY: misc_feature
<222> LOCATION: (31)..(31)
<223> OTHER INFORMATION: C3: 3'-propanol.

<400> SEQUENCE: 1
nnnnnnnnnn nnnnnnnnnn nnnnnnnnnn n                              31

<210> SEQ ID NO 2
<211> LENGTH: 36
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: SpC2: abasic 2 carbon spacer unit.
<220> FEATURE:
<221> NAME/KEY: misc_feature
<222> LOCATION: (15)..(24)
<223> OTHER INFORMATION: N3CEdT: 3-N-cyanoethyl-dT.
<220> FEATURE:
<221> NAME/KEY: misc_feature
<222> LOCATION: (25)..(35)
<223> OTHER INFORMATION: SpC2: abasic 2 carbon spacer unit.
<220> FEATURE:
<221> NAME/KEY: misc_feature
<222> LOCATION: (36)..(36)
<223> OTHER INFORMATION: C3: 3'-propanol.
```

<400> SEQUENCE: 2
nnnnnnnnnn nnnnnnnnnn nnnnnnnnnn nnnnnn                              36

<210> SEQ ID NO 3
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: SpC2: abasic 2 carbon spacer unit.
<220> FEATURE:
<221> NAME/KEY: misc_feature
<222> LOCATION: (16)..(22)
<223> OTHER INFORMATION: N3CEdT: 3-N-cyanoethyl-dT.
<220> FEATURE:
<221> NAME/KEY: misc_feature
<222> LOCATION: (23)..(30)
<223> OTHER INFORMATION: SpC2: abasic 2 carbon spacer unit.
<220> FEATURE:
<221> NAME/KEY: misc_feature
<222> LOCATION: (31)..(31)
<223> OTHER INFORMATION: C3: 3'-propanol.

<400> SEQUENCE: 3
nnnnnnnnnn nnnnnnnnnn nnnnnnnnnn n                                   31

<210> SEQ ID NO 4
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(17)
<223> OTHER INFORMATION: SpC2 abasic 2 carbon spacer
<220> FEATURE:
<221> NAME/KEY: misc_feature
<222> LOCATION: (18)..(27)
<223> OTHER INFORMATION: N3CEdT: 3-N-cyanoethyl-dT.
<220> FEATURE:
<221> NAME/KEY: misc_feature
<222> LOCATION: (28)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 4
nnnnnnnnnn nnnnnnnnnn nnnnnnnnnn n                                   31

<210> SEQ ID NO 5
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: SpC2 abasic 2 carbon spacer
<220> FEATURE:
<221> NAME/KEY: misc_feature
<222> LOCATION: (20)..(26)
<223> OTHER INFORMATION: N3CEdT: 3-N-cyanoethyl-dT.
<220> FEATURE:
<221> NAME/KEY: misc_feature
<222> LOCATION: (27)..(30)

```
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 5
nnnnnnnnnn nnnnnnnnnn nnnnnnnnnn n                              31

<210> SEQ ID NO 6
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(22)
<223> OTHER INFORMATION: SpC2 abasic 2 carbon spacer
<220> FEATURE:
<221> NAME/KEY: misc_feature
<222> LOCATION: (23)..(29)
<223> OTHER INFORMATION: N3CEdT: N-3-cyanoethyl-dT.
<220> FEATURE:
<221> NAME/KEY: misc_feature
<222> LOCATION: (30)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 6
nnnnnnnnnn nnnnnnnnnn nnnnnnnnnn n                              31

<210> SEQ ID NO 7
<211> LENGTH: 36
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(27)
<223> OTHER INFORMATION: SpC2 abasic 2 carbon spacer
<220> FEATURE:
<221> NAME/KEY: misc_feature
<222> LOCATION: (28)..(34)
<223> OTHER INFORMATION: N3CEdT: N-3-cyanoethyl-dT.
<220> FEATURE:
<221> NAME/KEY: misc_feature
<222> LOCATION: (35)..(35)
<223> OTHER INFORMATION: SpC2 abasic 2 carbon spacer
<220> FEATURE:
<221> NAME/KEY: misc_feature
<222> LOCATION: (36)..(36)
<223> OTHER INFORMATION: C3: 3'-propanol.

<400> SEQUENCE: 7
nnnnnnnnnn nnnnnnnnnn nnnnnnnnnn nnnnnn                         36

<210> SEQ ID NO 8
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: SpC2 abasic 2 carbon spacer
<220> FEATURE:
<221> NAME/KEY: misc_feature
```

<222> LOCATION: (15)..(24)
<223> OTHER INFORMATION: N3MedT: N-3-methyl-dT.
<220> FEATURE:
<221> NAME/KEY: misc_feature
<222> LOCATION: (25)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 8
nnnnnnnnnn nnnnnnnnnn nnnnnnnnnn n                                    31

<210> SEQ ID NO 9
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(17)
<223> OTHER INFORMATION: SpC2 abasic 2 carbon spacer
<220> FEATURE:
<221> NAME/KEY: misc_feature
<222> LOCATION: (28)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 9
nnnnnnnnnn nnnnnnnttt tttttttnnn n                                    31

<210> SEQ ID NO 10
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(23)
<223> OTHER INFORMATION: SpC2 abasic 2 carbon spacer
<220> FEATURE:
<221> NAME/KEY: misc_feature
<222> LOCATION: (24)..(29)
<223> OTHER INFORMATION: Tmp: thymidine with methylphosphonate linkage.
<220> FEATURE:
<221> NAME/KEY: misc_feature
<222> LOCATION: (30)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 10
nnnnnnnnnn nnnnnnnnnn nnnnnnnnnn n                                    31

<210> SEQ ID NO 11
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: SpC2 abasic 2 carbon spacer
<220> FEATURE:

```
<221> NAME/KEY: misc_feature
<222> LOCATION: (21)..(26)
<223> OTHER INFORMATION: Tmp: thymidine with methylphosphonate linkage.
<220> FEATURE:
<221> NAME/KEY: misc_feature
<222> LOCATION: (27)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 11
nnnnnnnnnn nnnnnnnnnn nnnnnnnnnn n                               31

<210> SEQ ID NO 12
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(17)
<223> OTHER INFORMATION: SpC2 abasic 2 carbon spacer
<220> FEATURE:
<221> NAME/KEY: misc_feature
<222> LOCATION: (18)..(23)
<223> OTHER INFORMATION: Tmp: thymidine with methylphosphonate linkage.
<220> FEATURE:
<221> NAME/KEY: misc_feature
<222> LOCATION: (24)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 12
nnnnnnnnnn nnnnnnnnnn nnnnnnnnnn n                               31

<210> SEQ ID NO 13
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(17)
<223> OTHER INFORMATION: SpC2 abasic 2 carbon spacer
<220> FEATURE:
<221> NAME/KEY: misc_feature
<222> LOCATION: (18)..(24)
<223> OTHER INFORMATION: Etheno-dA: 1,N6-etheno-dA.
<220> FEATURE:
<221> NAME/KEY: misc_feature
<222> LOCATION: (25)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 13
nnnnnnnnnn nnnnnnnnnn nnnnnnnnnn n                               31

<210> SEQ ID NO 14
<211> LENGTH: 31
<212> TYPE: DNA
<213> ORGANISM: artificial
<220> FEATURE:
<223> OTHER INFORMATION: Synthetic oligonucleotide
```

```
<220> FEATURE:
<221> NAME/KEY: misc_feature
<222> LOCATION: (1)..(22)
<223> OTHER INFORMATION: SpC2 abasic 2 carbon spacer
<220> FEATURE:
<221> NAME/KEY: misc_feature
<222> LOCATION: (23)..(29)
<223> OTHER INFORMATION: Etheno-dA: 1,N6-etheno-dA.
<220> FEATURE:
<221> NAME/KEY: misc_feature
<222> LOCATION: (30)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 14 nnnnnnnnn nnnnnnnnn nnnnnnnnn n                                        31

<210> SEQ ID NO 15
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(17)
<223> OTHER INFORMATION: SpC2 abasic 2 carbon spacer
<220> FEATURE:
<221> NAME/KEY: misc_feature
<222> LOCATION: (18)..(24)
<223> OTHER INFORMATION: Imp: inosine with methylphosphonate linkage.
<220> FEATURE:
<221> NAME/KEY: misc_feature
<222> LOCATION: (25)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 15 nnnnnnnnn nnnnnnnnn nnnnnnnnn n                                        31

<210> SEQ ID NO 16
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(17)
<223> OTHER INFORMATION: SpC2 abasic 2 carbon spacer
<220> FEATURE:
<221> NAME/KEY: misc_feature
<222> LOCATION: (18)..(24)
<223> OTHER INFORMATION: dCb: N4-(O-Levulinyl-6-oxyhexyl)-5-methyl-dC.
<220> FEATURE:
<221> NAME/KEY: misc_feature
<222> LOCATION: (25)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 16 nnnnnnnnn nnnnnnnnn nnnnnnnnn n                                        31

<210> SEQ ID NO 17
```

```
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(22)
<223> OTHER INFORMATION: SpC2 abasic 2 carbon spacer
<220> FEATURE:
<221> NAME/KEY: misc_feature
<222> LOCATION: (23)..(29)
<223> OTHER INFORMATION: dCb: N4-(O-Levulinyl-6-oxyhexyl)-5-methyl-dC.
<220> FEATURE:
<221> NAME/KEY: misc_feature
<222> LOCATION: (30)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 17
nnnnnnnnnn nnnnnnnnnn nnnnnnnnnn n                              31

<210> SEQ ID NO 18
<211> LENGTH: 34
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(22)
<223> OTHER INFORMATION: SpC2 abasic 2 carbon spacer
<220> FEATURE:
<221> NAME/KEY: misc_feature
<222> LOCATION: (23)..(29)
<223> OTHER INFORMATION: dCb: N4-(O-Levulinyl-6-oxyhexyl)-5-methyl-dC.
<220> FEATURE:
<221> NAME/KEY: misc_feature
<222> LOCATION: (30)..(33)
<223> OTHER INFORMATION: SpC2 abasic 2 carbon spacer
<220> FEATURE:
<221> NAME/KEY: misc_feature
<222> LOCATION: (34)..(34)
<223> OTHER INFORMATION: C3: 3'-propanol.

<400> SEQUENCE: 18
nnnnnnnnnn nnnnnnnnnn nnnnnnnnnn nnnn                           34

<210> SEQ ID NO 19
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(17)
<223> OTHER INFORMATION: SpC2 abasic 2 carbon spacer
<220> FEATURE:
<221> NAME/KEY: misc_feature
<222> LOCATION: (25)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 19
nnnnnnnnnn nnnnnnnaaa aaaannnnnn n                              31
```

```
<210> SEQ ID NO 20
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(22)
<223> OTHER INFORMATION: SpC2 abasic 2 carbon spacer
<220> FEATURE:
<221> NAME/KEY: misc_feature
<222> LOCATION: (30)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 20
nnnnnnnnnn nnnnnnnnnn nnaaaaaaan n                             31

<210> SEQ ID NO 21
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: SpC2 abasic 2 carbon spacer
<220> FEATURE:
<221> NAME/KEY: misc_feature
<222> LOCATION: (22)..(26)
<223> OTHER INFORMATION: 5MedC-PhEt: N4-phenylethyl-5-methyl-dC.
<220> FEATURE:
<221> NAME/KEY: misc_feature
<222> LOCATION: (27)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 21
nnnnnnnnnn nnnnnnnnnn nnnnnnnnnn n                             31

<210> SEQ ID NO 22
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: SpC2 abasic 2 carbon spacer
<220> FEATURE:
<221> NAME/KEY: misc_feature
<222> LOCATION: (20)..(20)
<223> OTHER INFORMATION: SpC2 abasic 2 carbon spacer
<220> FEATURE:
<221> NAME/KEY: misc_feature
<222> LOCATION: (22)..(22)
<223> OTHER INFORMATION: SpC2 abasic 2 carbon spacer
<220> FEATURE:
<221> NAME/KEY: misc_feature
<222> LOCATION: (24)..(24)
<223> OTHER INFORMATION: SpC2 abasic 2 carbon spacer
<220> FEATURE:
<221> NAME/KEY: misc_feature
<222> LOCATION: (26)..(26)
<223> OTHER INFORMATION: SpC2 abasic 2 carbon spacer
<220> FEATURE:
```

```
<221> NAME/KEY: misc_feature
<222> LOCATION: (28)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 22
nnnnnnnnnn nnnnnnnntn tntntntnnn n                              31

<210> SEQ ID NO 23
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(17)
<223> OTHER INFORMATION: SpC2 abasic 2 carbon spacer
<220> FEATURE:
<221> NAME/KEY: misc_feature
<222> LOCATION: (18)..(18)
<223> OTHER INFORMATION: Tmp: thymidine with methylphosphonate linkage.
<220> FEATURE:
<221> NAME/KEY: misc_feature
<222> LOCATION: (20)..(20)
<223> OTHER INFORMATION: Tmp: thymidine with methylphosphonate linkage.
<220> FEATURE:
<221> NAME/KEY: misc_feature
<222> LOCATION: (22)..(22)
<223> OTHER INFORMATION: Tmp: thymidine with methylphosphonate linkage.
<220> FEATURE:
<221> NAME/KEY: misc_feature
<222> LOCATION: (24)..(24)
<223> OTHER INFORMATION: Tmp: thymidine with methylphosphonate linkage.
<220> FEATURE:
<221> NAME/KEY: misc_feature
<222> LOCATION: (26)..(26)
<223> OTHER INFORMATION: Tmp: thymidine with methylphosphonate linkage.
<220> FEATURE:
<221> NAME/KEY: misc_feature
<222> LOCATION: (28)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 23
nnnnnnnnnn nnnnnnnntn tntntntnnn n                              31

<210> SEQ ID NO 24
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: SpC2 abasic 2 carbon spacer
<220> FEATURE:
<221> NAME/KEY: misc_feature
<222> LOCATION: (16)..(16)
<223> OTHER INFORMATION: N3CEdT: 3-N-cyanoethyl-dT .
<220> FEATURE:
<221> NAME/KEY: misc_feature
<222> LOCATION: (17)..(17)
<223> OTHER INFORMATION: 5MedC-PhEt: N4-phenylethyl-5-methyl-dC.
<220> FEATURE:
<221> NAME/KEY: misc_feature
<222> LOCATION: (18)..(18)
<223> OTHER INFORMATION: N3CEdT: 3-N-cyanoethyl-dT.
```

```
<220> FEATURE:
<221> NAME/KEY: misc_feature
<222> LOCATION: (19)..(19)
<223> OTHER INFORMATION: 5MedC-PhEt: N4-phenylethyl-5-methyl-dC.
<220> FEATURE:
<221> NAME/KEY: misc_feature
<222> LOCATION: (20)..(20)
<223> OTHER INFORMATION: N3CEdT: 3-N-cyanoethyl-dT.
<220> FEATURE:
<221> NAME/KEY: misc_feature
<222> LOCATION: (21)..(21)
<223> OTHER INFORMATION: 5MedC-PhEt: N4-phenylethyl-5-methyl-dC.
<220> FEATURE:
<221> NAME/KEY: misc_feature
<222> LOCATION: (22)..(22)
<223> OTHER INFORMATION: N3CEdT: 3-N-cyanoethyl-dT.
<220> FEATURE:
<221> NAME/KEY: misc_feature
<222> LOCATION: (23)..(23)
<223> OTHER INFORMATION: 5MedC-PhEt: N4-phenylethyl-5-methyl-dC.
<220> FEATURE:
<221> NAME/KEY: misc_feature
<222> LOCATION: (24)..(24)
<223> OTHER INFORMATION: N3CEdT: 3-N-cyanoethyl-dT.
<220> FEATURE:
<221> NAME/KEY: misc_feature
<222> LOCATION: (25)..(25)
<223> OTHER INFORMATION: 5MedC-PhEt: N4-phenylethyl-5-methyl-dC.
<220> FEATURE:
<221> NAME/KEY: misc_feature
<222> LOCATION: (26)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 24
nnnnnnnnnn nnnnnnnnnn nnnnnnnnnn n                                       31

<210> SEQ ID NO 25
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: SpC2 abasic 2 carbon spacer
<220> FEATURE:
<221> NAME/KEY: misc_feature
<222> LOCATION: (20)..(27)
<223> OTHER INFORMATION: N3CEdT: 3-N-cyanoethyl-dT.
<220> FEATURE:
<221> NAME/KEY: misc_feature
<222> LOCATION: (28)..(30)
<223> OTHER INFORMATION: SpC2 abasic 2 carbon spacer
<220> FEATURE:
<221> NAME/KEY: misc_feature
<222> LOCATION: (31)..(31)
<223> OTHER INFORMATION: C3: 3'-propanol.

<400> SEQUENCE: 25
nnnnnnnnnn nnnnnnnnnn nnnnnnnnnn n                                       31

<210> SEQ ID NO 26
<211> LENGTH: 305
<212> TYPE: PRT
<213> ORGANISM: Staphyloccocus aureus

<400> SEQUENCE: 26

Ala Asp Ser Asp Ile Asn Ile Lys Thr Gly Thr Thr Asp Ile Gly Ser
1               5                   10                  15
```

```
Asn Thr Thr Val Lys Thr Gly Asp Leu Val Thr Tyr Asp Lys Glu Asn
             20                  25                  30

Gly Met His Lys Lys Val Phe Tyr Ser Phe Ile Asp Asp Lys Asn His
         35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Gly Leu Ser Ala Trp Ser His Pro Gln Phe Glu
    290                 295                 300

Lys
305

<210> SEQ ID NO 27
<211> LENGTH: 293
<212> TYPE: PRT
<213> ORGANISM: artificial
<220> FEATURE:
<223> OTHER INFORMATION: truncated alpha-hemolysin polypeptide

<400> SEQUENCE: 27

Ala Asp Ser Asp Ile Asn Ile Lys Thr Gly Thr Thr Asp Ile Gly Ser
1               5                  10                  15

Asn Thr Thr Val Lys Thr Gly Asp Leu Val Thr Tyr Asp Lys Glu Asn
             20                  25                  30

Gly Met His Lys Lys Val Phe Tyr Ser Phe Ile Asp Asp Lys Asn His
         35                  40                  45

Asn Lys Lys Leu Leu Val Ile Arg Thr Lys Gly Thr Ile Ala Gly Gln
 50                  55                  60
```

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 28
<211> LENGTH: 10
<212> TYPE: PRT
<213> ORGANISM: artificial
<220> FEATURE:
<223> OTHER INFORMATION: Synthetic polypeptide

<400> SEQUENCE: 28

Ala His Ile Val Met Val Asp Ala Tyr Lys
1               5                   10

```
<210> SEQ ID NO 29
<211> LENGTH: 10
<212> TYPE: PRT
<213> ORGANISM: artificial
<220> FEATURE:
<223> OTHER INFORMATION: Synthetic polypeptide

<400> SEQUENCE: 29

Gly Gly Ser Ser Gly Gly Ser Ser Gly Gly
1               5                   10

<210> SEQ ID NO 30
<211> LENGTH: 13
<212> TYPE: PRT
<213> ORGANISM: artificial
<220> FEATURE:
<223> OTHER INFORMATION: Synthetic polypeptide

<400> SEQUENCE: 30

Ala His Ile Val Met Val Asp Ala Tyr Lys Pro Thr Lys
1               5                   10

<210> SEQ ID NO 31
<211> LENGTH: 8
<212> TYPE: PRT
<213> ORGANISM: artificial
<220> FEATURE:
<223> OTHER INFORMATION: Synthetic polypeptide

<400> SEQUENCE: 31

Lys Gly His His His His His His
1               5

<210> SEQ ID NO 32
<211> LENGTH: 31
<212> TYPE: PRT
<213> ORGANISM: artificial
<220> FEATURE:
<223> OTHER INFORMATION: Synthetic polypeptide

<400> SEQUENCE: 32

Gly Gly Ser Ser Gly Gly Ser Ser Gly Gly Ala His Ile Val Met Val
1               5                   10                  15

Asp Ala Tyr Lys Pro Thr Lys Lys Gly His His His His His His
            20                  25                  30

<210> SEQ ID NO 33
<211> LENGTH: 5466
<212> TYPE: DNA
<213> ORGANISM: artificial
<220> FEATURE:
<223> OTHER INFORMATION: pUC19 dumbbell sequence

<400> SEQUENCE: 33
cagtcagtag agagagagat cctctagagt cgacctgcag gcatgcaagc ttggcgtaat      60
catggtcata gctgtttcct gtgtgaaatt gttatccgct cacaattcca cacaacatac    120
gagccggaag cataaagtgt aaagcctggg gtgcctaatg agtgagctaa ctcacattaa    180
ttgcgttgcg ctcactgccc gctttccagt cgggaaacct gtcgtgccag ctgcattaat    240
gaatcggcca acgcgcgggg agaggcggtt tgcgtattgg gcgctcttcc gcttcctcgc    300
tcactgactc gctgcgctcg gtcgttcggc tgcggcgagc ggtatcagct cactcaaagg    360
cggtaatacg gttatccaca gaatcagggg ataacgcagg aaagaacatg tgagcaaaag    420
gccagcaaaa ggccaggaac cgtaaaaagg ccgcgttgct ggcgtttttc cataggctcc    480
```

```
gcccccctga cgagcatcac aaaaatcgac gctcaagtca gaggtggcga aacccgacag    540
gactataaag ataccaggcg tttcccctg gaagctccct cgtgcgctct cctgttccga     600
ccctgccgct taccggatac ctgtccgcct ttctcccttc gggaagcgtg gcgctttctc    660
atagctcacg ctgtaggtat ctcagttcgg tgtaggtcgt tcgctccaag ctgggctgtg    720
tgcacgaacc ccccgttcag cccgaccgct gcgccttatc cggtaactat cgtcttgagt    780
ccaacccggt aagacacgac ttatcgccac tggcagcagc cactggtaac aggattagca    840
gagcgaggta tgtaggcggt gctacagagt tcttgaagtg gtggcctaac tacggctaca    900
ctagaagaac agtatttggt atctgcgctc tgctgaagcc agttaccttc ggaaaaagag    960
ttggtagctc ttgatccggc aaacaaacca ccgctggtag cggtggtttt tttgtttgca   1020
agcagcagat tacgcgcaga aaaaaaggat ctcaagaaga tcctttgatc ttttctacgg   1080
ggtctgacgc tcagtggaac gaaaactcac gttaagggat tttggtcatg agattatcaa   1140
aaaggatctt cacctagatc cttttaaatt aaaaatgaag ttttaaatca atctaaagta   1200
tatatgagta aacttggtct gacagttacc aatgcttaat cagtgaggca cctatctcag   1260
cgatctgtct atttcgttca tccatagttg cctgactccc cgtcgtgtag ataactacga   1320
tacgggaggg cttaccatct ggccccagtg ctgcaatgat accgcgagac ccacgctcac   1380
cggctccaga tttatcagca ataaaccagc cagccggaag ggccgagcgc agaagtggtc   1440
ctgcaacttt atccgcctcc atccagtcta ttaattgttg ccgggaagct agagtaagta   1500
gttcgccagt taatagtttg cgcaacgttg ttgccattgc tacaggcatc gtggtgtcac   1560
gctcgtcgtt tggtatggct tcattcagct ccggttccca acgatcaagg cgagttacat   1620 gatccccat gttgtgcaaa aaagcggtta gctccttcgg tcctccgatc gttgtcagaa    1680
gtaagttggc cgcagtgtta tcactcatgg ttatggcagc actgcataat tctcttactg   1740
tcatgccatc cgtaagatgc ttttctgtga ctggtgagta ctcaaccaag tcattctgag   1800
aatagtgtat gcggcgaccg agttgctctt gcccggcgtc aatacgggat aataccgcgc   1860
cacatagcag aactttaaaa gtgctcatca ttggaaaacg ttcttcgggg cgaaaactct   1920
caaggatctt accgctgttg agatccagtt cgatgtaacc cactcgtgca cccaactgat   1980
cttcagcatc ttttactttc accagcgttt ctgggtgagc aaaaacagga aggcaaaatg   2040
ccgcaaaaaa gggaataagg gcgacacgga aatgttgaat actcatactc ttcctttttc   2100
aatattattg aagcatttat cagggttatt gtctcatgag cggatacata tttgaatgta   2160
tttagaaaaa taaacaaata ggggttccgc gcacatttcc ccgaaaagtg ccacctgacg   2220
tctaagaaac cattattatc atgacattaa cctataaaaa taggcgtatc acgaggccct   2280
ttcgtctcgc gcgtttcggt gatgacggtg aaaacctctg acacatgcag ctcccggaga   2340
cggtcacagc ttgtctgtaa gcggatgccg ggagcagaca gcccgtcag ggcgcgtcag    2400 cgggtgttgg cgggtgtcgg gctggctta actatgcggc atcagagcag attgtactga    2460
gagtgcacca tatgcggtgt gaaataccgc acagatgcgt aaggagaaaa taccgcatca    2520
ggcgccattc gccattcagg ctgcgcaact gttgggaagg gcgatcggtg cgggcctctt    2580
cgctattacg ccagctggcg aaggggat gtgctgcaag gcgattaagt tgggtaacgc     2640
cagggttttc ccagtcacga cgttgtaaaa cgacggccag tgaattcgag ctcggtaccc    2700
ggggatctct ctctcaaaaa cggaggagga ggacagtcag tagagagaga gatccccggg    2760
taccgagctc gaattcactg gccgtcgttt tacaacgtcg tgactgggaa aaccctggcg    2820
```

```
ttacccaact taatcgcctt gcagcacatc cccctttcgc cagctggcgt aatagcgaag      2880
aggcccgcac cgatcgccct tcccaacagt tgcgcagcct gaatggcgaa tggcgcctga      2940
tgcggtattt tctccttacg catctgtgcg gtatttcaca ccgcatatgg tgcactctca      3000
gtacaatctg ctctgatgcc gcatagttaa gccagccccg acacccgcca cacccgctg       3060 acgcgccctg acgggcttgt ctgctcccgg catccgctta cagacaagct gtgaccgtct      3120 ccggagctg catgtgtcag aggttttcac cgtcatcacc gaaacgcgcg agacgaaagg       3180
gcctcgtgat acgcctattt ttataggtta atgtcatgat aataatggtt tcttagacgt      3240
caggtggcac ttttcgggga atgtgcgcg gaacccctat ttgtttattt ttctaaatac       3300
attcaaatat gtatccgctc atgagacaat aaccctgata aatgcttcaa taatattgaa      3360
aaaggaagag tatgagtatt caacatttcc gtgtcgccct tattcccttt tttgcggcat      3420
tttgccttcc tgttttttgct cacccagaaa cgctggtgaa agtaaaagat gctgaagatc     3480
agttgggtgc acgagtgggt tacatcgaac tggatctcaa cagcggtaag atccttgaga      3540
gttttcgccc cgaagaacgt tttccaatga tgagcacttt taaagttctg ctatgtggcg      3600
cggtattatc ccgtattgac gccgggcaag agcaactcgg tcgccgcata cactattctc      3660
agaatgactt ggttgagtac tcaccagtca cagaaaagca tcttacggat ggcatgacag      3720
taagagaatt atgcagtgct gccataacca tgagtgataa cactgcggcc aacttacttc      3780
tgacaacgat cggaggaccg aaggagctaa ccgcttttt gcacaacatg ggggatcatg       3840
taactcgcct tgatcgttgg gaaccggagc tgaatgaagc cataccaaac gacgagcgtg      3900
acaccacgat gcctgtagca atggcaacaa cgttgcgcaa actattaact ggcgaactac      3960
ttactctagc ttcccggcaa caattaatag actggatgga ggcggataaa gttgcaggac      4020
cacttctgcg ctcggccctt ccggctggct ggtttattgc tgataaatct ggagccggtg      4080
agcgtgggtc tcgcggtatc attgcagcac tggggccaga tggtaagccc tcccgtatcg      4140
tagttatcta cacgacgggg agtcaggcaa ctatggatga acgaaataga cagatcgctg      4200
agataggtgc ctcactgatt aagcattggt aactgtcaga ccaagtttac tcatatatac      4260
tttagattga tttaaaactt cattttaat ttaaaggat ctaggtgaag atccttttg        4320 ataatctcat gaccaaaatc ccttaacgtg agttttcgtt ccactgagcg tcagaccccg      4380
tagaaaagat caaaggatct tcttgagatc ctttttttct gcgcgtaatc tgctgcttgc      4440
aaacaaaaaa accaccgcta ccagcggtgg tttgtttgcc ggatcaagag ctaccaactc      4500 ttttccgaa ggtaactggc ttcagcagag cgcagatacc aaatactgtt cttctagtgt       4560
agccgtagtt aggccaccac ttcaagaact ctgtagcacc gcctacatac ctcgctctgc      4620
taatcctgtt accagtggct gctgccagtg gcgataagtc gtgtcttacc gggttggact      4680
caagacgata gttaccggat aaggcgcagc ggtcgggctg aacggggggt tcgtgcacac      4740
agcccagctt ggagcgaacg acctacaccg aactgagata cctacagcgt gagctatgag      4800
aaagcgccac gcttcccgaa gggagaaagg cggacaggta tccggtaagc ggcagggtcg      4860
```

-continued

```
gaacaggaga gcgcacgagg gagcttccag ggggaaacgc ctggtatctt tatagtcctg    4920
tcgggtttcg ccacctctga cttgagcgtc gattttgtg atgctcgtca ggggggcgga     4980
gcctatggaa aaacgccagc aacgcggcct ttttacggtt cctggccttt tgctggcctt    5040
ttgctcacat gttctttcct gcgttatccc ctgattctgt ggataaccgt attaccgcct    5100
ttgagtgagc tgataccgct cgccgcagcc gaacgaccga gcgcagcgag tcagtgagcg    5160
aggaagcgga gagcgcccca atacgcaaac cgcctctccc cgcgcgttgg ccgattcatt    5220
aatgcagctg gcacgacagg tttcccgact ggaaagcggg cagtgagcgc aacgcaatta    5280
atgtgagtta gctcactcat taggcacccc aggctttaca ctttatgctt ccggctcgta    5340
tgttgtgtgg aattgtgagc ggataacaat ttcacacagg aaacagctat gaccatgatt    5400
acgccaagct tgcatgcctg caggtcgact ctagaggatc tctctctcaa aaacggagga    5460
ggagga                                                               5466
```

<210> SEQ ID NO 34
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (3)..(30)
<223> OTHER INFORMATION: SpC2: abasic 2 carbon spacer.
<220> FEATURE:
<221> NAME/KEY: misc_feature
<222> LOCATION: (31)..(31)
<223> OTHER INFORMATION: C3: 3'-propanol.

<400> SEQUENCE: 34
ttnnnnnnnn nnnnnnnnnn nnnnnnnnnn n                                    31

<210> SEQ ID NO 35
<211> LENGTH: 31
<212> TYPE: DNA
<213> ORGANISM: artificial
<220> FEATURE:
<223> OTHER INFORMATION: Synthetic oligonucleotide
<220> FEATURE:
<221> NAME/KEY: misc_feature
<222> LOCATION: (3)..(28)
<223> OTHER INFORMATION: dSp: abasic furan spacer.
<220> FEATURE:
<221> NAME/KEY: misc_feature
<222> LOCATION: (31)..(31)
<223> OTHER INFORMATION: C3: 3'-propanol.

<400> SEQUENCE: 35
ttnnnnnnnn nnnnnnnnnn nnnnnnnntt n                                    31

TAGGED NUCLEOSIDE COMPOUNDS USEFUL FOR NANOPORE DETECTION

CROSS-REFERENCE TO RELATED APPLICATIONS

This is a continuation of PCT/EP2019/054791, filed Feb. 27, 2019 which claims priority to U.S. Provisional Patent Application No. 62/773,995, filed Nov. 30, 2018, and to U.S. Provisional Patent Application No. 62/636,807, filed Feb. 28, 2018, the content of each of which is incorporated herein by reference in its entirety

REFERENCE TO SEQUENCE LISTING

The official copy of the Sequence Listing is submitted concurrently with the specification as an ASCII formatted text file with a file name of "P34709US2_ST25", a creation date of Aug. 24, 2020, and a size of 29,167 bytes. The Sequence Listing filed herewith is part of the specification and is incorporated in its entirety by reference herein.

FIELD

This application relates to tagged nucleoside compounds comprising a nucleotide polyphosphate covalently attached to a tag, wherein the compound is a polymerase substrate and the polymer moiety is capable of entering a nanopore linked to the polymerase and thereby altering the flow of ions through the nanopore. The present disclosure provides methods for preparing the tagged nucleoside compounds and for their use as nanopore-detectable tags, such as in nanopore-based nucleic acid detection and sequencing.

BACKGROUND

Numerous methods for using nanopores to detect nucleic acids (e.g., DNA) or other molecules are known in the art. One common method involves applying an electric field across the nanopore to induce the nucleic acid to enter and partially block the nanopore, and measuring the current level and duration of the current blockage as the molecule rapidly enters and translocates through the pore. Both the current level and the duration of the blockage can reveal information about the molecule (typically, a polymeric molecule such as DNA). This type of nanopore detection method has also been carried out using polymeric polyethylene glycol (PEG) molecules and the length was of the polymer was found to affect both the current level and dwell time. See e.g., Joseph W. F. Robertson, Claudio G. Rodrigues, Vincent M. Stanford, Kenneth A. Rubinson, Oleg V. Krasilnikov, and John J. Kasianowicz, *Proc. Nat'l. Acad. Sci. USA*, 104; 8207 (2007).

Another method of observing a molecule using a nanopore is to attach a bulky moiety to the molecule so that it cannot pass, or cannot quickly pass, through the pore. An example is the use of the relatively bulky protein streptavidin that tightly binds biotin, which can easily be covalently attached to DNA. With the DNA held between the pull of the electric field and the bulky protein, it can remain in a fixed position in the nanopore long enough (e.g., milliseconds to seconds) to allow an accurate measurement of current flowing through the pore. It can then be released (e.g., by turning off or reversing the electric field) and the pore used again for another measurement. In addition to streptavidin, other proteins and molecules can be used as translocation blockers. For instance, antibodies which bind specific ligands or enzymes like DNA polymerase can be used. Even double-stranded DNA may be too large to pass through an α-hemolysin ("α-HL") pore, and it too can be used to hold DNA (or other polymers) in a fixed position in a nanopore under the pull of an electric field.

Nucleic acid sequencing is the process for determining the nucleotide sequence of a nucleic acid. Such sequence information may be helpful in diagnosing and/or treating a subject. For example, the sequence of a nucleic acid of a subject may be used to identify, diagnose, and potentially develop treatments for genetic diseases. As another example, research into pathogens may lead to treatment for contagious diseases. Since some diseases are characterized by as little as one nucleotide difference in a chain of millions of nucleotides, high throughput, highly accurate sequencing is essential.

Single-molecule sequencing-by-synthesis ("SBS") techniques using nanopores have been developed. See e.g., US Pat. Publ. Nos. 2013/0244340 A1, 2013/0264207 A1, 2014/0134616 A1. Nanopore SBS uses a polymerase (or other strand-extending enzyme) to synthesize a DNA strand complementary to a target sequence template and concurrently uses a nanopore to detect the identity of each nucleotide monomer as the polymerase adds it to the growing strand, thereby determining the target sequence. Each added nucleotide monomer is detected by monitoring signals due to ion flow through a nanopore that is located adjacent to the polymerase active site as the strand is synthesized. Obtaining an accurate, reproducible ion flow signal requires positioning the polymerase active site near a nanopore, and the use of a tag on each added nucleotide. The tag moiety should be capable of entering the nanopore and altering the ion flow through the pore. Importantly, the tag should reside in the nanopore for a sufficient amount of time (i.e., "dwell time") to provide for a detectable, identifiable, and reproducible signal associated with altering ion flow through the nanopore (relative to the baseline "open current" flow), such that the specific nucleotide associated with the tag can be distinguished unambiguously from the other tagged nucleotides in the SBS solution.

Kumar et al., (2012) "PEG-Labeled Nucleotides and Nanopore Detection for Single Molecule DNA Sequencing by Synthesis," Scientific Reports, 2:684; DOI: 10.1038/srep00684, describes using a nanopore to distinguish four different length PEG-coumarin tags attached via a terminal 5'-phosphoramidate to a dG nucleotide, and separately demonstrates efficient and accurate incorporation of these four PEG-coumarin tagged dG nucleotides by DNA polymerase. See also, US Patent Application Publications US 2013/0244340 A1, published Sep. 19, 2013, US 2013/0264207 A1, published Oct. 10, 2013, and US 2014/0134616 A1, published May 14, 2014.

WO 2013/154999 and WO 2013/191793 describe the use of tagged nucleotides for nanopore SBS and disclose the possible use of a single nucleotide attached to a single tag comprising branched PEG chains.

WO 2015/148402 describes the use of tagged nucleotides for nanopore SBS comprising a single nucleotide attached to a single tag, wherein the tag comprises any or a range of oligonucleotides (or oligonucleotide analogues) that have lengths of 30 monomer units or longer.

"Wide-pore" mutants of the nanopore α-HL have been developed which exhibit a longer lifetime when used in nanopore devices and exposed to the electrochemical conditions used in conducting high-throughput nanopore sequencing. The longer nanopore lifetime provides greater read-lengths and overall accuracy in sequencing. Structurally, the wide-pore mutants are engineered to effectively eliminate the naturally occurring constriction site (i.e., narrowest portion of pore) that is located at a depth of approximately 40 angstroms from the cis opening of the pore, and which has a diameter of approximately 10 angstroms in diameter. The wide-pore mutations create a new constriction site located deeper into the pore, approximately 65 angstroms from the cis opening, and which is wider—approximately 13 angstroms in diameter.

The above-described prior disclosures fail to teach tagged nucleotide structures that can provide distinctive, reproducible tag current level signals upon entering the pore of a wide-pore mutant. Accordingly, there remains a need for tagged nucleotide compositions and methods that can be used with wide-pore mutants and thereby improve the efficiency and accuracy of high-throughput nanopore detection techniques, such as nucleic acid SBS.

SUMMARY

The present disclosure provides compounds comprising a nucleoside-5'-oligophosphate moiety covalently linked through the terminal phosphate group of the oligophosphate to the 5'-end of a negatively charged polymer moiety of structural formula (I)

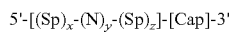
(I)

wherein, x=12-24; y=5-15; z=1-8; x+y+z=27-35

Sp is a monomer unit of formula (1a)

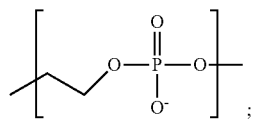
(1a)

N is a unit of formula (2a), (2b), or (2c)

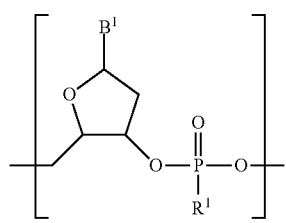
(2a)

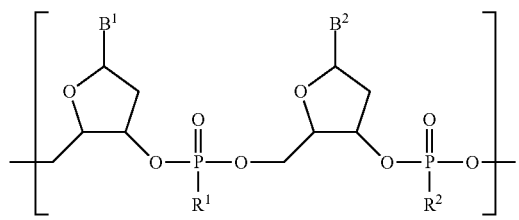
(2b)

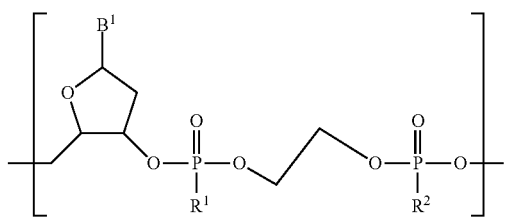
(2c)

wherein, $B^1$ and $B^2$ are independently selected from a natural nucleobase, a modified nucleobase, and H; $R^1$ and $R^2$ are independently selected from $O^-$, $CH_3$, and H; and Cap is a 3'-end capping unit. In some embodiments the compound is a substrate for a polymerase linked to a nanopore.

In various embodiments of the present disclosure, the compounds can include one or more of the following features: x=14-22; x+y+z=30; the groups $R^1$ and/or $R^2$ are independently selected from $O^-$ and $CH_3$; $B^1$ and/or $B^2$ are independently selected from the group consisting of adenine, cytosine, guanine, thymine, uracil, hypoxanthine, N3CEdT, N3MedT, etheno-dA, 5MedC, 5MedC-PhEt, and dCb; the Cap is a 3'-propanol group; and/or N is a unit of formula (2a).

In some embodiments of the compound, x=14-22, y=6-10, z=3-6, x+y+z=30, N is a unit of formula (2a), and Cap is a 3'-propanol group.

In some embodiments of the compound, $R^1$ is $O^-$ and $B^1$ is a modified nucleobase, optionally, the modified base is independently selected from N3CEdT, N3MedT, etheno-dA, 5MedC, 5MedC-PhEt, and dCb. In some embodiments of the compound, $R^1$ is $CH_3$ and $B^1$ is thymine or hypoxanthine.

In various embodiments of the present disclosure, the compound can further comprise a structural formula (II)

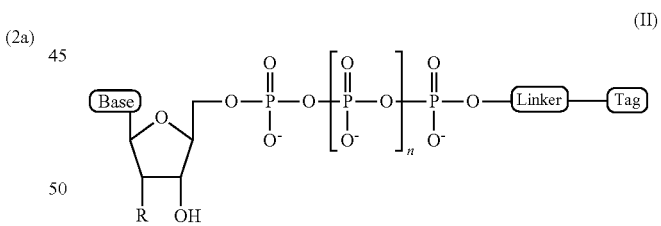
(II)

wherein, Base is selected from adenine, cytosine, guanine, thymine, and uracil; R is selected from H and OH; n is from 1 to 4; Linker is a linker comprising a covalently bonded chain of 2 to 100 atoms; and Tag is the negatively charged polymer moiety of structural formula (I). In some embodiments, the linker comprises a chemical group selected from the group consisting of: ester, ether, thioether, amine, amide, imide, carbonate, carbamate, squarate, thiazole, thiazolidine, hydrazone, oxime, triazole, dihydropyridazine, phosphodiester, polyethylene glycol (PEG), Pictet-Spengler adduct, and any combination thereof.

In some embodiments of the present disclosure, the compound has a structural formula (IIa)

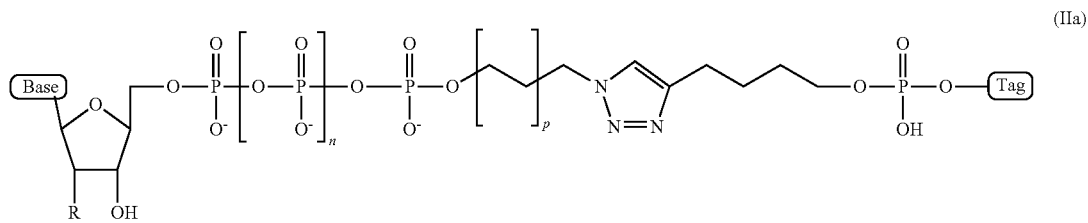

(IIa)

wherein, Base is selected from adenine, cytosine, guanine, thymine, and uracil; R is selected from H and OH; n is from 1 to 4, p is from 2 to 10; and Tag is the polymer moiety of structural formula (I).

In some embodiments of the present disclosure, the compound has a structural formula (IIb)

(IIb)

wherein, Base is selected from adenine, cytosine, guanine, thymine, and uracil; R is selected from H and OH; n is from 1 to 4; p is from 2 to 10; and Tag is the polymer moiety of structural formula (I).

In various embodiments of the compounds of formulas (II), (IIa), and (IIb), the compound has the features R=H, n=4, and p=5.

In various embodiments of the compounds of the present disclosure the polymer moiety is capable of entering the cis opening of a nanopore and altering the flow of ions through the nanopore, wherein the nanopore has a constriction site that is approximately 13 angstroms in diameter and which is located approximately 65 angstroms from the cis opening of the pore. In some embodiments, the nanopore comprises a 6:1 ratio of α-HL subunits, wherein the subunits comprise amino acid substitutions E111N and M113A; optionally the subunits further comprise amino acid substitutions selected from D128K, K147N, and V149K. In some embodiments, the 6:1 ratio comprises 6× subunits comprising an amino acid substitution H144A, and a 1× subunit comprising a C-terminal fusion to a polymerase.

In some embodiments, the nanopore is nanopore comprising a 6:1 ratio of α-HL subunits is a wide-pore mutant nanopore selected from the following:

| | |
|---|---|
| P-01 | 6x subunits: (H35G, E111N, M113A, D127G, D128G, T129G, K131G, H144A, K147N, V149K)<br>1x subunit: (E111N, M113A, D127G, D128G, T129G, K131G, K147N) + C-terminal SpyTag peptide fusion |
| P-02 | 6x subunits: (A1K, S3K, H35G, E111N, M113A, D127G, D128G, T129G, K131G, H144A, K147N, V149K)<br>1x subunit: (H35G, E111N, M113A, D127G, D128G, T129G, K131G, K147N) + C-terminal SpyTag peptide fusion |
| P-03 | 6x subunits: (0K, A1K, H35G, E111N, M113A, D127G, D128G, T129G, K131G, H144A, K147N, V149K)<br>1x subunit: wild-type α-HL + C-terminal SpyTag peptide fusion |
| P-04 | 6x subunits: (H35G, E111N, M113A, D127G, D128G, T129G, K131G, H144A, K147N, V149K)<br>1x subunit: (H35G, E111N, M113A, D127G, D128G, T129G, K131G, K147N) + C-terminal SpyTag peptide fusion |
| P-05 | 6x subunits: (H35G, E111N, M113A, D127G, D128K, T129G, K131G, H144A, K147N, V149K)<br>1x subunit: (H35G, E111N, M113A, D127G, D128G, T129G, K131G, K147N) + C-terminal SpyTag peptide fusion |
| P-06 | 6x subunits: (D2N, H35G, S106K, E111N, M113A, D127G, D128G, T129G, K131G, H144A, K147N, V149K)<br>1x subunit: (H35G, E111N, M113A, D127G, D128G, T129G, K131G, K147N) + C-terminal SpyTag peptide fusion |
| P-07 | 6x subunits: (H35G, E111N, M113A, D127G, D128K, T129G, K131G, H144A, K147N, V149K, M298A, Ss07d)<br>1x subunit: (H35G, E111N, M113A, D127G, D128G, T129G, K131G, K147N) + C-terminal SpyTag peptide fusion |
| P-08 | 6x subunits: (H35G, E70K, E111N, M113A, D127G, D128K, T129G, K131G, H144A, K147N, V149K)<br>1x subunit: (H35G, E111N, M113A, D127G, D128G, T129G, K131G, K147N) + C-terminal SpyTag peptide fusion |

In some embodiments of the compounds, the altering of the flow of ions through the nanopore results in a measured current across the nanopore that differs from O.C. current by at least 5%, optionally by at least 10%, at least 25%, or at least 50%. In some embodiments, the altering of the flow of ions results in a measured current across the nanopore that is increased above O.C.

In some embodiments of the compounds, the polymer moiety has an overall negative charge of from (−25) to (−50), optionally an overall negative charge of from (−30) to (−40), or optionally an overall negative charge of from (−31) to (−37). In some embodiments, the polymer moiety comprises at least one charged group per 10 angstroms of molecular length, optionally at least one charged group per 7.5 angstroms of molecular length, or at least one charged group per 3.5 angstroms of molecular length.

In some embodiments, the present disclosure provides a composition comprising a set of compounds as disclosed herein, wherein each compound of the set comprises a different tag which results in a different altering of the flow of ions through a wide-pore nanopore when the tag enters the nanopore. In some embodiments of the composition comprising a set of compounds, each compound of the set comprises a different tag which results in a different altering of the flow of ions through a nanopore when the tag enters the nanopore, wherein at least one of the compounds has a structural formula (II)

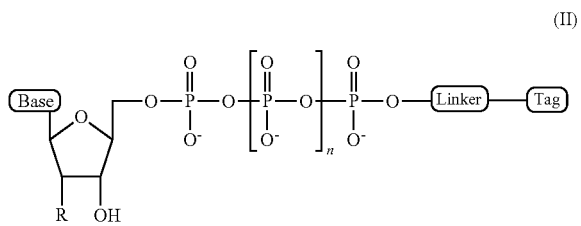

(II)

wherein, Base is selected from adenine, cytosine, guanine, thymine, and uracil; R is selected from H and OH; n is from 1 to 4; Linker is a linker comprising a covalently bonded chain of 2 to 100 atoms; and Tag is the polymer moiety of structural formula (I) as disclosed herein above.

In some embodiments of the composition, the at least one compound having structural formula (II) comprises a polymer moiety of formula (I) selected from group consisting of:

-(SpC2)$_{14}$-(N3CEdT)$_{10}$-(SpC2)$_{6}$-C3
(SEQ ID NO: 1)
-(SpC2)$_{14}$-(N3CEdT)$_{10}$-(SpC2)$_{11}$-C3
(SEQ ID NO: 2)
-(SpC2)$_{15}$-(N3CEdT)$_{7}$-(SpC2)$_{8}$-C3
(SEQ ID NO: 3)
-(SpC2)$_{17}$-(N3CEdT)$_{10}$-(SpC2)$_{3}$-C3
(SEQ ID NO: 4)
-(SpC2)$_{19}$-(N3CEdT)$_{7}$-(SpC2)$_{4}$-C3
(SEQ ID NO: 5)
-(SpC2)$_{22}$-(N3CEdT)$_{7}$-(SpC2)$_{1}$-C3
(SEQ ID NO: 6)
-(SpC2)$_{27}$-(N3CEdT)$_{7}$-(SpC2)$_{1}$-C3
(SEQ ID NO: 7)
-(SpC2)$_{14}$-(N3MedT)$_{10}$-(SpC2)$_{6}$-C3
(SEQ ID NO: 8)
-(SpC2)$_{17}$-(dT)$_{10}$-(SpC2)$_{3}$-C3
(SEQ ID NO: 9)
-(SpC2)$_{23}$-(Tmp)$_{6}$-(SpC2)$_{1}$-C3
(SEQ ID NO: 10)
-(SpC2)$_{20}$-(Tmp)$_{6}$-(SpC2)$_{4}$-C3
(SEQ ID NO: 11)
-(SpC2)$_{17}$-(Tmp)$_{6}$-(SpC2)$_{7}$-C3
(SEQ ID NO: 12)

-continued

-(SpC2)$_{17}$-(Etheno-dA)$_{7}$-(SpC2)$_{6}$-C3
(SEQ ID NO: 13)
-(SpC2)$_{22}$-(Etheno-dA)$_{7}$-(SpC2)$_{1}$-C3
(SEQ ID NO: 14)
-(SpC2)$_{17}$-(Imp)$_{7}$-(SpC2)$_{6}$-C3
(SEQ ID NO: 15)
-(SpC2)$_{17}$-(dCb)$_{7}$-(SpC2)$_{6}$-C3
(SEQ ID NO: 16)
-(SpC2)$_{22}$-(dCb)$_{7}$-(SpC2)$_{1}$-C3
(SEQ ID NO: 17)
-(SpC2)$_{22}$-(dCb)$_{7}$-(SpC2)$_{4}$-C3
(SEQ ID NO: 18)
-(SpC2)$_{17}$-(dA)$_{7}$-(SpC2)$_{6}$-C3
(SEQ ID NO: 19)
-(SpC2)$_{22}$-(dA)$_{7}$-(SpC2)$_{1}$-C3
(SEQ ID NO: 20)
-(SpC2)$_{21}$-(5MedC-PhEt)$_{5}$-(SpC2)$_{4}$-C3
(SEQ ID NO: 21)
-(SpC2)$_{17}$-(SpC2-dT)$_{5}$-(SpC2)$_{3}$-C3
(SEQ ID NO: 22)
-(SpC2)$_{17}$-(Tmp-dT)$_{5}$-(SpC2)$_{3}$-C3
(SEQ ID NO: 23)
-(SpC2)$_{15}$-(N3CEdT-5MedC-PhEt)$_{5}$-(SpC2)$_{5}$-C3
(SEQ ID NO: 24)
-(SpC2)$_{19}$-(N3CEdT)$_{8}$-(SpC2)$_{3}$-C3
(SEQ ID NO: 25)

In some embodiments of the composition, the set of compounds is selected from Set 1, Set 2, Set 3, Set 4, Set 5, Set 6, and Set 7:

| Set 1 |
| --- |
| dC6P-(Linker)-T$_2$-(SpC2)$_{28}$-C3<br>dA6P-(Linker)-T$_2$-(dSp)$_{26}$-T$_2$-C3<br>dT6P-(Linker)-(SpC2)$_{19}$-(N3CEdT)$_{7}$-(SpC2)$_{4}$-C3<br>dG6P-(Linker)-(SpC2)$_{14}$-(N3CEdT)$_{10}$-(SpC2)$_{6}$-C3 |

| Set 2 |
| --- |
| dT6P-(Linker)-(SpC2)$_{22}$-dA$_{7}$-(SpC2)-C3<br>dC6P-(Linker)-(SpC2)$_{21}$-(5MedC-PhEt)$_{5}$-(SpC2)$_{4}$-C3<br>dA6P-(Linker)-(SpC2)$_{22}$-(dCb)$_{7}$-(SpC2)$_{4}$-C3<br>dG6P-(Linker)-(SpC2)$_{20}$-(Tmp)$_{6}$-(SpC2)$_{4}$-C3 |

| Set 3 |
| --- |
| dC6P-(Linker)-T$_2$-(SpC2)$_{28}$-C3<br>dT6P-(Linker)-(SpC2)$_{19}$-(N3CEdT)$_{7}$-(SpC2)$_{4}$-C3<br>dA6P-(Linker)-(SpC2)$_{17}$-(N3CEdT)$_{10}$-(SpC2)$_{3}$-C3<br>dG6P-(Linker)-(SpC2)$_{15}$-(N3CEdT-5MedC-PhEt)$_{5}$-(SpC2)$_{5}$-C3 |

| Set 4 |
| --- |
| dA6P-(Linker)-(SpC2)$_{14}$-(N3CEdT)$_{10}$-(SpC2)$_{6}$-C3<br>dC6P-(Linker)-T$_2$-(SpC2)$_{28}$-C3<br>dG6P-(Linker)-T$_2$-(dSp)$_{26}$-T$_2$-C3<br>dT6P-(Linker)-(SpC2)$_{14}$-(N3MedT)$_{10}$-(SpC2)$_{6}$-C3 |

| Set 5 |
| --- |
| dA6P-(Linker)-(SpC2)$_{14}$-(N3CEdT)$_{10}$-(SpC2)$_{6}$-C3<br>dC6P-(Linker)-T$_2$-(SpC2)$_{28}$-C3<br>dG6P-(Linker)-T$_2$-(dSp)$_{26}$-T$_2$-C3<br>dT6P-(Linker)-(SpC2)$_{19}$-(N3CEdT)$_{7}$-(SpC2)$_{4}$-C3 |

| Set 6 |
| --- |
| dA6P-(Linker)-(SpC2)$_{14}$-(N3CEdT)$_{10}$-(SpC2)$_{6}$-C3<br>dC6P-(Linker)-T$_2$-(SpC2)$_{28}$-C3<br>dG6P-(Linker)-T$_2$-(dSp)$_{26}$-T$_2$-C3<br>dT6P-(Linker)-(SpC2)$_{19}$-(N3CEdT)$_{8}$-(SpC2)$_{3}$-C3 |

-continued

Set 7 dA6P-(Linker)-(SpC2)$_{14}$-(N3CEdT)$_{10}$-(SpC2)$_{11}$-C3
dC6P-(Linker)-T$_2$-(SpC2)$_{28}$-C3
dG6P-(Linker)-T$_2$-(dSp)$_{26}$-T$_2$-C3
dT6P-(Linker)-(SpC2)$_{19}$-(N3CEdT)$_8$-(SpC2)$_3$-C3

In some embodiments, the present disclosure also provided a method for determining the sequence of a nucleic acid comprising:
(a) providing a nanopore sequencing composition comprising: a membrane, an electrode on the cis side and the trans side of the membrane, a wide-pore mutant nanopore with its pore extending through the membrane, an electrolyte solution comprising ions in contact with both electrodes, an active polymerase situated adjacent to the nanopore, and a primer strand complexed with the polymerase;
(b) contacting the nanopore sequencing composition with (i) a strand of the nucleic acid; and (ii) a set of compounds each comprising a different nucleoside-5'-oligophosphate moiety covalently linked to a tag, wherein each member of the set of compounds has a different tag which results in a different altering of the flow of ions through a nanopore when the tag enters the nanopore, wherein at least one of the compounds of the set is a compound as disclosed herein (i.e., a wide-pore ion flow altering tagged nucleotide compound); and
(c) detecting the different altering of the flows of ions resulting from the entry of the different tags in the nanopore over time and correlating to each of the different compounds incorporated by the polymerase which are complementary to the nucleic acid sequence, and thereby determining the nucleic acid sequence.

BRIEF DESCRIPTION OF THE DRAWINGS

FIG. 2 depicts the 5466 bp sequence of the pUC19 dumbbell DNA template used in the wide-pore tagged nucleotide nanopore detection methods described in Example 2.

DETAILED DESCRIPTION

Figure 1:
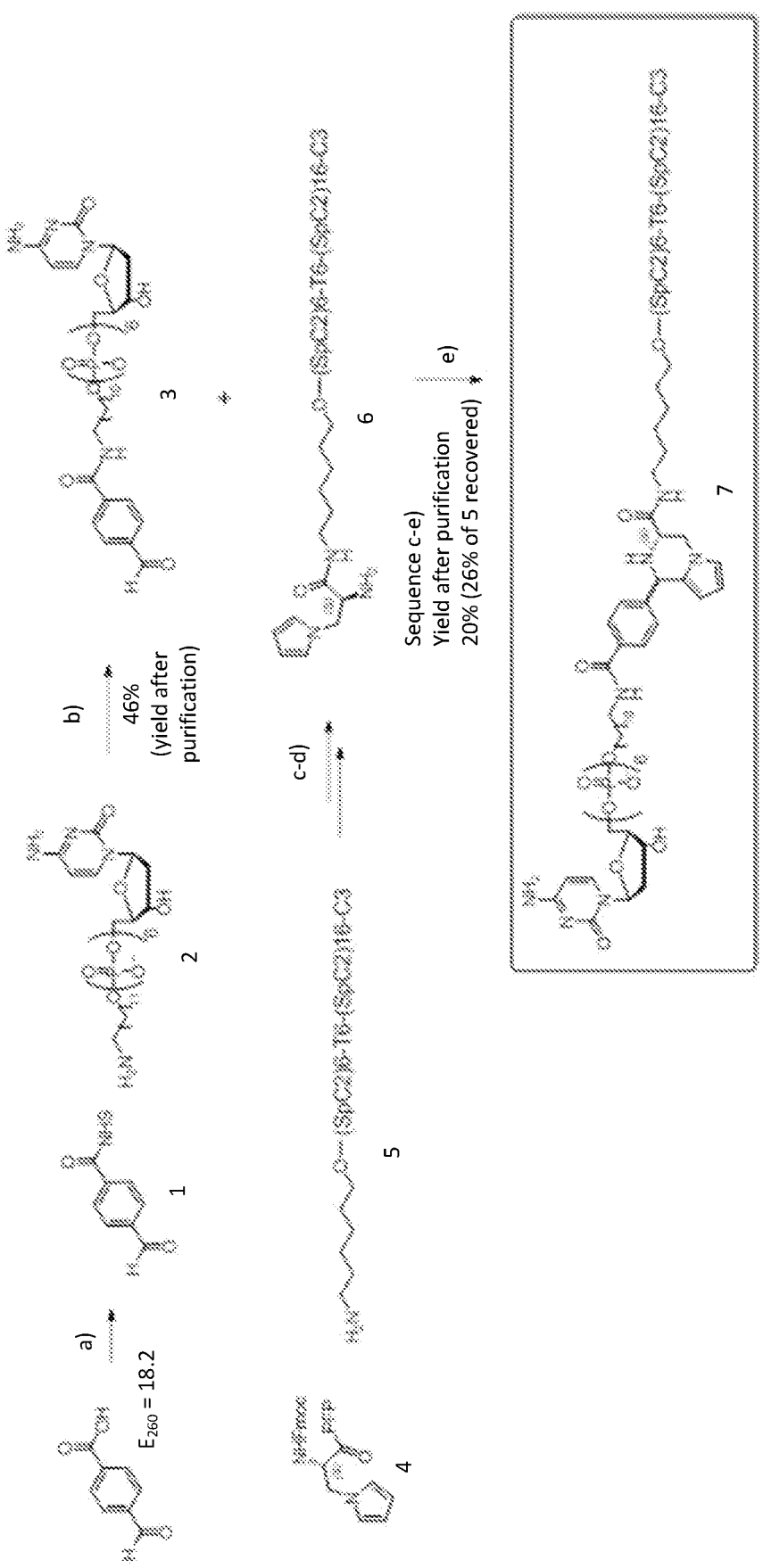
FIG. 1 depicts a reaction scheme for preparing a tagged nucleotide compound of formula (IIb) having a Pictet-Spengler adduct linker.

For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example, "1 to 50" includes "2 to 25", "5 to 20", "25 to 50", "1 to 10", etc.

It is to be understood that both the foregoing general description, including the drawings, and the following detailed description are exemplary and explanatory only and are not restrictive of this disclosure.

Definitions

"Nucleic acid," as used herein, refers to a molecule of one or more nucleic acid subunits which comprise one of the nucleobases, adenine (A), cytosine (C), guanine (G), thymine (T), and uracil (U), or variants thereof. Nucleic acid can refer to a polymer of nucleotides (e.g., dAMP, dCMP, dGMP, dTMP), also referred to as a polynucleotide or oligonucleotide, and includes DNA, RNA, in both single and double-stranded form, and hybrids thereof.

"Nucleotide," as used herein refers to a nucleoside-5'-oligophosphate compound, or structural analog of a nucleoside-5'-oligophosphate, which is capable of acting as a substrate or inhibitor of a nucleic acid polymerase. Exemplary nucleotides include, but are not limited to, nucleoside-5'-triphosphates (e.g., dATP, dCTP, dGTP, dTTP, and dUTP); nucleosides (e.g., dA, dC, dG, dT, and dU) with 5'-oligophosphate chains of 4 or more phosphates in length (e.g., 5'-tetraphosphate, 5'-pentaphosphate, 5'-hexaphosphate, 5'-heptaphosphate, 5'-octaphosphate); and structural analogs of nucleoside-5'-triphosphates that can have a modified nucleobase moiety (e.g., a substituted purine or pyrimidine nucleobase), a modified sugar moiety (e.g., an O-alkylated sugar), and/or a modified oligophosphate moiety (e.g., an oligophosphate comprising a thio-phosphate, a methylene, and/or other bridges between phosphates).

"Nucleoside," as used herein, refers to a molecular moiety that comprises a naturally occurring or non-naturally occurring nucleobase attached to a sugar moiety (e.g., ribose or deoxyribose).

"Oligophosphate," as used herein, refers to a molecular moiety that comprises an oligomer of phosphate groups. For example, an oligophosphate can comprise an oligomer of from 2 to 20 phosphates, an oligomer of from 3 to 12 phosphates, an oligomer of from 3 to 9 phosphates.

"Polymerase," as used herein, refers to any natural or non-naturally occurring enzyme or other catalyst that is capable of catalyzing a polymerization reaction, such as the polymerization of nucleotide monomers to form a nucleic acid polymer. Exemplary polymerases that may be used in the compositions and methods of the present disclosure include the nucleic acid polymerases such as DNA polymerase (e.g., enzyme of class EC 2.7.7.7), RNA polymerase (e.g., enzyme of class EC 2.7.7.6 or EC 2.7.7.48), reverse transcriptase (e.g., enzyme of class EC 2.7.7.49), and DNA ligase (e.g., enzyme of class EC 6.5.1.1).

"Moiety," as used herein, refers to part of a molecule.

"Linker," as used herein, refers to any molecular moiety that provides a bonding attachment with some space between two or more molecules, molecular groups, and/or molecular moieties.

"Tag," as used herein, refers to a moiety or part of a molecule that enables or enhances the ability to detect and/or identify, either directly or indirectly, a molecule or molecular complex, which is coupled to the tag. For example, the tag can provide a detectable property or characteristic, such as steric bulk or volume, electrostatic charge, electrochemical potential, optical and/or spectroscopic signature.

"3'-end capping unit" as used herein, refers to a moiety attached to the 3'-terminus of a nucleic acid that protects the nucleic acid from digestion in the presence of exonuclease or polymerase enzymes. Exemplary 3'-end capping units are disclosed in WO 2015/148402 and include, but are not limited to the 3' propanol group ("C3") resulting from oligonucleotide synthesis using an initial spacer phosphoramidite C3 (3-(4,4'-dimethoxytrityloxy)propyl-1-[(2-cyanoethyl)-(N,N-diisopropyl)]-phosphoramidite).

"Nanopore," as used herein, refers to a pore, channel, or passage formed or otherwise provided in a membrane or other barrier material that has a characteristic width or diameter of about 1 angstrom to about 10,000 angstroms. A nanopore can be made of a naturally-occurring pore-forming protein, such as α-hemolysin from S. aureus, or a mutant or variant of a wild-type pore-forming protein, either non-naturally occurring (i.e., engineered) such as α-HL-C46, or naturally occurring. A membrane may be an organic membrane, such as a lipid bilayer, or a synthetic membrane made of a non-naturally occurring polymeric material. The nanopore may be disposed adjacent or in proximity to a sensor, a sensing circuit, or an electrode coupled to a sensing circuit, such as, for example, a complementary metal-oxide semiconductor (CMOS) or field effect transistor (FET) circuit.

"Wide-pore mutant," as used herein, refers to a nanopore engineered to have a constriction site of about 13 angstroms diameter located at a depth of about 65 angstroms as measured from the widest portion of the cis side of the pore when it is embedded in a membrane. Exemplary wide-pore mutants include α-HL heptamers comprising a 6:1 ratio of mutant α-HL subunits as disclosed elsewhere herein.

"Nanopore-detectable tag" as used herein refers to a tag that can enter into, become positioned in, be captured by, translocate through, and/or traverse a nanopore and thereby result in a detectable change in current through the nanopore. Exemplary nanopore-detectable tags include, but are not limited to, natural or synthetic polymers, such as polyethylene glycol, oligonucleotides, polypeptides, carbohydrates, peptide nucleic acid polymers, locked nucleic acid polymers, any of which may be optionally modified with or linked to chemical groups, such as dye moieties, or fluorophores, that can result in detectable nanopore current changes.

"Ion flow," as used herein, refers to the movement of ions, typically in a solution, due to an electromotive force, such as the potential between an anode and a cathode. Ion flow typically can be measured as current or the decay of an electrostatic potential.

"Ion flow altering," as used herein in the context of nanopore detection, refers to the characteristic of resulting in a decrease or an increase in ion flow through a nanopore relative to the ion flow through the nanopore in its "open channel" (O.C.) state.

"Open channel current," "O.C. current," or "Background current" as used herein refers to the current level measured across a nanopore when a potential is applied and the nanopore is open (e.g., no tag is present in the nanopore).

"Tag current" as used herein refers to the current level measured across a nanopore when a potential is applied and a tag is present the nanopore. For example, depending on a tag's specific characteristics (e.g., overall charge, structure, etc.), the presence of the tag in a nanopore can decrease ion flow through the nanopore and thereby result in a decrease in measured tag current level.

"Dwell time" as used herein in the context of capture of a tag in a nanopore refers to the time that the tag spends in the nanopore as detected by a tag current.

"Molecular length," as used herein, refers to the average length of a molecule (or a moiety) at its longest axial dimension when the molecule (or moiety) is in its average solution conformation.

"Molecular diameter," as used herein, refers to the average length of a molecule (or a moiety) at its the shortest axial dimension when the molecule (or moiety) is in its average solution conformation.

"Overall charge," as used herein, refers to the sum of the positively and negatively charged chemical groups that make up a molecule (or a moiety). For example, a tag moiety comprising a polymer of 30 monomer units with 30 phosphodiester groups (each of which has a charge of (−1) at pH 7) is a negatively-charged polymer with an overall charge of (−30).

"Negatively-charged," as used herein in the context of a tag moiety refers to a tag moiety having an overall charge that is negative.

Detailed Description of Various Embodiments

Overview: Tagged Nucleoside Compounds and Nanopore Sequencing

The present disclosure describes compounds comprising negatively-charged polymer moieties having structures optimized for use as nanopore-detectable tags with wide-pore mutants, tagged nucleoside compounds capable of acting as polymerase substrates comprising these polymer moieties, compositions including sets of these tagged nucleoside compounds, and related methods, devices, and systems that are useful for nanopore detection and sequencing of nucleic acids. The tagged nucleoside compounds can be used in methods to accurately detect individual nucleotide incorporation by a nucleic acid polymerase into a growing strand that is complementary to a template nucleic acid strand.

Generally, nanopore-based nucleotide acid sequencing uses a mixture of four nucleotide analogs (e.g., dA6P, dC6P, dG6P, and dT6P) that can be incorporated by an enzyme into a growing strand. Each nucleotide analog has a covalently attached tag moiety that provides an identifiable, and distinguishable signature when detected with a nanopore. The strand extending enzyme (e.g., Pol6 DNA polymerase) specifically binds the tagged nucleotide compound that is complimentary to a template nucleic acid strand which is hybridized to the growing nucleic acid strand at its active site. The strand extending enzyme then catalytically couples (i.e., incorporates) the complimentary nucleotide moiety of the tagged nucleotide compound to the end of the growing nucleic acid strand. Completion of the catalytic incorporation event results in the release of the tag moiety and the oligophosphate moiety (minus the one phosphate incorporated into the growing strand) which then passes through the adjacent nanopore. Even before it undergoes catalytic process that releases it from the incorporated nucleotide however, the tag moiety of a tagged nucleotide compound enters the pore of the nanopore under an applied potential, thereby altering the background ion flow through the nanopore and providing a detectable tag current signal.

A negatively-charged polymer moiety, or "tag," upon entering a nanopore can result in an altered flow of ions through the nanopore. In a properly set-up nanopore device, this change in ion flow can result in a detectable tag current signal. A decrease in ion flow is detected as a signal that is a percentage of (or below) the "open channel" (or "O.C.") current resulting from positive ion flow through the nanopore with no tag moiety present. To date, various molecular properties of tag moieties have been modified (e.g., mass, volume, 3-D structure, electrostatic charge) and found to affect the interaction with the pore, thereby allowing for nanopore detection to distinguish different tag moieties each of which can correspond to a different nucleotide. A variety of nanopore systems and methods for using them to detect tagged molecules including tagged nucleotides for nucleic acid sequencing are known in the art. See, for example, U.S. patent application Ser. No. 12/308,091, Ju et al., filed May 18, 2009; U.S. patent application Ser. No. 13/994,431, Ju et al., filed Jun. 14, 2013; US Patent Application Publications US 2013/0244340 A1, published Sep. 19, 2013, US 2013/0264207 A1, published Oct. 10, 2013, and US 2014/0134616 A1, published May 14, 2014; PCT Appl. No. PCT/US13/35635, Ju et al., filed Apr. 8, 2013; and PCT Appl. No. PCT/US13/35640, Ju et al., filed Apr. 8, 2013, PCT International Publication Nos. WO2015/148402 and WO 2017/042038, and U.S. Provisional Patent Appl. No. 62/235,551, filed Sep. 30, 2015, each of which is hereby incorporated herein by reference in its entirety.

Compounds Optimized as Tag Moieties for Wide-Pore Mutants

The present disclosure provides compounds optimized for altering (i.e., decreasing or increasing) ion flow through wide-pore mutant nanopores. These compounds are useful as tag moieties for tagged nucleosides, and other wide-pore ion flow altering tag embodiments. The compounds are disclosed herein and structurally characterized by a range of structures and sub-structures. Generally, the wide-pore ion flow altering tagged compounds of the present disclosure comprise a negatively-charged polymer moiety having a structure that is optimized for entering a wide-pore mutant nanopore and upon entering the nanopore altering the flow of the ions through the nanopore thereby providing a distinctive and reproducible tag current signal.

Generally, the tagged nucleotide compound of the present disclosure comprises a wide-pore ion flow altering tag moiety covalently linked to a nucleoside-5'-oligophosphate moiety, wherein the tag moiety comprises a negatively-charged polymer moiety which is capable of entering a nanopore and upon entering a nanopore in the presence of ions results in an altered flow of the ions through the nanopore. In some embodiments, the nucleoside-5'-oligophosphate moiety of the tagged nucleotide is capable of being a substrate for a polymerase covalently linked to the polymer moiety As described elsewhere herein, the ion flow altering characteristics of the tag moieties of the present disclosure with wide-pore mutants result in technical advantages including increased accuracy, sensitivity, lifetime and read-length, particularly when used for detection in nanopore devices comprising wide-pore mutant nanopores. In some embodiments, the altered ion flow results in a distinctive tag current signal measured across a wide-pore nanopore that is altered by at least 10%, 15%, 20%, 25%, 30%, 40%, 50%, 75%, 90%, or more relative to the O.C. signal across the nanopore.

Although the present disclosure describes and exemplifies embodiments in which the wide-pore ion flow altering tag moieties of the present disclosure can be used in tagged nucleotide compounds for nanopore based sequencing-by-synthesis (SBS) methods, it is also contemplated that the tag moieties disclosed herein can be conjugated to other types of compounds and used as tags in any method that involves wide-pore nanopore detection of a tagged compound. It is contemplated that any assay using nanopore detection of a tagged compound could be easily adapted to use a wide-pore ion flow altering tag moiety of the present disclosure. Thus, the ordinary artisan can use the synthesis methods disclosed herein to prepare range of wide-pore ion flow altering tagged compounds using the tag moiety structures disclosed herein.

In some embodiments, the present disclosure provides a compound comprising a nucleoside-5'-oligophosphate moiety covalently linked through the terminal phosphate group of the oligophosphate to the 5'-end of a negatively charged polymer moiety of structural formula (I)

wherein, x=14-22; y=5-10; z=1-8; and x+y+z=27-35; Sp is a monomer unit of formula (1a)

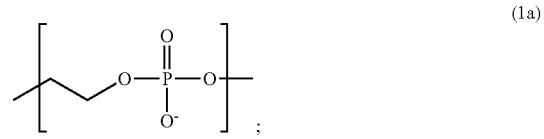

N is a unit of formula (2a), (2b), or (2c)

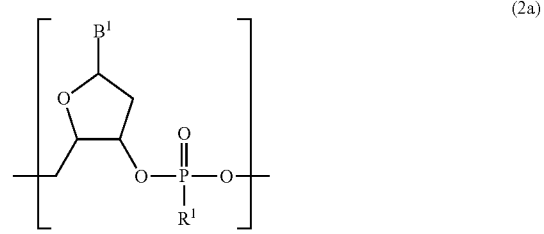

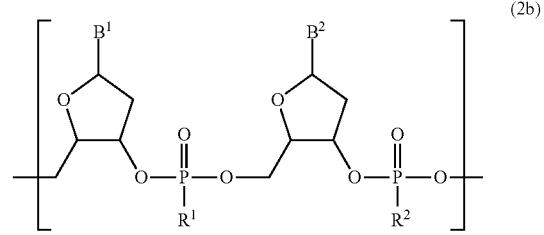

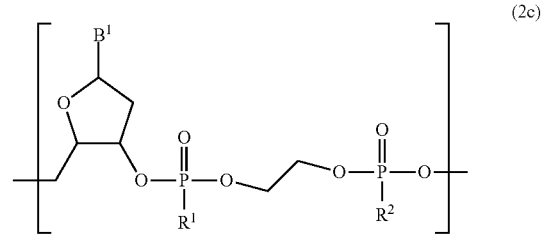

wherein, $B^1$ and $B^2$ are independently selected from a natural nucleobase, a modified nucleobase, and H; $R^1$ and $R^2$ are independently selected from $O^-$, $CH_3$, and H; and Cap is a 3'-end capping unit.

The structure of the tag comprising the negatively charged polymer moiety of structural formula (I) is optimized for entering and altering the flow of ions through a wide-pore mutant nanopore. As noted elsewhere herein, a wide-pore mutant has a constriction site of about 13 angstroms diameter located at a depth of about 65 angstroms as measured from the widest portion of the cis side of the pore when it is embedded in a membrane. The genus of structures of formula (I) include a range of structural features, such as the total polymer length, m, 5' SpC2 spacer (Sp) length, x, and constriction site interacting group, N, that provide for distinctive and reproducible signal upon entering a wide-pore mutant. Accordingly, in various embodiments of the present disclosure, the compounds can include tag moieties having one or more of the following features: x=14-22; x+y+z=30; the groups $R^1$ and/or $R^2$ are independently selected from $O^-$ and $CH_3$; $B^1$ and/or $B^2$ are independently selected from the group consisting of adenine, cytosine, guanine, thymine, uracil, hypoxanthine, N3CEdT, N3MedT, etheno-dA, 5MedC, 5MedC-PhEt, and dCb; the Cap is a 3'-propanol group; and/or N is a unit of formula (2a). In some embodiments of the compound, the negatively charged polymer moiety has the features x=14-22, y=6-10, z=3-6, x+y+z=30, N is a unit of formula (2a), and Cap is a 3'-propanol group.

In some embodiments of the compound, the constriction site interacting group, N, comprises single phosphate monomer units (i.e., formula (2a)) wherein the nucleobase is a modified nucleobase. Accordingly, in some embodiments, R is $O^-$ and $B^1$ is a modified nucleobase. In some embodiments, the modified nucleobase is independently selected from N3CEdT, N3MedT, etheno-dA, 5MedC, 5MedC-PhEt, and dCb.

In some embodiments of the compound, the constriction site interacting group, N, comprises a single monomer unit that is a methyl phosphonate monomer unit (e.g., Tmp or Imp). These units are less negatively charged than the phosphate monomer units and provide distinct tag current levels when present in the wide-pore constriction site. Accordingly, in some embodiment, $R^1$ is $CH_3$ and $B^1$ is thymine or hypoxanthine.

In some embodiments of the compound, the nucleoside-5'-oligophosphate moiety is a substrate for a polymerase linked to a nanopore. In such embodiments, the nucleoside can be any nucleoside capable of being incorporated by a strand-extending enzyme, such as a polymerase, when the nucleoside is covalently coupled to an oligophosphate, such as a triphosphate. The nucleoside can comprise a naturally occurring or non-naturally occurring nucleobase, and a naturally occurring or non-naturally occurring sugar moiety, such as a ribose or deoxyribose group. In some embodiments, the nucleobase is selected from group consisting of adenine, cytosine, guanine, thymine, and uracil. The sugar moiety should provide a free hydroxyl group at a position (e.g., a 3'-OH group) that can form a phosphodiester bond with a growing polynucleotide strand when catalytically incorporated by a strand extending enzyme. The nucleoside sugar moiety should also provide a group allowing covalent attachment of an oligophosphate moiety (e.g., a 5'-O group).

In some embodiments, the compounds of the present disclosure are further defined to include tagged nucleotide compounds of structural formula (II)

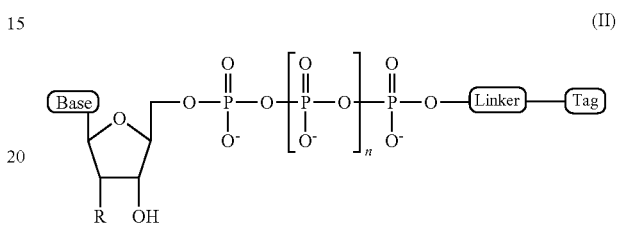

(II)

wherein, "Base" is a nucleobase selected from adenine, cytosine, guanine, thymine, and uracil; R is selected from H and OH; n is from 1 to 4; "Linker" is a linker group comprising a covalently bonded chain of 2 to 100 atoms; and "Tag" is the negatively charged polymer moiety of structural formula (I) as disclosed above and elsewhere herein.

As described in greater detail below, the Linker can comprise a chemical group selected from the group consisting of: ester, ether, thioether, amine, amide, imide, carbonate, carbamate, squarate, thiazole, thiazolidine, hydrazone, oxime, triazole, dihydropyridazine, phosphodiester, polyethylene glycol (PEG), Pictet-Spengler adduct, and any combination thereof.

In one embodiment of the compound as defined by the structure of formula (II), the present disclosure also provides a compound of structural formula (IIa)

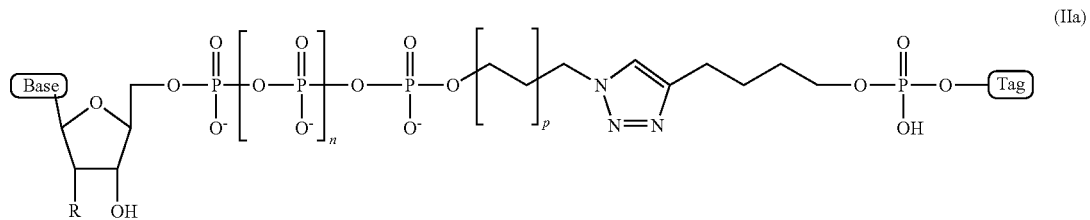

(IIa)

wherein, Base is selected from adenine, cytosine, guanine, thymine, and uracil; R is selected from H and OH; n is from 1 to 4, p is from 2 to 10; and Tag is the polymer moiety of structural formula (I).

In another embodiments of the tagged nucleoside compound of formula (II), the present disclosure provides a compound of structural formula (IIb)

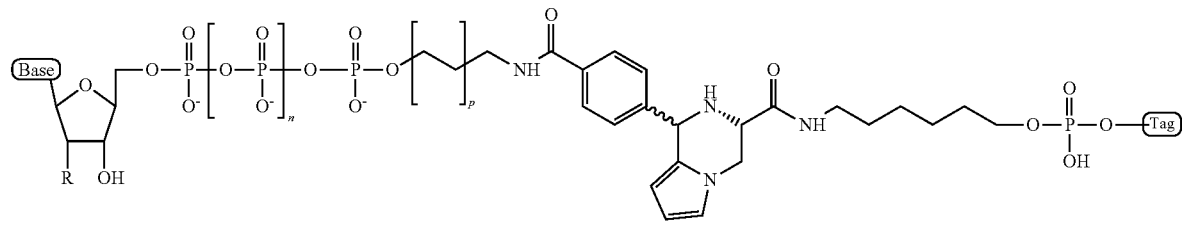

(IIb)

wherein, Base is selected from adenine, cytosine, guanine, thymine, and uracil; R is selected from H and OH; n is from 1 to 4; p is from 2 to 10; and Tag is the polymer moiety of structural formula (I).

In some embodiments, the present disclosure provides certain useful substructures of formulas (II), (IIa), and (IIb). Accordingly, in some embodiments, the compound the compounds of formulas (II), (IIa), and (IIb) can have the features R=H, n=4, and p=5.

In some embodiments, the nucleobase ("Base") can be any naturally or non-naturally occurring (e.g., chemically modified) nucleobase which is capable of being incorporated by a strand-extending enzyme, such as a polymerase. In some embodiments, the nucleobase is selected from group consisting of adenine, cytosine, guanine, thymine, and uracil.

The oligophosphate (P) moiety of the ion flow altering tagged nucleotide compounds can be any oligophosphate which, when attached to the 5'-O of the nucleoside, allows the resulting nucleotide to still be capable of being incorporated by a strand-extending enzyme, such as a polymerase. Generally, strand-extending enzymes, such as polymerase, are capable of incorporating nucleotides comprising oligophosphates having chains of from 3 to 12 phosphate groups. Accordingly, in some embodiments of the compounds of the present disclosure the 5'-oligophosphate group can comprise 3 to 12 phosphate groups.

As depicted in the compound of structural formula (II), the values of n=1 to n=4 represent an oligophosphate of 3 to 6 phosphates. Thus, in some embodiments of the present disclosure, the ion flow altering tagged nucleotide compound comprises an 5'-oligophosphate comprises 3 to 6 phosphate groups (or n=1 to 4 for formula (II)). In some embodiments, the oligophosphate group comprises 4 to 6 phosphate groups (or n=2 to 4 for formula (II)). In some embodiments, the oligophosphate group comprises 6 phosphate groups (or n=4 for formula (II)).

It is further contemplated that the compounds of the present disclosure can include a 5'-oligophosphate moiety that comprises modified phosphate groups, phosphate analogs, or other non-phosphate chemical groups, provided that the inclusion of such phosphate groups does not prevent the resulting compound from being incorporated by a strand-extending enzyme when the oligophosphate is attached to the 5'-O of the nucleoside. Typically, incorporation by a strand-extending enzyme requires a naturally occurring phosphate group at the α-position and a phosphodiester bond between the α-position and β-positions of the oligophosphate. Thus, in some embodiments, the 5'-oligophosphate can comprise a thiophosphate group. Additionally, it is contemplated that the 5'-oligophosphate can include an oligomer of phosphate or phosphate-analog groups with one or more non-phosphate groups, such as a methylene, and/or a bridging group between two or more phosphate groups.

Linkers

It is contemplated that a wide range of linkers can be used to covalently couple the negatively-charged polymer moieties, or tags, of the present disclosure to the 5'-oligophosphate of a compound desired to used for wide-pore mutant nanopore detection (e.g., tagged nucleotide compound). Generally, the linker can comprise any molecular moiety that is capable of providing a covalent coupling and a spacing or structure between the compound and the polymer moiety that is desired to be used as the tag for the particular wide-pore nanopore detection method. Such linker parameters can be routinely determined by the ordinary artisan using methods known in the art.

In some embodiments, the desired spacing or structure can be selected and optimized for the specific use of the ion flow altering tagged nucleotide compound. For example, a linker can be selected that provides a spacing that allows the ion flow altering tag moiety to enter and reside in the nanopore when any one of the multiple tagged nucleotides forms a ternary complex with an adjacent polymerase. Generally, the negatively charged polymer structure of the ion flow altering tag moiety should adopt a rod-like conformation that is capable of rapidly entering (or threading) into the nanopore having length sufficient to place the constriction site interacting group, N, in the constriction site of the nanopore. Depending on how the polymerase is coupled to the nanopore, a linker of a slightly shorter or longer length may be selected so as to allow the ion flow altering tag moiety to attain this nanopore spanning position (and provide the optimal ion flow enhancement associate signal) when the tagged nucleotide forms a proper ternary complex at the polymerase active site.

Generally, the linkers useful with the ion flow altering tagged nucleotide compounds of the present disclosure (e.g., compounds of formulas (I) and (II)) comprise a covalently bonded chain of 2 to 100 atoms. In some embodiments, the linker chain of 2 to 100 atoms comprises one or more chemical moieties selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, carbonate, carbamate, squarate, thiazole, thiazolidine, hydrazone, oxime, triazole, dihydropyridazine, phosphodiester, polyethylene glycol (PEG), Pictet-Spengler adduct, and combinations thereof. A variety of linkers comprising a range of chemical moieties that are useful in the ion flow altering tagged compounds of the present disclosure are described and exemplified herein.

Typically, in the ion flow altering tagged nucleotide embodiments of the present disclosure, the linker is formed during the preparation of the compound (e.g., compound of structural formula (II)), in a chemical reaction that covalent couples the terminal phosphate (or phosphate analog) of the 5'-oligophosphate moiety to the tag polymer moiety, or to a linker moiety that is attached to, or can be covalently attached to the tag. More specifically, this chemical reaction typically involves a tag moiety modified with a reactive linker-forming group and a nucleotide comprising an oligophosphate moiety, wherein the terminus of the oligophosphate is also modified with a reactive linker-forming group. This type of linker forming chemical reaction in Scheme 1.

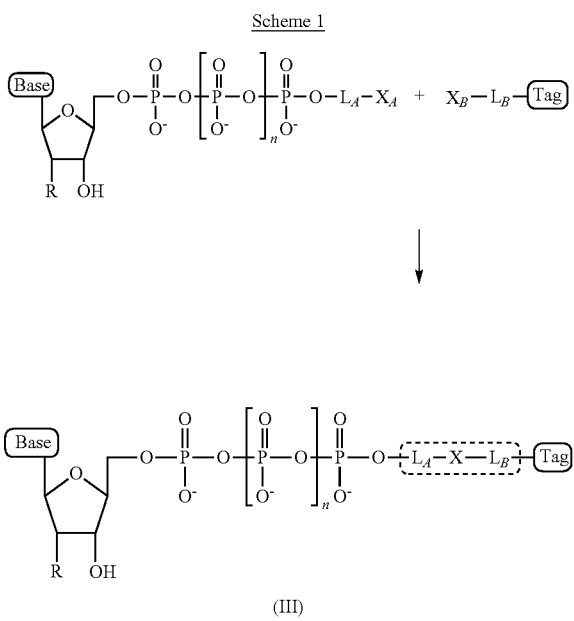

Scheme 1

(III)

As depicted in Scheme 1, $X_A$ and $X_B$ are reactive linker forming groups, and $L_A$ and $L_B$, are precursor linker moieties to the finally formed linkers of structure -$L_B$-X-$L_A$-found in the tagged nucleotide compound of formula (III). Thus, $X_A$ and $X_B$ are chemical moieties which are capable of undergoing a chemical reaction that results in a covalent coupling between one of the multiple nucleotide and the tag. The product of each covalent coupling reaction between the linker forming groups, $X_A$ and $X_B$, is a linker comprising a general structure -$L_B$-X-$L_A$-. Thus, in some embodiments of the present disclosure, the linker "L" or "Linker" as in the compound of formula (II) is a linker of structural formula "-$L_B$-X-$L_A$-" as depicted in Scheme 1.

The chemical moiety, "X" (of the "-$L_B$-X-$L_A$-") of structural formula (III) is the new chemical linker moiety produced in the linker forming reaction. Often, the name of the particular chemical group X is used to denote the type of linker, although the other parts of the linker provided by $L_A$ and $L_B$ may contribute substantially to the overall structure of the linker. In some embodiments, the linker comprises a chemical moiety, X, produced in the linker forming reaction between the linker forming reagents, $X_A$ and $X_B$, wherein X is a chemical moiety selected from the group consisting of ester, ether, thioether, amine, amide, imide, carbonate, carbamate, squarate, thiazole, thiazolidine, hydrazone, oxime, triazole, dihydropyridazine, phosphodiester, polyethylene glycol (PEG), and Pictet-Spengler adduct.

The chemical moieties, $L_A$ and $L_B$ are chemical groups which can effectively act as linkers or spacers between the nucleoside-5'-oligophosphate moiety or the tag moiety and their linker forming reagent groups, $X_A$ and $X_B$. Typically, $L_A$ and $L_B$ are chemical moieties that do not react in the linker forming reaction but which provide additional spacing or structure for the final formed linker. The $L_A$ and $L_B$ moieties can be the same or different. In some embodiments, $L_A$ or $L_B$ can be much longer or shorter than the other, and/or provide different structural features, for example features that result in more or less conformational flexibility. Accordingly, in some embodiments, $L_A$ and $L_B$ moieties useful in the wide-pore ion flow altering tagged nucleotide compounds of the present disclosure comprise a covalently bonded chain of 2 to 100 atoms, and optionally, one or more chemical moieties selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, carbonate, carbamate, squarate, thiazole, thiazolidine, hydrazone, oxime, triazole, dihydropyridazine, phosphodiester, polyethylene glycol (PEG), and combinations thereof.

Thus, in some embodiments, the present disclosure provides a wide-pore ion flow altering tagged nucleotide compound of structural formula (III)

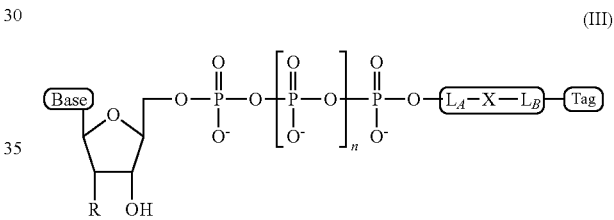

(III)

wherein, Base is selected from adenosine, cytidine, guanosine, thymidine, and uridine; R is selected from H and OH; n is from 1 to 4; $L_B$-X-$L_A$ is the linker, wherein (a) $L_A$ and $L_B$ each independently comprises a chemical moiety selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, carbonate, carbamate, squarate, thiazole, thiazolidine, hydrazone, oxime, triazole, dihydropyridazine, phosphodiester, polyethylene glycol (PEG), Pictet-Spengler adduct and combinations thereof; and (b) X comprises a chemical moiety selected from the group consisting of ester, ether, thioether, amine, amide, imide, carbonate, carbamate, squarate, thiazole, thiazolidine, hydrazone, oxime, triazole, and dihydropyridazine; In some embodiments, $L_A$ and $L_B$; and Tag is a tag comprising a negatively-charged polymer moiety which is capable of entering a wide-pore mutant nanopore and upon entering a nanopore in the presence of ions results in an altered flow of the ions through the nanopore.

Exemplary linker forming groups, $X_A$ and $X_B$, linker precursor moieties, $L_A$ and $L_B$ and the resulting linker that they form, of formula -$L_A$-X-$L_B$-, are shown in Table 1, below.

TABLE 1
| $R_1—L_A—X_A$* | $X_B—L_B—R_2$* | $R_1—L_A—X—L_B—R_2$* (or $R_1$—Linker—$R_2$) |
|---|---|---|
| 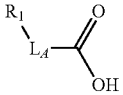 (IVa) |  (IVb) | 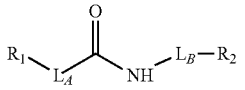 (IVc) |
| 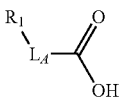 (Va) |  (Vb) | 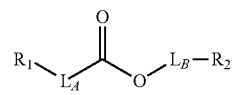 (Vc) |
| 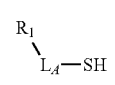 (VIa) | 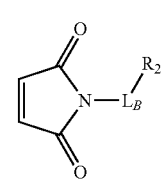 (VIb) | 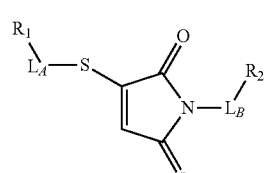 (VIc) |
| 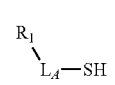 (VIIa) |  (VIIb) wherein, Z is a suitable leaving group, e.g., F, Cl, Br, or I | 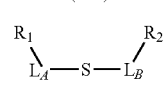 (VIIc) |
| 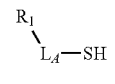 (VIIIa) |  (VIIIb) | 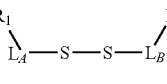 (VIIIc) |
| 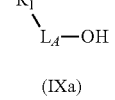 (IXa) |  (IXb) wherein, Z is a suitable leaving group, e.g., F, Cl, Br, or I. | 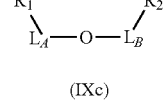 (IXc) |
| 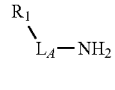 (Xa) |  (Xb) + 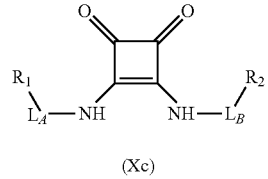 | 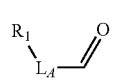 (Xc) |
| 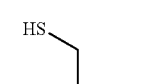 (XIa) | 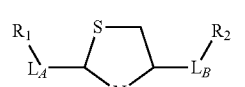 (XIb) | 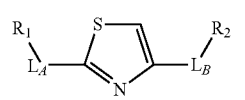 (XIc) |

TABLE 1-continued
| $R_1-L_A-X_A*$ | $X_B-L_B-R_2*$ | $R_1-L_A-X-L_B-R_2*$ (or $R_1$—Linker—$R_2$) |
|---|---|---|
| 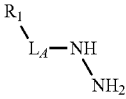 (XIIa) | 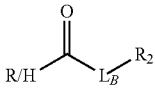 (XIIb) | 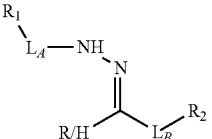 (XIIc) |
| 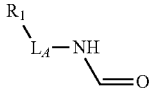 (XIIIa) |  (XIIIb) | 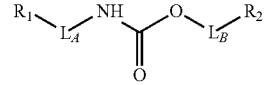 (XIIIc) |
| 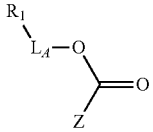 (XIVa) wherein, Z is a suitable leaving group, e.g., —OSu, —OBt, or —OAt |  (XIVb) | 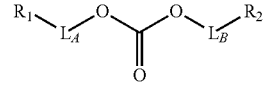 (XIVc) |
|  (XVa) | 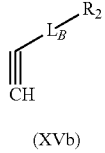 (XVb) | 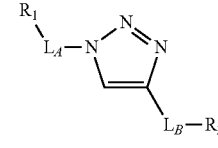 (XVc) |
|  (XVIa) | 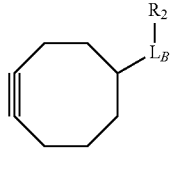 (XVIb) | 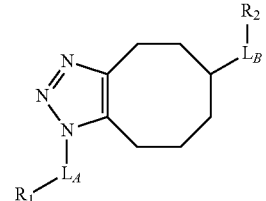 (XVIc) |

TABLE 1-continued

| $R_1$—$L_A$—$X_A$* | $X_B$—$L_B$—$R_2$* | $R_1$—$L_A$—X—$L_B$—$R_2$* (or $R_1$—Linker—$R_2$) |
|---|---|---|
| 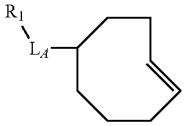 (XVIIa) | 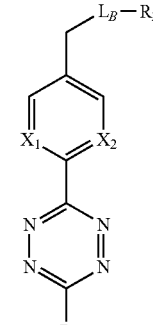 (XVIIb) wherein, $X_1$ and $X_2$ are atoms independently selected from C and N; and $R_3$ is a chemical group selected from the group consisting of: H, F, Cl, Br, I, $CH_3$, $CF_3$, $NH_2$, $NO_2$, OH, C(O)OH, C(O)OCH$_3$, C(O)NH$_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring. | 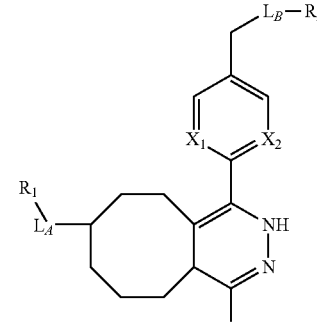 (XVIIc) wherein, $X_1$ and $X_2$ are atoms independently selected from C and N; and $R_3$ is a chemical group selected from the group consisting of: H, F, Cl, Br, I, $CH_3$, $CF_3$, $NH_2$, $NO_2$, OH, C(O)OH, C(O)OCH$_3$, C(O)NH$_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring. |
| 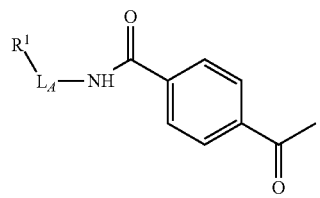 (XVIIIa) | 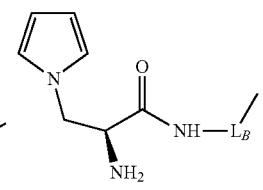 (XVIIIb) | 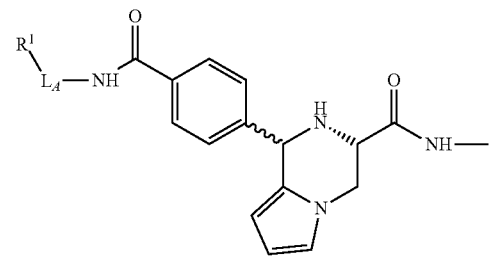 (XVIIIc) |

*$R_1$ and $R_2$ are a tag and nucleoside-5'-oligophosphate, respectively, or $R_1$ and $R_2$ are a nucleoside-5'-oligophosphate and tag, respectively Table 1 exemplifies range of linkers and the corresponding reactive linker-forming groups that undergo a reaction that results in the covalent coupling linker. These various linkers and reactions are well-known in the art. The ordinary artisan will be able to identify the reagents needed for these reactions and either synthesize them or obtain them commercially. For example, reagents for conjugating or cross-linking polypeptide (or proteins) to other biomolecules can be used as linker forming groups to prepare the ion flow altering tagged nucleotide structures of the present disclosure. (See e.g., catalog of "crosslinking reagents" available from Thermo Scientific, USA at www.piercenet.com or Sigma-Aldrich, USA at www.sigmaaldrich.com). Similarly, terminal phosphate modified nucleosides and/or reagents for such modification with azide or alkyne groups (or other linker forming groups) are commercially available (see e.g., Jena Bioscience Gmbh, Jena, Germany). Additionally, a wide range of FMOC-protected amino acid residues modified with azide or alkyne groups (or other linker forming groups) that can be used in the automated solid-phase synthesis of polypeptides are commercially available (see e.g., AnaSpec, Fremont, California, USA).

It is contemplated that any of the pairs of linker forming groups of structural formulae (IVa)-(XVIIIa) and (IVb)-(XVIIIb) can be used in either configuration in preparing a linker useful in a wide-pore ion flow altering tagged nucleotide compounds of the present disclosure (e.g., compound of formula (III)). That is, any of the linker forming groups, $X_A$ and $X_B$ can be used on either the tag or the nucleotide, as long as the linker forming groups are paired to provide the linker reaction forming the linker moiety X. Thus, any of the linker forming groups of structural formulae (IVa)-(XVIIIa) could be attached to either the tag or the nucleotide, and the conjugate linker forming group of structural formulae (IVb)-(XVIIIb) would be attached to the other. Thus, the groups $R_1$ and $R_2$ as depicted in the linkers of form $R_1$-$L_A$-X-$L_B$-$R_2$ in Table 1, can represent either the tag and the nucleotide, or the nucleotide and the tag, respectively. Accordingly, in some embodiments, the present disclosure provides ion flow altering tagged nucleotide compounds of formula (III), wherein the compound comprises a compound of formula $R_1$-$L_A$-X-$L_B$-$R_2$, wherein $R_1$ and $R_2$ are the nucleotide and the tag, or $R_1$ and $R_2$ are the tag and the nucleotide, respectively, and -$L_A$-X-$L_B$- comprises a chemical moiety selected from the moieties of structural formula (IVc)-(XVIIIc) in Table 1.

pound the formula (III) is a linker in formula (XVc) comprising a triazole group X with moieties $L_A$ and $L_B$ on either side resulting in the linker of formula (XVd) shown below.

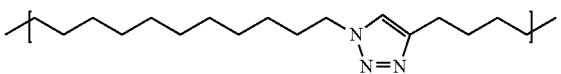

(XVd)

Use of the triazole group as a linker in a tagged nucleotide of the present disclosure provides a wide-pore ion flow altering tagged nucleotide compound of structural formula (IIa) as shown above.

In some embodiments, the linker used in a tagged nucleotide compound the formula (III) is formed via a Pictet-Spengler reaction as shown generally in Scheme 2.

Scheme 2

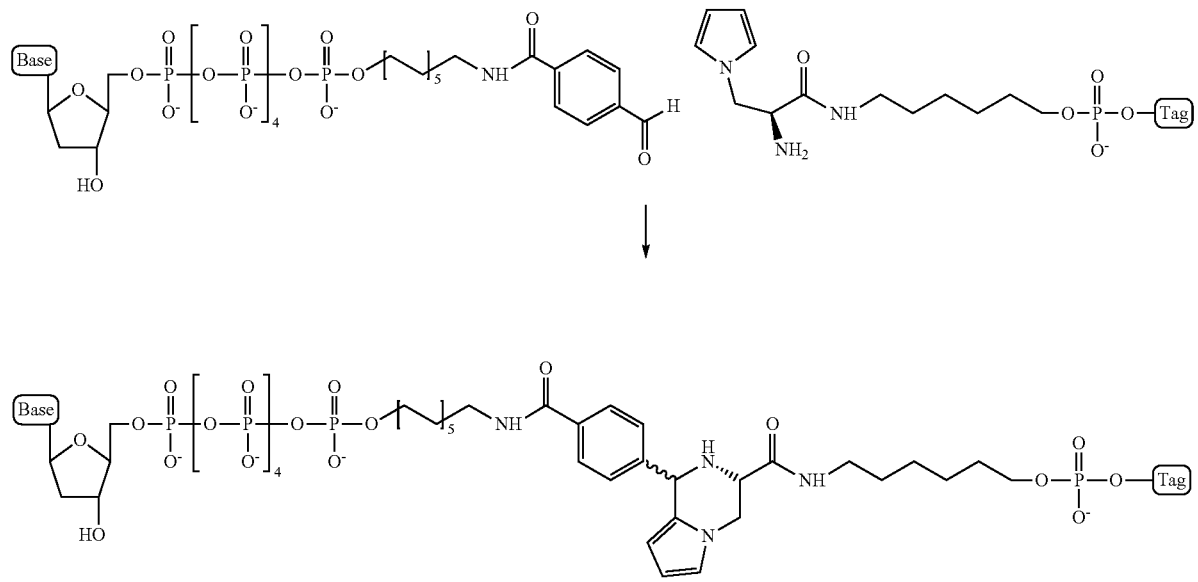

As described above, the chemical moieties $L_A$ and $L_B$ which make up the linker can each independently comprise chemical moieties including linear ($C_1$-$C_{12}$) alkyl, ester, ether, thioether, amine, amide, imide, carbonate, carbamate, polyethylene glycol (PEG), Pictet-Spengler adduct, and combinations thereof. Similar to the linker forming groups $X_A$ and $X_B$, it is contemplated that any of the chemical moieties $L_A$ and $L_B$, which make up the linker, can each independently be used with any of the linker forming groups, and can be used on either the tag or the nucleotide. Additionally, it is contemplated that the chemical moieties $L_A$ and $L_B$ can be the same or different.

In some embodiments, the characteristic linker moiety X is a triazole group. Such a triazole group can be formed in a "click" reaction between an azide linker forming reagent, and an alkyne linker forming reagent. In addition, it is contemplated that a linker in a compound of structural formula (III) comprising a triazole group X can further comprise include a linear alkyl and/or amide groups on one or both sides of the triazole group. Accordingly, in one embodiment, the linker used in a tagged nucleotide com- The use of the Pictet-Spengler reaction as in Scheme 2 also is described in European Pat. Appl. No. EP17166237.2, filed Apr. 17, 2017, which is hereby incorporated by reference herein, and illustrated in further detail in FIG. 1. The linker moiety resulting from the Pictet-Spengler reaction comprises a 1-(4-carbamoylphenyl)-1,2,3,4-tetrahydropyrrolo[1,2-a]pyrazine-3-carboxamide group. This linker moiety referred to herein as a "Pictet-Spengler adduct" is also illustrated in Table 1 as the linker moiety of formula (XVIIIc). Use of the Pictet-Spengler adduct as a linker in a tagged nucleotide of the present disclosure provides a wide-pore ion flow altering tagged nucleotide compound of structural formula (IIb) as shown above.

In some embodiments of the ion flow altering tagged nucleotide compounds of formula (III), the $L_A$ and $L_B$ chemical moieties comprise chemical moieties independently selected from the group consisting of moiety structures of formula (XIXa)-formula (XIXd) as in Table 2.

TABLE 2

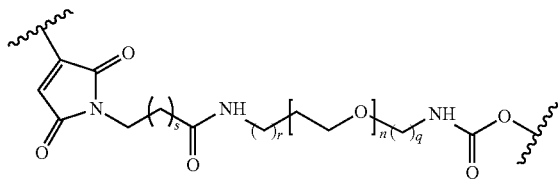

(XIXa)

wherein, n = 1 to 50, and q, r, and s each independently = 0, 1, 2, or 3;

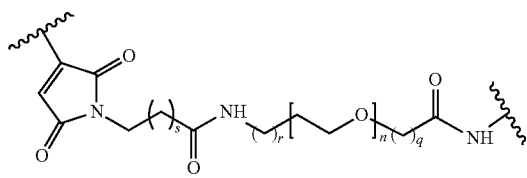

(XIXb)

wherein, n = 1 to 50, and q, r, and s each independently = 0, 1, 2, or 3;

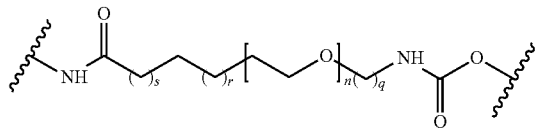

(XIXc)

wherein, n = 1 to 50, and q, r, and s each independently = 0, 1, 2, or 3;

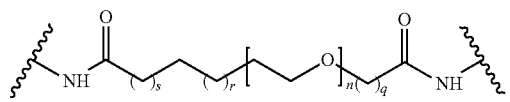

(XIXd)

wherein, n = 1 to 50, and q, r, and s each independently = 0, 1, 2, or 3.

Although Scheme 1 depicts the "-$L_B$-X-$L_A$-" linker that is formed as a moiety separate from the tag, it is contemplated that in some embodiments, the linker can be formed in a reaction with a linker forming group that can comprise part of the tag. For example, the tag can comprise an oligonucleotide wherein the oligonucleotide includes a monomer unit modified with a propargyl or other alkynyl group which can be covalently coupled to a desired nucleotide (or nucleotide analog) via an azide-alkyne "click" reaction. This propargyl group which could also be considered part of the tag can act as a linker forming group (i.e., "$X_B$") and undergoes a linker forming reaction with a linker forming group attached to a nucleotide.

Branched or Dendrimeric Linkers

In addition to the wide range of linkers having two reactive ends capable of covalent coupling to a plurality of molecular moieties, the ion flow altering tagged nucleotides of the present disclosure generally include at least one "branched" or "dendrimeric" linker, which is a type of linker moiety that has three or more reactive ends. The use of linkers comprising a branched or dendrimeric linker moiety facilitate the covalent coupling of a single tag to two or more nucleotides. The use of such linkers in tagged nucleotide compounds with improved properties as polymerase substrates are described in US patent publication 2017/0342485 A1, entitled "Tagged Multi-Nucleotides Useful For Nucleic Acid Sequencing," published Nov. 30, 2017, which is hereby incorporated by reference herein.

Branched or dendrimeric linker moieties capable of providing three or more reactive ends that can be used in the tagged nucleotide compounds of the present disclosure are well-known in the art. See e.g., Shchepinov et al., "Oligonucleotide dendrimers: synthesis and use as polylabelled DNA probes," *Nucleic Acids Research,* 1997, Vol. 25, No. 22, 4447-4454. Branched or dendrimeric linker moieties providing three or more reactive ends useful in the compounds of the present disclosure are commercially available from various vendors of DNA synthesis reagents, e.g., Glen Research (Virginia, USA; www.glenresearch.com).

Accordingly, in some embodiments the ion flow altering tagged nucleotide compounds of the present disclosure can comprise a linker, wherein the linker comprises a branched or dendrimeric moiety capable of forming covalent linkages with three or more molecular moieties.

In some embodiments of the present disclosure, the ion flow altering tagged nucleotide compound comprises a branched or dendrimeric "doubler" linker moiety and has a structural formula (IIIb):

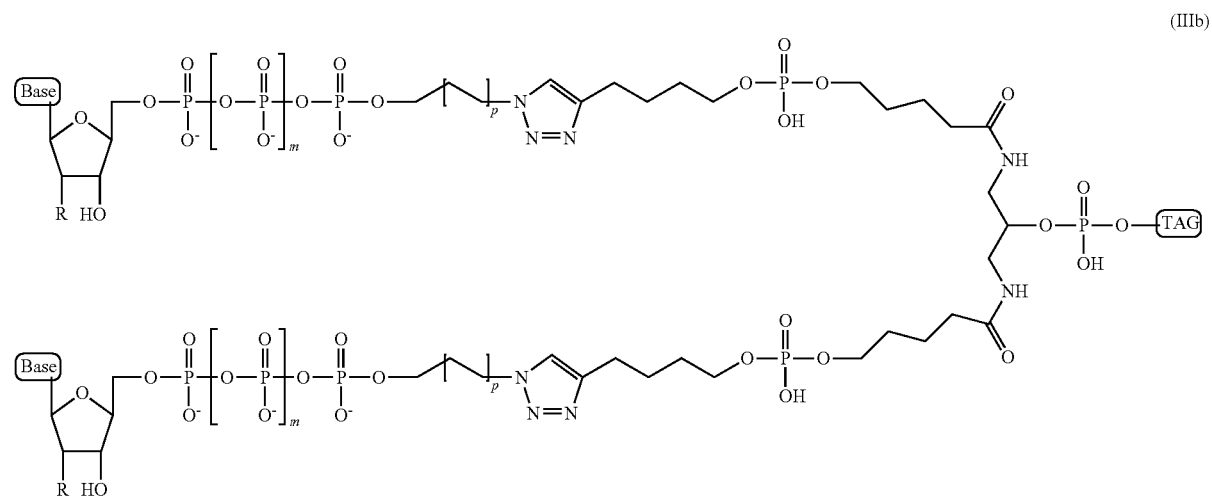

(IIIb)

wherein, "Base" is a naturally occurring or non-naturally occurring nucleobase; R is selected from H and OH; m is from 2 to 12; p is from 2-10; and Tag is a tag comprising a negatively-charged polymer moiety which is capable of entering a nanopore and uponentering a nanopore in the presence of ions results in an altered flow of the ions through the nanopore.

In some embodiments of the present disclosure, the ion flow altering tagged nucleotide compound comprises a branched or dendrimeric "trebler" linker moiety and has a structural formula (IIIc):

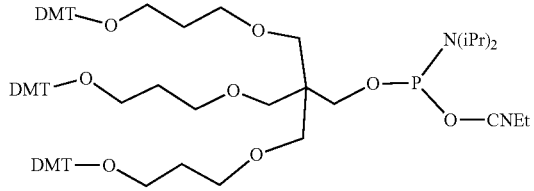
(20)

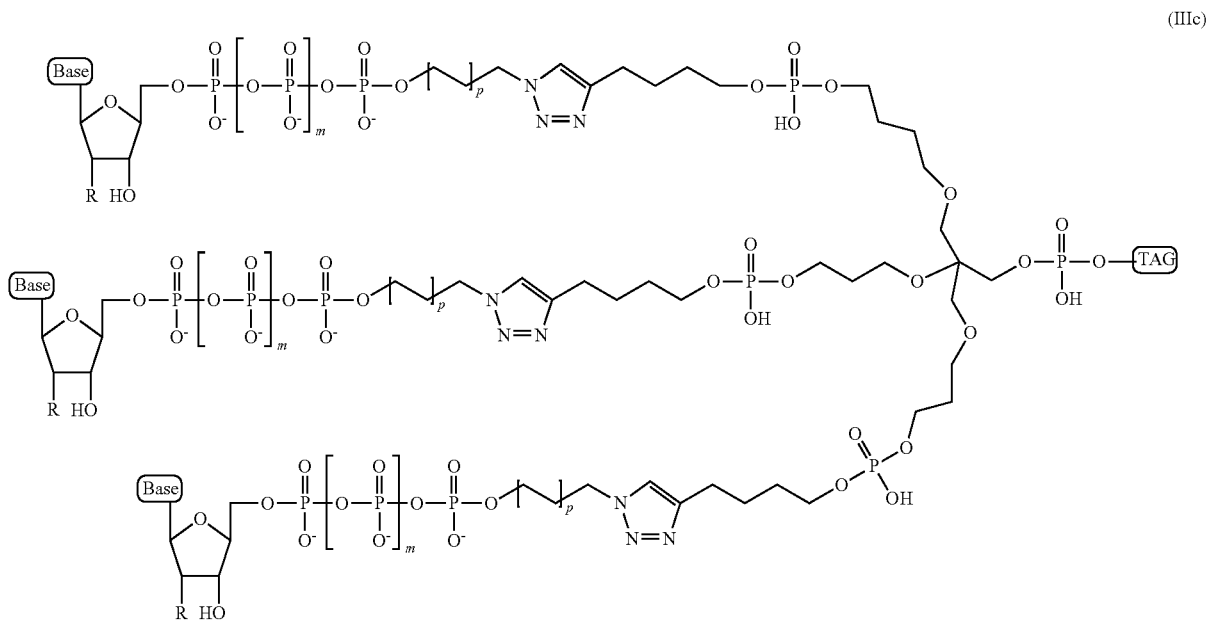
(IIIc)

wherein, "Base" is a naturally occurring or non-naturally occurring nucleobase; R is selected from H and OH; m is from 2 to 12; p is from 2-10; and Tag is a tag comprising a negatively-charged polymer moiety which is capable of entering a nanopore and upon entering a nanopore in the presence of ions results in an altered flow of the ions through the nanopore.

Exemplary reagents useful for preparing ion flow altering tagged nucleotide compound of the present disclosure wherein the linker comprises a branched or dendrimeric moiety include the protected phosphoramidite reagent compounds (19) and (20) shown below.

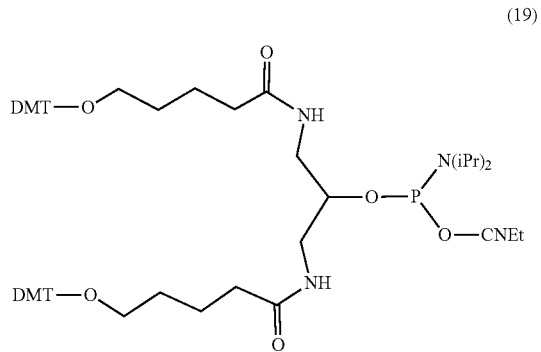
(19)

The branched or dendrimeric phosphoramidite "doubler" and "trebler" units of compounds (19) and (20) are easily attached to the end of oligonucleotide chains to generate a linker end on the oligonucleotide capable of attached 2 or more molecular moieties. Accordingly, an oligonucleotide comprising natural and/or non-natural monomer units can be used as a tag for ion flow altering tagged nucleotide.

Additionally, the branched or dendrimeric phosphoramidite "doubler" unit of compound (19) and the "trebler" unit of compound (20) can be easily combined to create linkers capable of covalent coupling a single molecular moiety (e.g., a tag) to 4, 6, 8, 9, 12, or more nucleotides. For example, a tag can be linked to compound (19) and then compound (20) via standard phosphoramidite synthesis methods to generate compound (21), which is capable of further linking to at least six additional molecular moieties, such as six nucleotides.

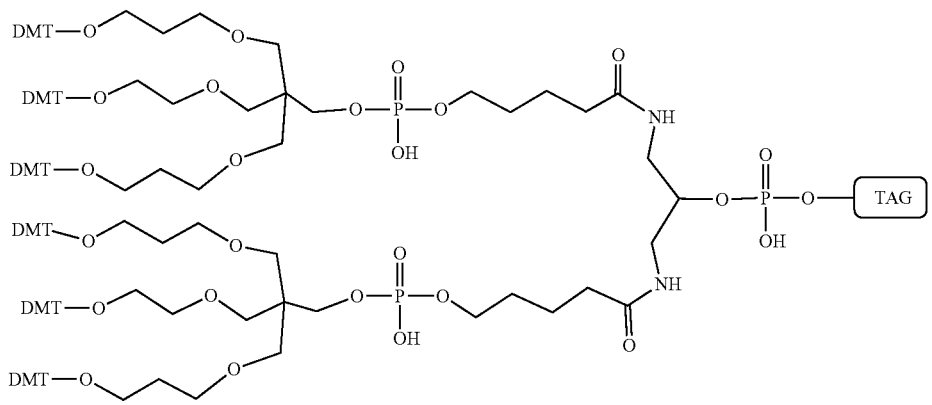

(21)

The three-ended phosphoramidite "doubler" unit of compound (19) can also be prepared (or commercially obtained) with one DMT protecting group and one FMOC protecting group. This "doubler" unit with two different protecting groups can then be used to attach subsequently two different branched or dendrimeric units. For example, a "doubler" unit of compound (19) and a "trebler" unit of compound (20) may be covalently attached in a serial fashion to a "doubler" unit having DMT and Fmoc protecting groups that was previously attached to a single tag. Such a combination provides a single tag with a linker moiety capable of further linking to at least five additional molecular moieties, such as five nucleotides.

The ordinary artisan will immediately recognize that the branched or dendrimeric phosphoramidite units of compounds (19) and (20), or other such branched or dendrimeric linker moieties can be combined in numerous ways to generate ion flow altering tagged nucleotide compounds of the present disclosure.

Wide-Pore Ion Flow Altering Tags

Prior known polymer moieties used as tags for nanopore detection do not alter ion flow through a wide-pore mutant nanopore that results in a measurable reproducible and/or distinctive tag current signal. In contrast, the negatively-charged polymer moieties of structural formula (I) when used as tags rapidly thread into a wide-pore mutant nanopore and causing an altered flow of ions through the nanopore that results in a measurable, reproducible, and distinctive tag current signal. This surprising technical effect of the compounds of the present disclosure allows for the use of wide-pore mutants in nanopore devices thereby providing much longer nanopore lifetimes and longer sequence reads in methods of nanopore SBS.

Generally, the structures of the ion flow altering tags of the present disclosure comprise a nucleoside-5'-oligophosphate moiety covalently linked through the terminal phosphate group of the oligophophate to the 5'-end of a negatively charged polymer moiety of structural formula (I)

$$5'\text{-}[(Sp)_x\text{-}(N)_y\text{-}(Sp)_z]\text{-}[Cap]\text{-}3' \quad (I)$$

wherein, $x=14\text{-}22$; $y=5\text{-}10$; $z=1\text{-}8$; and $x+y+z=27\text{-}35$;

Sp is a monomer unit of formula (1a)

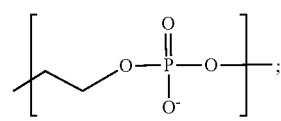
(1a)

N is a unit of formula (2a), (2b), or (2c)

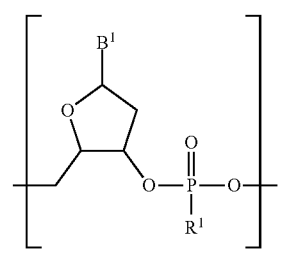
(2a)

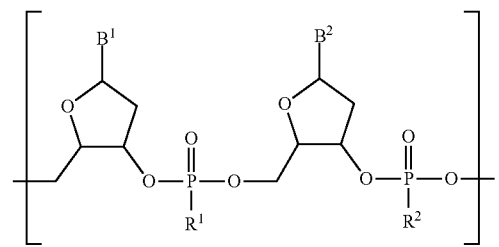
(2b)

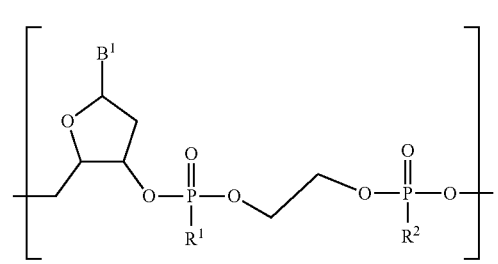
(2c)

wherein, $B^1$ and $B^2$ are independently selected from a natural nucleobase, a modified nucleobase, and H; $R^1$ and $R^2$ are independently selected from $O^-$, $CH_3$, and H; and Cap is a 3'-end capping unit.

As noted elsewhere herein, the negatively-charged polymer moiety structure of formula (I) allows the tag to rapidly thread into (i.e., enter) a wide-pore mutant nanopore and upon entering a nanopore cause an altered flow of the ions through the nanopore resulting a detectable and reproducible tag current signal.

The structural features of the negatively-charged polymer moiety structure of formula (I) are optimized for entering and altering the flow of ions through a wide-pore mutant nanopore. A wide-pore mutant has a constriction site of about 13 angstroms diameter located at a depth of about 65 angstroms as measured from the widest portion of the cis side of the pore when it is embedded in a membrane. The structure of formula (I) is essentially an oligonucleotide of 27-35 monomer units in length with a 3' capping unit.

The oligonucleotide includes a 5' spacer portion, Sp, made up of 14-22 two-carbon SpC2 spacer units of formula (1a). Each of the SpC2 units is relatively narrow, rod-like and have a single negative charge. The overall length of the Sp portion based on the number of SpC2 units, x, provides for the optimal placement of the oligonucleotide's middle portion, the constriction site interacting group, N, in the wide-pore mutant's deeper placed constriction site.

The selection of the type of units of the interacting group N and their optimal placement in the constriction site provides for a detectable and distinctive tag current signal from a wide-pore mutant. The length of the interacting unit N is between 5 and 10 units. The different structures of the constriction site interacting units of formulas (2a), (2b), or (2c), allow for tuning of the desired tag current signal based on the nucleobase and distribution of charge. The structure of the 3' spacer portion is identical to the 5' spacer but with fewer units (5-10). This 3' spacer portion is optimized for rapid threading into the pore and helping to maintain the position of the interacting unit N in the constriction site thereby increasing tag current signal reproducibility.

In various embodiments of the present disclosure, the compounds can include negatively-charged polymer moieties optimized for wide-pore mutant detection by having one or more of the following features: x=14-22; x+y+z=30; the groups $R^1$ and/or $R^2$ are independently selected from $O^-$ and $CH_3$; $B^1$ and/or $B^2$ are independently selected from the group consisting of adenine, cytosine, guanine, thymine, uracil, hypoxanthine, N3CEdT, N3MedT, etheno-dA, 5MedC, 5MedC-PhEt, and dCb; the Cap is a 3'-propanol group; and/or N is a unit of formula (2a). In some embodiments of the compound, the negatively charged polymer moiety has the features x=14-22, y=6-10, z=3-6, x+y+z=30, N is a unit of formula (2a), and Cap is a 3'-propanol group.

In some embodiments of the compound, the constriction site interacting group, N, comprises single phosphate monomer units (i.e., formula (2a)) wherein the nucleobase is a modified nucleobase. Accordingly, in some embodiments, $R^1$ is $O^-$ and $B^1$ is a modified nucleobase. In some embodiments, the modified nucleobase is independently selected from N3CEdT, N3MedT, etheno-dA, 5MedC, 5MedC-PhEt, and dCb.

As noted elsewhere herein, the abbreviations for the modified nucleobases and 3'-capping units are those commonly used for automated oligonucleotide synthesis using commercially available amidite reagents (see e.g., amidite reagent catalogs available from: Glen Research, 22825 Davis Drive, Sterling, VA, USA; or ChemGenes Corp., 33 Industrial Way, Wilmington, MA, USA). Thus, "SpC2" refers to an abasic 2 carbon spacer; "C3" refers to a 3'-propanol; "N3CEdT" refers to the modified nucleobase that results from the 3-N-cyanoethyl-dT amidite (dT with a cyanoethyl group at position N3); "N3MedT" refers to the modified nucleobase that results from the 3-N-methyl-dT amidite (dT with a methyl group at position N3); "5MedC-PhEt" refers to the modified nucleobase that results from the N4-phenylethyl-5-methyl-dC amidite (5-methyl-dC with phenylethyl at position 4 amine); "Etheno-dA" refers to the modified nucleobase that results from the 1,N6-etheno-dA amidite (dA with ethylene linking NI to amine position 6); "dCb" refers to modified nucleobase that results from the N4-(O-Levulinyl-6-oxyhexyl)-5-methyl-dC amidite (5-methyl-dC with O-levulinyl-6-oxyhexyl "brancher" at position 4 amine); "Tmp" refers to a thymidine with methylphosphonate linkage; and "Imp" refers to an inosine with methylphosphonate linkage.

In some embodiments of the compound, the constriction site interacting group, N, comprises a single monomer unit that is a methyl phosphonate monomer unit (e.g., Tmp or Imp). Each of these units are has 1 less negative charge than a phosphate monomer unit and the resulting polymer moiety has a lower overall negative charge, thereby providing distinct tag current levels when present in the wide-pore constriction site. Accordingly, in some embodiment, $R^1$ is $CH_3$ and $B^1$ is thymine or hypoxanthine.

Generally, the overall negative charge of the polymer moiety that is the tag can be varied based on the length and charge distribution over its length. Such parameters can be varied in order to provide a distinct tag current signal. In some embodiments of the tags useful in the compounds of the present disclosure have a negatively-charged polymer moiety with an overall negative charge of from (−20) to (−60), optionally, an overall negative charge of from (−25) to (−50), optionally, an overall negative charge of from (−30) to (−40), or optionally an overall negative charge of from (−31) to (−37).

The compounds of the present disclosure have negative charges distributed regularly along the length of the polymer moiety tag to assist efficient transport of ions through the nanopore. Accordingly, in some embodiments the ion flow altering tags useful in the compounds and tagged nucleotides of the present disclosure, generally comprise a negatively-charged polymer moiety, wherein the negatively-charged polymer moiety has at least one negative charge per 10 angstroms of molecular length, optionally at least one negative charge per 7.5 angstroms of molecular length, or at least one negative charge per 3.5 angstroms of molecular length.

Generally, the negatively-charged polymer moieties because they include the long 5'-spacer portion made up of SpC2 units, adopt a narrow, elongated, rod-like conformation in aqueous solution. The overall polymer length, m, of 27-35 monomer units corresponds to a molecular length capable of approximately spanning the length of the wide-pore mutant nanopore. A standard DNA strand has 3.4 nm (or 34 angstroms) per 10 nucleotides, or a molecular length of about 102 angstroms per 30 nucleotides. The natural nucleotide T has a molecular diameter of about 18 angstroms, whereas the non-natural spacer unit "SpC2" has a narrower molecular diameter of about 10 angstroms (or less).

Accordingly, the negatively-charged polymer moiety of the compounds and tagged nucleotides of the present disclosure has a molecular length of about 90-110 angstroms, and a molecular diameter of about 8 angstroms to about 18 angstroms. In some embodiments, the tagged nucleotides comprise a negatively-charged polymer moiety that has a molecular length of between about 90 angstroms and about 110 angstroms, and an average molecular diameter of about 15 angstroms.

The structures negatively-charged polymer moieties useful as tags in the compounds of the present disclosure generally correspond to oligonucleotide structures. These oligonucleotide structures can be further described in terms of the number and type of its constituent amidite monomer units used in synthesizing the oligonucleotide. Generally, the tags of the present disclosure useful with wide-pore mutants comprise from 27 to 35 monomer units. Accordingly, in some embodiments, the present disclosure provides tagged nucleotide compounds (e.g., compound of structural formula (II)), wherein the negatively-charged polymer moiety comprises an oligonucleotide selected from Table 4.

TABLE 4

| Negatively-Charged Polymer Moiety ("Tag") | Tag SEQ ID NO: |
|---|---|
| -(SpC2)$_{14}$-(N3CEdT)$_{10}$-(SpC2)$_6$-C3 | 1 |
| -(SpC2)$_{14}$-(N3CEdT)$_{10}$-(SpC2)$_{11}$-C3 | 2 |
| -(SpC2)$_{15}$-(N3CEdT)$_7$-(SpC2)$_8$-C3 | 3 |
| -(SpC2)$_{17}$-(N3CEdT)$_{10}$-(SpC2)$_3$-C3 | 4 |
| -(SpC2)$_{19}$-(N3CEdT)$_7$-(SpC2)$_4$-C3 | 5 |
| -(SpC2)$_{22}$-(N3CEdT)$_7$-(SpC2)$_1$-C3 | 6 |
| -(SpC2)$_{27}$-(N3CEdT)$_7$-(SpC2)$_1$-C3 | 7 |
| -(SpC2)$_{14}$-(N3MedT)$_{10}$-(SpC2)$_6$-C3 | 8 |
| -(SpC2)$_{17}$-(dT)$_{10}$-(SpC2)$_3$-C3 | 9 |
| -(SpC2)$_{23}$-(Tmp)$_6$-(SpC2)$_1$-C3 | 10 |
| -(SpC2)$_{20}$-(Tmp)$_6$-(SpC2)$_4$-C3 | 11 |
| -(SpC2)$_{17}$-(Tmp)$_6$-(SpC2)$_7$-C3 | 12 |
| -(SpC2)$_{17}$-(Etheno-dA)$_7$-(SpC2)$_6$-C3 | 13 |
| -(SpC2)$_{22}$-(Etheno-dA)$_7$-(SpC2)$_1$-C3 | 14 |
| -(SpC2)$_{17}$-(Imp)$_7$-(SpC2)$_6$-C3 | 15 |
| -(SpC2)$_{17}$-(dCb)$_7$-(SpC2)$_6$-C3 | 16 |
| -(SpC2)$_{22}$-(dCb)$_7$-(SpC2)$_1$-C3 | 17 |
| -(SpC2)$_{22}$-(dCb)$_7$-(SpC2)$_4$-C3 | 18 |
| -(SpC2)$_{17}$-(dA)$_7$-(SpC2)$_6$-C3 | 19 |
| -(SpC2)$_{22}$-(dA)$_7$-(SpC2)$_1$-C3 | 20 |
| -(SpC2)$_{21}$-(5MedC-PhEt)$_5$-(SpC2)$_4$-C3 | 21 |
| -(SpC2)$_{17}$-(SpC2-dT)$_5$-(SpC2)$_3$-C3 | 22 |
| -(SpC2)$_{17}$-(Tmp-dT)$_5$-(SpC2)$_3$-C3 | 23 |
| -(SpC2)$_{15}$-(N3CEdT-5MedC-PhEt)$_5$-(SpC2)$_5$-C3 | 24 |
| -(SpC2)$_{19}$-(N3CEdT)$_8$-(SpC2)$_3$-C3 | 25 |

Abbreviations are those commonly used for oligonucleotide synthesis:
"SpC2" = abasic 2 carbon spacer (unit of formula (1a));
"C3" = 3'-propanol;
"N3CEdT" = 3-N-cyanoethyl-dT amidite (dT with a cyanoethyl group at position N3);
"N3MedT"-3-N-methyl-dT amidite (dT with a methyl group at position N3);
"5MedC-PhEt" = N4-phenylethyl-5-methyl-dC amidite (5-methyl-dC with phenylethyl at position 4 amine);
"Etheno-dA" = 1,N6-etheno-dA amidite (dA with ethylene linking N1 to amine position 6);
"dCb" = N4-(O-Levulinyl-6-oxyhexyl)-5-methyl-dC amidite (5-methyl-dC with O-levulinyl-6-oxyhexyl "brancher" at position 4 amine);
"Tmp" = thymidine with methylphosphonate linkage;
"Imp" = inosine with methylphosphonate linkage;
"Linker" = triazole linker of formula (XVd) shown below:

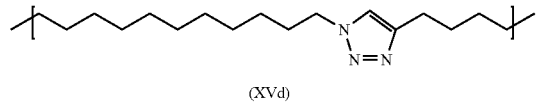

(XVd)

The negatively-charged polymer moieties, like those of Table 4, can be prepared via standard amidite coupling chemistry. The amidite monomer units used to prepare the oligonucleotide tags of Table 4 are available commercially in amidite reagent form (e.g., phosphoramidite or phosphonamidite) (from e.g., Glen Research, 22825 Davis Drive, Sterling, VA, USA). It is contemplated that additional ion flow altering tags can be prepared using such commercially available amidite reagents and standard automated amidite synthesis methods. Further details of the synthesis of the tags of Table 4 are disclosed and exemplified in the Examples.

As noted above, the negatively-charged polymer moiety of formula (I) further comprises a 3'-end capping unit, Cap. Such 3'-end capping units are known to act to protect the 3'-terminus of the tag from digestion in the presence of exonuclease or polymerase enzymes. See e.g., protective 3' end groups as disclosed in WO 2015/148402. Exemplary 3'-end capping units useful in the compounds of the present disclosure include propanol ("C3") and biotin, however, the ordinary artisan will recognize that numerous other 3'-end capping units known in the art are available (e.g., $C_2$-$C_6$ spacers, and H) and can be used for this purpose.

Methods of Preparing Ion Flow Altering Tagged Nucleotides

Standard synthetic methods can be used in preparing the tagged nucleotide compounds of the present disclosure (e.g., compounds of formula (II)). The standard azido-alkyne click reaction described above (e.g., compounds of (XVa) (XVb) forming (XVc)) and in the Examples. Tables 1 and 2 illustrate a range of linkers and linker forming group reactions that can be used in preparing the ion flow altering tagged nucleotides of the present disclosure. In one embodiment, any of the linker forming groups of structural formulas (IVa)-(XVIIIa) shown in Table 1 can be attached to a branched or dendrimeric linker attached to a tag, or to a terminal phosphate of a nucleotide, and the corresponding conjugate linker forming group of structural formulae (IVb)-(XVIIIb) would be attached to other. The resulting covalent linker structures forming the multi-nucleotide-oligophosphate-linker-tag compound are exemplified by structural formulae (IVc)-(XVIIIc) in Table 1.

Accordingly, the present disclosure provides a method of preparing a compound for wide-pore nanopore detection comprising a negatively-charged polymer moiety of formula (I) comprising: (a) providing (i) a nucleotide with from 3 to 6 phosphates attached to its 5'-position, wherein the terminal phosphate is coupled to a first linker forming group (e.g., $X_A$ or $X_B$); and (ii) a wide-pore ion flow altering tag, wherein the tag is coupled to a second linker forming group (e.g., $X_B$ or $X_A$) that is capable of reacting with the first linker forming group to form a linker (e.g., —X—); and (b) reacting the first linker forming group with the second linker forming group to form the ion flow altering tagged nucleotide. First and second linker forming groups that are capable of reacting to form a linker are exemplified in Table 1 above. Thus, in some embodiments of the method, the first linker forming group is selected from the compounds of structural formulas (IVa)-(XVIIIa) and the second linker forming group is the corresponding reactive compound of structural formulas (IVb)-(XVIIIb); or alternatively, the first linker forming group is selected from the compounds of structural formulas (IVb)-(XVIIIb) and the second linker forming group is the corresponding reactive compound of structural formulas (IVa)-(XVIIIa).

In some embodiments, the disclosure provides a method for preparing the wide-pore mutant ion flow altering compound of structural formula (II)

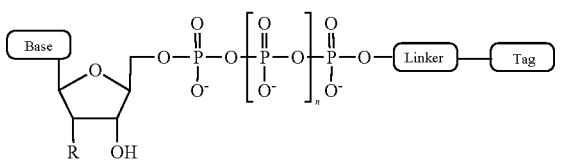

(II)

wherein, "Base" is a nucleobase selected from adenine, cytosine, guanine, thymine, and uracil; R is selected from H and OH; n is from 1 to 4; "Linker" is a linker group comprising a covalently bonded chain of 2 to 100 atoms; and "Tag" is the negatively charged polymer moiety of structural formula (I), wherein the method comprises the steps of:

(a) providing (i) a nucleotide with from 3 to 12 phosphates attached to its 5'-position, wherein the terminal phosphate is coupled to a first linker forming group; and (ii) an ion flow altering tag, wherein the tag comprises a molecular moiety which is capable of producing a detectable signal, comprising at least a second linker forming group capable of reacting with the first linker forming group to form a covalent linker between the nucleotide and the tag; wherein (1) the first linker forming group is selected from the compounds of structural formulas (IVa)-(XVIIIa) and the second linker forming group is the corresponding reactive compound of structural formulas (IVb)-(XVIIIb); or (2) the first linker forming group is selected from the compounds of structural formulas (IVb)-(XVIIIb) and the second linker forming group is the corresponding reactive compound of structural formulas (IVa)-(XVIIIa); and (b) reacting the first linker forming group with the second linker forming group, thereby forming a covalent linkage between the nucleotide and ion flow altering tag.

In some embodiments of the methods of preparing the wide-pore mutant ion flow altering tagged nucleotide compounds of the present disclosure, the first linker forming group attached to the terminal phosphate is an azide group and the second linker forming group attached to the tag is an alkyne. In other embodiments, the first linker forming group attached to the terminal phosphate is an alkyne group and the second linker forming group attached to the tag is an azide.

In some embodiments of the methods, the first linker forming group attached to the terminal phosphate is a tetrazine and the second linker forming group attached to the tag is a trans-cyclooctene. In other embodiments, the first linker forming group attached to the terminal phosphate is a trans-cyclooctene and the second linker forming group attached to the tag is a tetrazine.

As described elsewhere herein, in some embodiments of the methods of preparing the tagged nucleotides of present disclosure, a branched or dendrimeric linker structure can be used to form a multi-nucleotide tagged with a single ion flow altering tag. For example, the linker structure can be generated using the doubler or trebler linker units of compounds (19) or (20). In some embodiments, the doubler or trebler linker units can be linked in a serial fashion to generate branched or dendrimeric linkers have four or more reactive linker forming groups available (e.g., as in compound (21)).

Use of Compounds in Wide-Pore Mutant Nanopore Sequencing

The compounds of the present disclosure useful with wide-pore mutants can be used in any known nanopore sequencing method wherein a wide-pore mutant nanopore detects the presence of a tag attached to a complementary nucleotide as it is incorporated (or after it is incorporated and released) by a strand-extending enzyme (e.g., polymerase, ligase) located proximal to the nanopore and which is extending a primer complementary of a target nucleic acid sequence. General methods, materials, devices, and systems for carrying out nanopore sequencing using tagged nucleotides are described in US Pat. Publ. Nos. 2013/0244340 A1, 2013/0264207 A1, 2014/0134616 A1, 2015/0119259 A1, U.S. Ser. No. 14/666,124, filed Mar. 23, 2015, and U.S. Ser. No. 15/684,726, filed Aug. 23, 2017, each of which is hereby incorporated by reference herein. The wide-pore mutant ion flow altering tagged nucleotides of the present disclosure can be employed in these general methods for using tagged-nucleotides in nanopore sequencing of nucleic acids. Indeed, as illustrated in the Examples herein, the compounds of the present disclosure have improved characteristics for reproducible detection with wide-pore mutants that have much longer lifetimes and thereby provide much longer sequence reads than the corresponding tagged nucleotide compounds not optimized for wide-pore detection.

Thus, in one embodiment, the present disclosure provides a method for determining the sequence of a nucleic acid comprising: (a) providing a nanopore sequencing composition comprising: a membrane, an electrode on the cis side and the trans side of the membrane, a nanopore with its pore extending through the membrane, an electrolyte solution in contact with both electrodes, an active polymerase situated adjacent to the nanopore, and a primer strand complexed with the polymerase; (b) contacting the nanopore sequencing composition with (i) a strand of the nucleic acid; and (ii) a set of compounds each comprising a different nucleoside-5'-oligophosphate moiety covalently linked to a tag, wherein each member of the set of compounds has a different tag which results in a different flow of ions through a nanopore when the tag enters the nanopore, and at least one of the different tags comprises a negatively-charged polymer moiety which upon entering a nanopore in the presence of ions results in an altered flow of the ions through the nanopore; and (c) detecting the different flows of ions resulting from the entry of the different tags in the nanopore over time and correlating to each of the different compounds incorporated by the polymerase which are complementary to the nucleic acid sequence, and thereby determining the nucleic acid sequence.

In some embodiments, the present disclosure provides a method for determining the sequence of a nucleic acid comprising: (a) providing a nanopore sequencing composition comprising: a membrane, an electrode on the cis side and the trans side of the membrane, a nanopore with its pore extending through the membrane, an electrolyte solution in contact with both electrodes, an active polymerase situated adjacent to the nanopore, and a primer strand complexed with the polymerase; (b) contacting the nanopore sequencing composition with (i) a strand of the nucleic acid; and (ii) a set of tagged nucleotides each with a different tag, wherein each different tag causes a different tag current level across the electrodes when it is situated in the nanopore, and the set comprises at least one compound for wide-pore nanopore detection comprising a negatively-charged polymer moiety of formula (I), as described elsewhere herein.

In some embodiments of the method for determining the sequence of a nucleic acid, the set of tagged nucleotides each with a different tag, comprises at least one wide-pore mutant ion flow altering compound of structural formula (II)

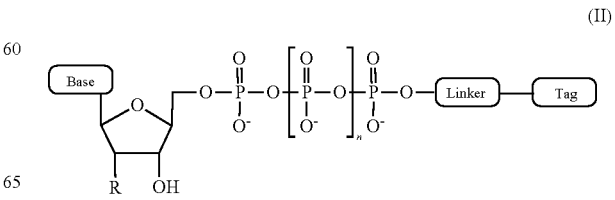

wherein, "Base" is a nucleobase selected from adenine, cytosine, guanine, thymine, and uracil; R is selected from H and OH; n is from 1 to 4; "Linker" is a linker group comprising a covalently bonded chain of 2 to 100 atoms; and "Tag" is the negatively charged polymer moiety of structural formula (I).

When used in the methods for determining the sequence of a nucleic acid the one wide-pore mutant ion flow altering compounds comprising the negatively-charged polymer moiety of formula (I) can include any of the ranges of compound embodiments disclosed elsewhere herein. For example, the compound can be a compound of formula (II) wherein the Tag is selected from Table 4.

Sets of Tagged Nucleotides

As described elsewhere herein, methods for determining the sequence of a nucleic acid using nanopore detection generally require a set of tagged nucleotide compounds each capable of being a substrate for a strand-extending enzyme and each comprising a different tag associated with a nucleotide that is desired to be detected. In standard embodiments for sequencing DNA strands, the method requires a set of at least the four standard deoxy-nucleotides dA, dC, dG, and dT, wherein each different nucleotide is attached to a different tag capable of being detected upon the nucleotide being incorporated by a proximal strand extending enzyme, and furthermore wherein the each tag's nanopore detectable signal (e.g., tag current) is distinguishable from the nanopore detectable signals of each of the other three tags, thereby allowing identification of the specific nucleotide incorporated by the enzyme. Generally, each of the different tagged nucleotides in a set is distinguished by the distinctive detectable tag current signal the tag produces when it is incorporated into a new complementary strand by a strand-extending enzyme. Accordingly, a set of four tagged deoxy-nucleotides dA, dC, dG, and dT is desired that provide well-separated and resolved tag current signals when detected using a wide-pore nanopore device.

In some embodiments, the present disclosure provides a composition comprising a set of tagged nucleotides (e.g., dA, dC, dG, and dT) each with a different tag, wherein each different tag results in a different detectable tag current level upon entering a nanopore of a nanopore device, and wherein the set comprises at least one the set comprises at least one compound for wide-pore nanopore detection comprising a negatively-charged polymer moiety of formula (I), as described elsewhere herein. In some embodiments of the set of tagged nucleotides each with a different tag, the set comprises at least one compound that comprises a structure of formula (II). In some embodiments, the present disclosure the set of four tagged nucleotide compounds (e.g., compound of structural formula (II)), comprises at least one the negatively-charged polymer moiety selected from Table 4.

It is contemplated that the tagged nucleotides of the present disclosure useful with wide-pore mutants may be used in sets of tagged nucleotides that also include tagged nucleotides that do not comprised a negatively charged polymer moiety of structural formula (I), and/or sets with tagged nucleotides having different types of tags, such as both oligonucleotide tags and polypeptide tags. For example, in some embodiments, the set of ion flow altering tagged nucleotides can comprise a wide-pore ion flow altering tagged nucleotide of structural formula (II), and the other tagged nucleotides in the set can comprise nucleotides attached to a negatively-charged polymer that is an oligonucleotide but not of formula (I). (See e.g., US Pat. Publ. Nos. 2013/0244340 A1, 2013/0264207 A1, 2014/0134616 A1, 2015/0119259 A1, U.S. Ser. No. 14/666,124, filed Mar. 23, 2015, and U.S. Ser. No. 15/684,726, filed Aug. 23, 2017, each of which is hereby incorporated by reference herein). Such oligonucleotide-tagged nucleotides that may be able to result in an altered tag current signal from a wide-pore mutant can be used in sets along with the wide-pore optimized tags disclosed herein.

In some embodiments, the set of tagged nucleotides comprises at least two, at least three, or at least four wide-pore ion flow altering tagged nucleotide compounds of structural formula (II) wherein each of the different tags of the at least two, at least three, or at least four of the compounds in the set produces a nanopore detectable signal that is distinguishable from the others in the set.

Three exemplary sets of tagged nucleotides useful in the compositions for wide-pore detection are provided in Table 5 below.

TABLE 5

| Tagged Nucleotide Set | Tag SEQ ID NO: | Avg. Tag Current Level |
|---|---|---|
| Set 1 | | |
| dC6P-(Linker)-T$_2$-(SpC2)$_{28}$-C3 | 34 | 1.15 |
| dA6P-(Linker)-T$_2$-(dSp)$_{26}$-T$_2$-C3 | 35 | 0.85 |
| dT6P-(Linker)-(SpC2)$_{19}$-(N3CEdT)$_7$-(SpC2)$_4$-C3 | 5 | 0.65 |
| dG6P-(Linker)-(SpC2)$_{14}$-(N3CEdT)$_{10}$-(SpC2)$_6$-C3 | 1 | 0.35 |
| Set 2 | | |
| dT6P-(Linker)-(SpC2)$_{22}$-(dA)$_7$-(SpC2)-C3 | 20 | 0.9 |
| dC6P-(Linker)-(SpC2)$_{21}$-(5MedC-PhEt)$_5$-(SpC2)$_4$-C3 | 21 | 0.75 |
| dA6P-(Linker)-(SpC2)$_{22}$-(dCb)$_7$-(SpC2)$_4$-C3 | 18 | 0.6 |
| dG6P-(Linker)-(SpC2)$_{20}$-(Tmp)$_6$-(SpC2)$_4$-C3 | 11 | 0.45 |
| Set 3 | | |
| dC6P-(Linker)-T$_2$-(SpC2)$_{28}$-C3 | 34 | 1.15 |
| dT6P-(Linker)-(SpC2)$_{19}$-(N3CEdT)$_7$-(SpC2)$_4$-C3 | 5 | 0.9 |
| dA6P-(Linker)-(SpC2)$_{17}$-(N3CEdT)$_{10}$-(SpC2)$_3$-C3 | 4 | 0.7 |
| dG6P-(Linker)-(SpC2)$_{15}$-(N3CEdT-5MedC-PhEt)$_5$-(SpC2)$_5$-C3 | 24 | 0.5 |
| Set 4 | | |
| dA6P-(Linker)-(SpC2)$_{14}$-(N3CEdT)$_{10}$-(SpC2)$_6$-C3 | 1 | 0.15 |
| dC6P-(Linker)-T$_2$-(SpC2)$_{28}$-C3 | 34 | 1.15 |
| dG6P-(Linker)-T$_2$-(dSp)$_{26}$-T$_2$-C3 | 35 | 0.80 |
| dT6P-(Linker)-(SpC2)$_{14}$-(N3MedT)$_{10}$-(SpC2)$_6$-C3 | 8 | 0.35 |
| Set 5 | | |
| dA6P-(Linker)-(SpC2)$_{14}$-(N3CEdT)$_{10}$-(SpC2)$_6$-C3 | 1 | 0.15 |
| dC6P-(Linker)-T$_2$-(SpC2)$_{28}$-C3 | 34 | 1.15 |
| dG6P-(Linker)-T$_2$-(dSp)$_{26}$-T$_2$-C3 | 35 | 0.80 |
| dT6P-(Linker)-(SpC2)$_{19}$-(N3CEdT)$_7$-(SpC2)$_4$-C3 | 5 | 0.60 |
| Set 6 | | |
| dA6P-(Linker)-(SpC2)$_{14}$-(N3CEdT)$_{10}$-(SpC2)$_6$-C3 | 1 | 0.15 |
| dC6P-(Linker)-T$_2$-(SpC2)$_{28}$-C3 | 34 | 1.15 |
| dG6P-(Linker)-T$_2$-(dSp)$_{26}$-T$_2$-C3 | 35 | 0.80 |
| dT6P-(Linker)-(SpC2)$_{19}$-(N3CEdT)$_8$-(SpC2)$_3$-C3 | 25 | 0.67 |
| Set 7 | | |
| dA6P-(Linker)-(SpC2)$_{14}$-(N3CEdT)$_{10}$-(SpC2)$_{11}$-C3 | 2 | 0.15 |
| dC6P-(Linker)-T$_2$-(SpC2)$_{28}$-C3 | 34 | 1.15 |
| dG6P-(Linker)-T$_2$-(dSp)$_{26}$-T$_2$-C3 | 35 | 0.80 |
| dT6P-(Linker)-(SpC2)$_{19}$-(N3CEdT)$_8$-(SpC2)$_3$-C3 | 25 | 0.67 |

As shown in Table 5, the average tag current levels determined with wide-pore mutants for each of the four tagged nucleotides in each set are suitably well-separated to allow for good resolution and detection in a nanopore device with wide-pore nanopores. Accordingly, in some embodiments, the present disclosure provides a composition comprising a set of compounds as disclosed herein, wherein the set of compounds is selected from Set 1, Set 2, and Set 3.

Methods and techniques for determining the nanopore detectable signal characteristics, such as tag current level and/or dwell time, are known in the art. (See e.g., US Pat. Publ. Nos. 2013/0244340 A1, 2013/0264207 A1, 2014/0134616 A1, 2015/0119259 A1, U.S. Ser. No. 14/666,124, filed Mar. 23, 2015, and U.S. Ser. No. 15/684,726, filed Aug. 23, 2017, each of which is hereby incorporated by reference herein.) Such methods include nanopore sequencing experiments under AC voltage potentials using a nanopore array as described in the Examples herein.

Nanopore Devices

Nanopore devices and methods for making and using them in nanopore detection applications, such as nanopore sequencing using ion flow altering tagged nucleotides of the present disclosure, are known in the art (See e.g., U.S. Pat. Nos. 7,005,264 B2; 7,846,738; 6,617,113; 6,746,594; 6,673,615; 6,627,067; 6,464,842; 6,362,002; 6,267,872; 6,015,714; 5,795,782; and U.S. Publication Nos. 2015/0119259, 2014/0134616, 2013/0264207, 2013/0244340, 2004/0121525, and 2003/0104428, each of which are hereby incorporated by reference in their entirety). Nanopore devices useful for measuring nanopore detection are also described in the Examples disclosed herein. Generally, the nanopore devices comprise a pore-forming protein embedded in a lipid-bilayer membrane, wherein the membrane is immobilized or attached to a solid substrate which comprises a well or reservoir. The pore of the nanopore extends through the membrane creating a fluidic connection between the cis and trans sides of the membrane. Typically, the solid substrate comprises a material selected from the group consisting of polymer, glass, silicon, and a combination thereof. Additionally, the solid substrate comprises adjacent to the nanopore, a sensor, a sensing circuit, or an electrode coupled to a sensing circuit, optionally, a complementary metal-oxide semiconductor (CMOS), or field effect transistor (FET) circuit. Typically, there are electrodes on the cis and trans sides of the membrane that allow for a DC or AC voltage potential to be set across the membrane which generates a baseline current flow (or O.C. current level) through the pore of the nanopore. The presence of a tag, such as a wide-pore ion flow altering tag of the present disclosure, results in change in positive ion flow through the nanopore and thereby generates a measurable change in current level across the electrodes relative to the O.C. current of the nanopore.

It is contemplated that the ion flow altering tag compounds of the present disclosure can be used with a wide range nanopore devices comprising nanopores generated by both naturally-occurring, and non-naturally occurring (e.g., engineered or recombinant) pore-forming proteins. A wide range of pore-forming proteins are known in the art that can be used to generate nanopores useful for nanopore detection of the ion flow altering tags of the present disclosure. Representative pore forming proteins include, but are not limited to, α-hemolysin, β-hemolysin, γ-hemolysin, aerolysin, cytolysin, leukocidin, melittin, MspA porin and porin A.

The pore-forming protein, α-hemolysin from *Staphylococcus aureus* (also referred to herein as "α-HL"), is one of the most-studied members of the class of pore-forming proteins and has been used extensively in creating nanopore devices. (See e.g., U.S. Publication Nos. 2015/0119259, 2014/0134616, 2013/0264207, and 2013/0244340) α-HL also has been sequenced, cloned, extensively characterized structurally and functionally using a wide range of techniques including site-directed mutagenesis and chemical labelling (see e.g., Valeva et al. (2001), and references cited therein).

The amino acid sequence of the naturally occurring (i.e., wild type) α-HL pore forming protein subunit shown below.

Wild-Type α-HL Amino Acid Sequence (SEQ ID NO: 26)

```
ADSDINIKTG  TTDIGSNTTV  KTGDLVTYDK  ENGMHKKVFY  SFIDDKNHNK  KLLVIRTKGT   60

IAGQYRVYSE  EGANKSGLAW  PSAFKVQLQL  PDNEVAQISD  YYPRNSIDTK  EYMSTLTYGF  120

NGNVTGDDTG  KIGGLIGANV  SIGHTLKYVQ  PDFKTILESP  TDKKVGWKVI  FNNMVNQNWG  180

PYDRDSWNPV  YGNQLFMKTR  NGSMKAADNF  LDPNKASSLL  SSGFSPDFAT  VITMDRKASK  240

QQTNIDVIYE  RVRDDYQLHW  TSTNWKGTNT  KDKWTDRSSE  RYKIDWEKEE  MTNGLSAWSH  300

PQFEK                                                                  305
```

The above wild-type α-HL amino acid sequence is suitable for determining the location of substitutions described herein (and therefore does not include the initial methionine residue typically present upon cloning in *E. coli*). In some embodiments, the wide-pore mutant subunits of α-HL in addition to including the wide-pore mutations are also truncated at amino acid N293, and optionally further include a C-terminal SpyTag peptide fusion and/or His tag as disclosed in WO2017/125565A1, which is hereby incorporated by reference herein, and is further described below.

The amino acid sequence of the α-HL pore forming protein subunit truncated at position N293 shown below.

α-HL Amino Acid Sequence Subunit Truncated at N293 (SEQ ID NO: 27)

```
ADSDINIKTG  TTDIGSNTTV  KTGDLVTYDK  ENGMHKKVFY  SFIDDKNHNK  KLLVIRTKGT   60

IAGQYRVYSE  EGANKSGLAW  PSAFKVQLQL  PDNEVAQISD  YYPRNSIDTK  EYMSTLTYGF  120

NGNVTGDDTG  KIGGLIGANV  SIGHTLKYVQ  PDFKTILESP  TDKKVGWKVI  FNNMVNQNWG  180

PYDRDSWNPV  YGNQLFMKTR  NGSMKAADNF  LDPNKASSLL  SSGFSPDFAT  VITMDRKASK  240

QQTNIDVIYE  RVRDDYQLHW  TSTNWKGTNT  KDKWTDRSSE  RYKIDWEKEE  MTN         293
```

A variety of non-naturally occurring α-HL pore forming proteins have been made including, without limitation, variant α-HL subunits comprising one or more of the following substitutions: H35G, E70K, H144A, E111N, M113A, D127G, D128G, D128K, T129G, K131G, K147N, and V149K. Properties of these various engineered α-HL pore polypeptides are described in e.g., U.S. Published Patent Application Nos. 2017/0088588, 2017/0088890, 2017/0306397, and 2018/0002750, each of which is hereby incorporated by reference herein.

It is contemplated that the tagged nucleotide compounds described herein are particularly useful with nanopore devices having wide-pore mutants of α-HL. As described elsewhere herein, the wide-pore mutants are non-naturally occurring α-HL proteins that are engineered to form a heptameric nanopore having a constriction site of about 13 angstroms diameter located at a depth of about 65 angstroms as measured from the widest portion of the cis side of the pore when it is embedded in a membrane. In some embodiments, the wide-pore mutants comprise α-HL subunits comprising at least amino acid substitutions E111N and M13A. In some embodiments, the wide-pore mutants comprise α-HL subunits comprising the amino acid substitutions E111N and M113A, and further comprising one or more amino acid substitutions selected from D127G, D128G, D128K, T129G, K131G, K147N, and V149K. The 6:1 heptameric subunit compositions of exemplary wide-pore mutants useful with the compounds, compositions, and methods of the present are disclosed below in Table 6.

TABLE 6

| Mutant Identifier | Amino Acid Substitutions (positions relative to wild-type α-HL of SEQ ID NO: 26) |
|---|---|
| P-01 | 6x subunits[1]: (H35G, E111N, M113A, D127G, D128G, T129G, K131G, H144A, K147N, V149K) |
|  | 1x subunit[2]: (E111N, M113A, D127G, D128G, T129G, K131G, K147N) + C-terminal SpyTag peptide fusion |
| P-02 | 6x subunits: (A1K, S3K, H35G, E111N, M113A, D127G, D128G, T129G, K131G, H144A, K147N, V149K) |
|  | 1x subunit: (H35G, E111N, M113A, D127G, D128G, T129G, K131G, K147N) + C-terminal SpyTag peptide fusion |
| P-03 | 6x subunits: (0K, A1K, H35G, E111N, M113A, D127G, D128G, T129G, K131G, H144A, K147N, V149K) |
|  | 1x subunit: wild-type + C-terminal SpyTag peptide fusion |
| P-04 | 6x subunits: (H35G, E111N, M113A, D127G, D128G, T129G, K131G, H144A, K147N, V149K) |
|  | 1x subunit: (H35G, E111N, M113A, D127G, D128G, T129G, K131G, K147N) + C-terminal SpyTag peptide fusion |
| P-05 | 6x subunits: (H35G, E111N, M113A, D127G, D128K, T129G, K131G, H144A, K147N, V149K) |
|  | 1x subunit: (H35G, E111N, M113A, D127G, D128G, T129G, K131G, K147N) + C-terminal SpyTag peptide fusion |
| P-06 | 6x subunits: (D2N, H35G, S106K, E111N, M113A, D127G, D128G, T129G, K131G, H144A, K147N, V149K) |
|  | 1x subunit: (H35G, E111N, M113A, D127G, D128G, T129G, K131G, K147N) + C-terminal SpyTag peptide fusion |
| P-07 | 6x subunits: (H35G, E111N, M113A, D127G, D128K, T129G, K131G, H144A, K147N, V149K, M298A, Ss07d) |
|  | 1x subunit: (H35G, E111N, M113A, D127G, D128G, T129G, K131G, K147N) + C-terminal SpyTag peptide fusion |
| P-08 | 6x subunits: (H35G, E70K, E111N, M113A, D127G, D128K, T129G, K131G, H144A, K147N, V149K) |
|  | 1x subunit: (H35G, E111N, M113A, D127G, D128G, T129G, K131G, K147N) + C-terminal SpyTag peptide fusion |

[1]The "6x subunits" correspond to the α-HL subunits, truncated at position N293, that constitute 6 monomers of the heptameric α-HL nanopore complex.
[2]The "1x subunit" corresponds to the α-HL subunit that constitutes the 1 monomer modified with a C-terminal SpyTag peptide fusion sequence (e.g., at position N293) that allows conjugation to a SpyCatcher protein-modified strand-extending enzyme, such as Pol6.

It is well-known that a heptameric complex of α-HL monomers spontaneously forms a nanopore that embeds in and creates a pore through a lipid bilayer membrane. It has been shown that heptamers of α-HL comprising a ratio of 6:1 native α-HL subunit to mutant α-HL subunit can form nanopores (see e.g., Valeva et al. (2001) "Membrane insertion of the heptameric staphylococcal alpha-toxin pore—A domino-like structural transition that is allosterically modulated by the target cell membrane," J. Biol. Chem. 276(18): 14835-14841, and references cited therein). One α-HL monomer subunit (i.e., "the 1x subunit") of the heptameric pore can be covalently conjugated with a DNA-polymerase using a SpyCatcher/SpyTag conjugation method as described in WO 2015/148402 and WO2017/125565A1, each of which is hereby incorporated by reference herein (see also, Zakeri and Howarth (2010), J. Am. Chem. Soc. 132:4526-7). Briefly, a SpyTag peptide is attached as a recombinant fusion to the C-terminus of the 1x subunit of α-HL, and a SpyCatcher protein fragment is attached as a recombinant fusion to the N-terminus of the strand-extending enzyme, e.g., Pol6 DNA polymerase. The SpyTag peptide and the SpyCatcher protein fragment undergo a reaction between a lysine residue of the SpyCatcher protein and an aspartic acid residue of the SpyTag peptide that results in a covalent linkage conjugating the two the α-HL subunit to the enzyme.

Generally, the wide-pore mutant α-HL subunits are used to prepare heptameric α-HL nanopores with the same methods used with wild-type or other engineered α-HL proteins known in the art. Accordingly, in some embodiments, the compounds of the present disclosure can be used with a nanopore device, wherein the nanopore is a wide-pore mutant. As shown by the exemplary wide-pore mutants of Table 6, the 6:1 heptameric α-HL wide-pore nanopore has six subunits (i.e., the "6x subunits") each having the set of mutations as disclosed in Table 6, and one 1x subunit, which has a slightly different set of mutations as shown in Table 6 (e.g., does not include H144A).

In some embodiments, the 6x subunits are engineered to include a C-terminal fusion comprising the 64 amino acid DNA binding protein 7d of Sulfolobus solfataricus (or "Ss07d"), the sequence of which is described at UniProt entry P39476 (see e.g., at www.uniprot.org/uniprot/P39476; sequence version 2, published Jan. 23, 2007). The Ss07d fusion can act to stabilize the polymerase-template complex of a nearby polymerase for increased processivity.

To facilitate conjugation of a DNA polymerase, the 1x subunit includes a C-terminal fusion (beginning at position 293 or 294 of the truncated wild-type sequence) that includes a SpyTag peptide, e.g., AHIVMVDAYK (SEQ ID NO: 28). The SpyTag peptide allows conjugation of the nanopore to a SpyCatcher-modified strand-extending enzyme, such as a Pol6 DNA polymerase. In some embodiments, the C-terminal SpyTag peptide fusion of the widepore mutants comprises a linker peptide, e.g., GGSSGGSSGG (SEQ ID NO: 29), a SpyTag peptide, e.g., AHIVMVDAYKPTK (SEQ ID NO: 30), and a terminal His tag, e.g., KGHHHHHH (SEQ ID NO: 31). Thus, the C-terminal SpyTag peptide fusion that comprises the amino acid sequence: GGSSGGSSGGAHIVMVDAYKPTKKGHHHHHH (SEQ ID NO: 32). In some embodiments (e.g., those disclosed in Table 6), the C-terminal SpyTag peptide fusion of SEQ ID NO: 32 is attached at position N293 of the 1× subunit which is truncated relative to the wild-type α-HL subunit sequence as in SEQ ID NO: 27). Further details of the preparation and conjugation of a 1× α-HL subunit with a SpyTag peptide fusion of SEQ ID NO: 32 at N293 is described in WO2017125565A1, which is hereby incorporated by reference herein (see e.g., the α-HL subunit with C-terminal SpyTag peptide fusion of SEQ ID NO: 2 disclosed in WO2017125565A1).

Alternatively, an α-HL monomer can be engineered with cysteine residue substitutions inserted at numerous positions allowing for covalent modification of the protein through maleimide linker chemistry (see e.g., Valeva et al. (2001)). For example, the single α-HL subunit can be modified with a K46C mutation which then is easily modified with a linker allowing the use of tetrazine-trans-cyclooctene click chemistry to covalently attach a Bst2.0 variant of DNA polymerase to the heptameric 6:1 nanopore. Such an embodiment is described in U.S. Provisional Application No. 62/130,326, filed Mar. 9, 2015, and U.S. Published Patent Application No. 2017/0175183 A1, each of which is hereby incorporated by reference herein.

Other methods for attaching strand-extending enzymes to nanopores include native chemical ligation (Thapa et al., Molecules 19:14461-14483 [2014]), sortase system (Wu and Guo, J Carbohydr Chem 31:48-66 [2012]; Heck et al., Appl Microbiol Biotechnol 97:461-475 [2013]), transglutaminase systems (Dennler et al., Bioconjug Chem 25:569-578 [2014]), formylglycine linkage (Rashidian et al., Bioconjug Chem 24:1277-1294 [2013]), or other chemical ligation techniques known in the art.

The ion flow altering tagged nucleotides, associated compositions, and methods provided herein can be used with a wide range of strand-extending enzymes such as the polymerases and ligases known in the art.

DNA polymerases are a family of enzymes that use single-stranded DNA as a template to synthesize the complementary DNA strand. DNA polymerases add free nucleotides to the 3' end of a newly-forming strand resulting in extension of the new strand in the 5'-to-3' direction. Most DNA polymerases also possess exonucleolytic activity. For example, many DNA polymerases have 3'-5' exonuclease activity. Such multifunctional DNA polymerases can recognize an incorrectly incorporated nucleotide and use the 3'-5' exonuclease activity to excise the incorrect nucleotide, an activity known as proofreading. Following nucleotide excision, the polymerase can re-insert the correct nucleotide and strand extension can continue. Some DNA polymerases also have 5'-3' exonuclease activity.

DNA polymerases are used in many DNA sequencing technologies, including nanopore-based sequencing-by-synthesis. However, a DNA strand can move rapidly through the nanopore (e.g., at a rate of 1 to 5 s per base), which can make nanopore detecting of each polymerase-catalyzed incorporation event difficult to measure and prone to high background noise, which can result in difficulties in obtaining single-nucleotide resolution. The ability to control the rate of DNA polymerase activity, as well as, increase the signal level from correct incorporation is important during sequencing-by-synthesis, particular when using nanopore detection. As shown in the Examples, the ion flow altering tagged nucleotide compounds of the present disclosure provide for a wider range of detectable tag current signals above the O.C. signal that provide better signal separation and lower noise levels, and thereby allow for more accurate nanopore-based nucleic acid detection and sequencing.

In some embodiments, the polymerase useful with the compounds, compositions, and methods of the present disclosure is a Pol6 DNA polymerase, or a variant of a Pol6, such as an exonuclease deficient Pol6 variant having the mutation D44A, or a Pol6 variant with an increased extension rate having the mutation Y242A and/or E585K. A range of Pol6 DNA polymerase variants having mutations providing polymerase properties useful with the various embodiments of the present disclosure are described in US patent publication nos. 2016/0222363A1, 2016/0333327 A1, 2017/0267983A1, 2018/0094249A1, 2018/0245147A1, each of which is hereby incorporated by reference herein.

Additional exemplary polymerases that may be used with the ion flow altering tagged nucleotide compounds and methods of the present disclosure include the nucleic acid polymerases such as DNA polymerase (e.g., enzyme of class EC 2.7.7.7), RNA polymerase (e.g., enzyme of class EC 2.7.7.6 or EC 2.7.7.48), reverse transcriptase (e.g., enzyme of class EC 2.7.7.49), and DNA ligase (e.g., enzyme of class EC 6.5.1.1).

In some embodiments, the polymerase useful with ion flow altering tagged nucleotides is 9° N polymerase, E. coli DNA Polymerase I, Bacteriophage T4 DNA polymerase, Sequenase, Taq DNA polymerase, 9° N polymerase (exo-) A485L/Y409V or Phi29 DNA polymerase (Ø29 DNA Polymerase).

In some embodiments, the strand extending enzyme that incorporates the ion flow altering tagged nucleotides comprises a DNA polymerase from *Bacillus stearothermophilus*. In some embodiments, the large fragment of DNA polymerase from *B. stearothermophilus*. In one embodiment, the polymerase is DNA polymerase Bst 2.0 (commercially available from New England BioLabs, Inc., Massachusetts, USA).

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Preparation of Tagged Nucleoside Compounds of Formula (II)

This example illustrates a general method for preparation of a tagged nucleoside compound of structural formula (II), wherein the compound comprises a nucleoside-5'-hexaphosphate with its terminal phosphate group attached to the 5' end of oligonucleotide tag through a triazole linker formed via a Cu-catalyzed azido-alkyne click-chemistry reaction. More specifically, this example describes the preparation of the tagged nucleotide compounds shown below in Table 7.

TABLE 7

| Tagged Nucleotide | Tag SEQ ID NO: |
|---|---|
| dT6P-(Linker)-(SpC2)$_{19}$-(N3CEdT)$_7$-(SpC2)$_4$-C3 | 5 |
| dT6P-(Linker)-(SpC2)$_{15}$-(N3CEdT)$_7$-(SpC2)$_8$-C3 | 3 |
| dT6P-(Linker)-(SpC2)$_{22}$-(N3CEdT)$_7$-(SpC2)$_1$-C3 | 6 |
| dT6P-(Linker)-(SpC2)$_{27}$-(N3CEdT)$_7$-(SpC2)$_1$-C3 | 7 |
| dT6P-(Linker)-(SpC2)$_{17}$-(N3CEdT)$_{10}$-(SpC2)$_3$-C3 | 4 |
| dT6P-(Linker)-(SpC2)$_{19}$-(N3CEdT)$_8$-(SpC2)$_3$-C3 | 25 |
| dT6P-(Linker)-(SpC2)$_{14}$-(N3MedT)$_{10}$-(SpC2)$_6$-C3 | 8 |
| dT6P-(Linker)-(SpC2)$_{17}$-(dT)$_{10}$-(SpC2)$_3$-C3 | 9 |
| dT6P-(Linker)-(SpC2)$_{17}$-(SpC2-dT)$_5$-(SpC2)$_3$-C3 | 22 |
| dT6P-(Linker)-(SpC2)$_{17}$-(Tmp-dT)$_5$-(SpC2)$_3$-C3 | 23 |
| dT6P-(Linker)-(SpC2)$_{23}$-(Tmp)$_6$-(SpC2)$_1$-C3 | 10 |
| dT6P-(Linker)-(SpC2)$_{20}$-(Tmp)$_6$-(SpC2)$_4$-C3 | 11 |
| dT6P-(Linker)-(SpC2)$_{17}$-(Tmp)$_6$-(SpC2)$_7$-C3 | 12 |
| dT6P-(Linker)-(SpC2)$_{17}$-(Etheno-dA)$_7$-(SpC2)$_6$-C3 | 13 |
| dT6P-(Linker)-(SpC2)$_{22}$-(Etheno-dA)$_7$-(SpC2)$_1$-C3 | 14 |
| dT6P-(Linker)-(SpC2)$_{17}$-(Imp)$_7$-(SpC2)$_6$-C3 | 15 |
| dT6P-(Linker)-(SpC2)$_{17}$-(dCb)$_7$-(SpC2)$_6$-C3 | 16 |
| dT6P-(Linker)-(SpC2)$_{22}$-(dCb)$_7$-(SpC2)$_1$-C3 | 17 |
| dT6P-(Linker)-(SpC2)$_{17}$-(dA)$_7$-(SpC2)$_6$-C3 | 19 |
| dT6P-(Linker)-(SpC2)$_{22}$-(dA)$_7$-(SpC2)$_1$-C3 | 20 |
| dG6P-(Linker)-(SpC2)$_{14}$-(N3CEdT)$_{10}$-(SpC2)$_6$-C3 | 8 |
| dA6P-(Linker)-(SpC2)$_{14}$-(N3CEdT)$_{10}$-(SpC2)$_6$-C3 | 8 |
| dA6P-(Linker)-(SpC2)$_{14}$-(N3CEdT)$_{10}$-(SpC2)$_{11}$-C3 | 2 |
| dC6P-(Linker)-(SpC2)$_{21}$-(5MedC-PhEt)$_5$-(SpC2)$_4$-C3 | 21 |
| dA6P-(Linker)-(SpC2)$_{22}$-(dCb)$_7$-(SpC2)$_4$-C3 | 18 |
| dG6P-(Linker)-(SpC2)$_{20}$-(Tmp)$_6$-(SpC2)$_4$-C3 | 11 |
| dA6P-(Linker)-(SpC2)$_{17}$-(N3CEdT)$_{10}$-(SpC2)$_3$-C3 | 4 |
| dG6P-(Linker)-(SpC2)$_{15}$-(N3CEdT-5MedC-PhEt)$_5$-(SpC2)$_5$-C3 | 24 |

Abbreviations are those commonly used for oligonucleotide synthesis:
"SpC2" = abasic 2 carbon spacer;
"C3" = 3'-propanol;
"N3CEdT" = 3-N-cyanoethyl-dT amidite (dT with a cyanoethyl group at position N3);
"N3MedT" = 3-N-methyl-dT amidite (dT with a methyl group at position N3);
"5MedC-PhEt" = N4-phenylethyl-5-methyl-dC amidite (5-methyl-dC with phenylethyl at position 4 amine);
"Etheno-dA" = 1,N6-etheno-dA amidite (dA with ethylene linking N1 to amine position 6);
"dCb" = N4-(O-Levulinyl-6-oxyhexyl)-5-methyl-dC amidite (5-methyl-dC with O-levulinyl-6-oxyhexyl "brancher" at position 4 amine);
"Tmp" = thymidine with methylphosphonate linkage;
"Imp" = inosine with methylphosphonate linkage;
"Linker" = triazole linker of formula (XVd) shown below:

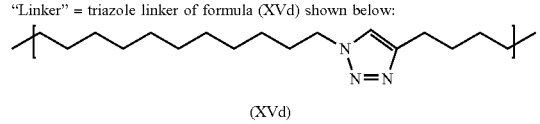

(XVd)

The synthesis method uses a standard Cu catalyzed azido-alkyne click reaction to covalently couple the 5'-end of a tag that is an oligonucleotide to the terminal phosphate group of the nucleotide hexaphosphate (dN6P) as shown generally in Scheme 3 below.

Scheme 3

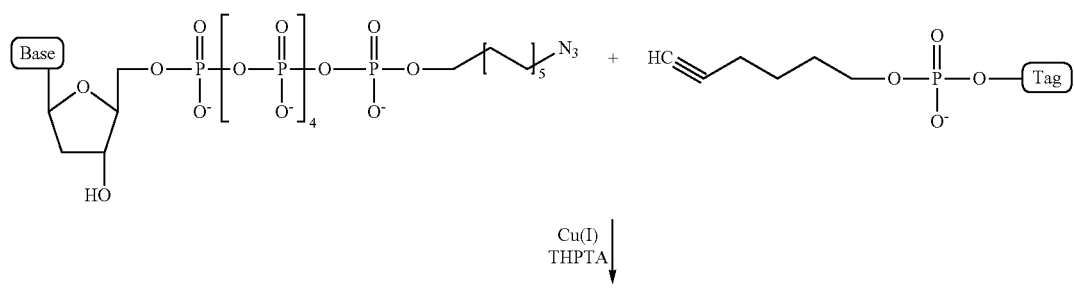

Cu(I)
THPTA

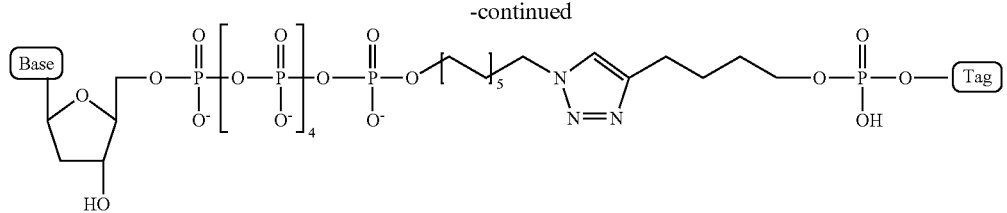

The synthesis method of Scheme 3 is described in further detail below for the preparation of the specific tagged nucleotide, dT6P-(Linker)-(SpC2)$_{19}$-(N3CEdT)$_7$-(SpC2)$_4$-C3 (i.e., compound of formula (II), where Base is T and Tag is the oligonucleotide, -(SpC2)$_{19}$-(N3CEdT)$_7$-(SpC2)$_4$-C3 (SEQ ID NO: 5). This same method is used to prepare the other tagged nucleotides listed above in Table 7.

A. Synthesis dT6P-azide (Compound (1))

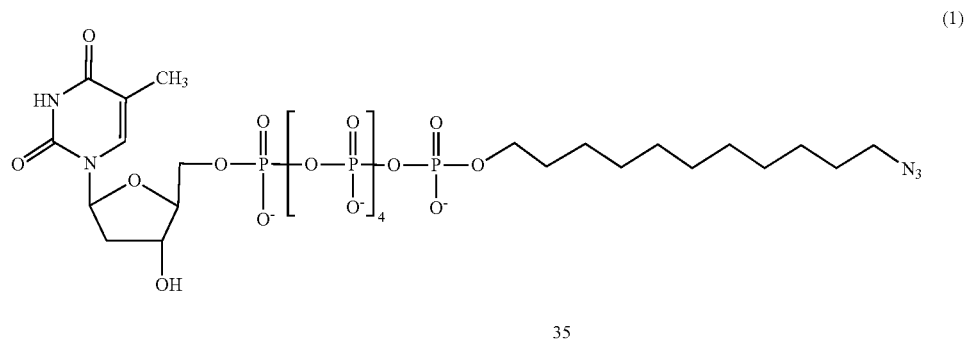

(1)

Preparation of 11-azido-1-undecanol 11-azido-1-undecanol is prepared according to the reaction Scheme 4 and procedure below.

Scheme 4

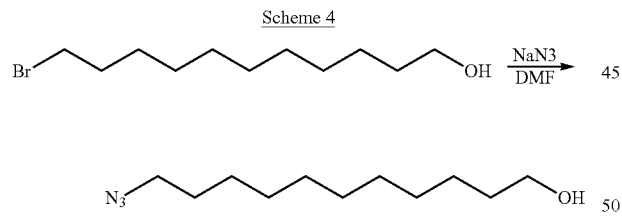

In a dried round bottom flask, sodium azide (1.44 g, 22 mM) was added to a solution of 11-Bromo-1-undecanol (1.84 g, 7.38 mmol) in anhydrous DMF (40 mL). The resulting white suspension was stirred under nitrogen atmosphere at ambient temperature overnight. The suspension was filtered and rinsed with DCM (50 mL). The solution was concentrated under vacuum to give yellowish oil. The compound can be used in the following steps without further purification.

Preparation of 11-azido-1-undecanyl triphosphate 11-azido-1-undecanyl triphosphate is prepared according to the reaction Scheme 5 and procedure below.

Scheme 5

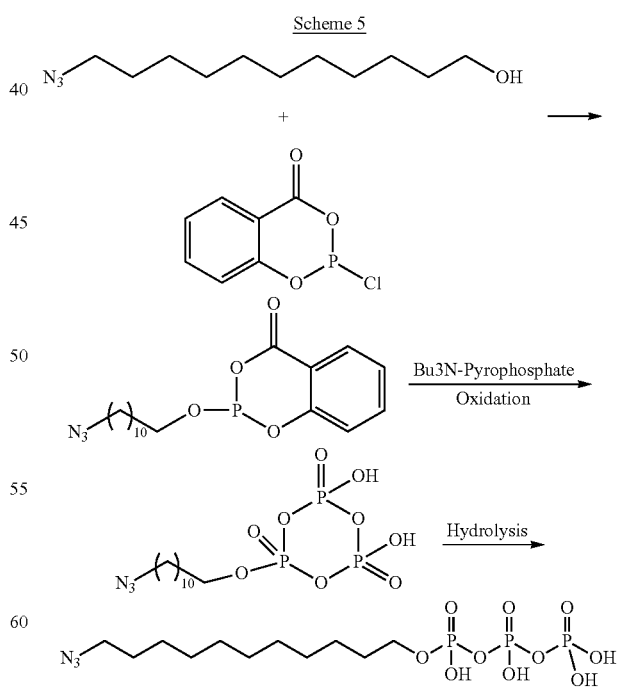

In a dried round bottom flask, 11-azido-1-undecanol (0.20 g, 0.94 mmol) was dissolved in anhydrous DMF (2.0 mL). Salicyl chlorophosphite (0.20 g, 1.03 mmol) was added in one portion. The resulting solution was stirred at ambient temperature under nitrogen for 45 minutes. In another flask, a solution of pyrophosphate tributylamine (0.566, 1.03 mmol) in anhydrous DMF and tributylamine (1.39 g, 7.51 mmol) was prepared and then added to the reaction solution. The resulting mixture was stirred for an hour and was oxidized with 20 mM iodine solution (80 mL, 1.55 mmol), giving cyclic meta-triphosphate intermediate that can be analyzed by mass spectrometer. After another hour of stirring, the reaction was quenched first with $Na_2SO_3$ (10%, 4 mL), allowed to stir for 20 minutes, followed by TEAB (0.10 M, 20 mL). The resulting mixture was stirred at ambient temperature overnight. The crude product was purified by TeleDyne CombiFlash RF+ column system using 30 g HP C18 column eluting with $CH_3CN$/0.1 TEAA (0% to 50% $CH_3CN$ in 16 minutes). The product is concentrated under vacuum and dried on a lyophilizer.

Preparation of dT6P-azide (Compound (1))

dT6P-azide is prepared according to the reaction Scheme 6 and procedure below.

formation of the compound (1) was confirmed by mass spectrometry (cal. 917.06, observed 916.03 for negative ion).

B. Synthesis of 5'-propargyl-$(SpC2)_{19}$-$(N3CEdT)_7$-$(SpC2)_4$-C3 Oligonucleotide (Compound (2))

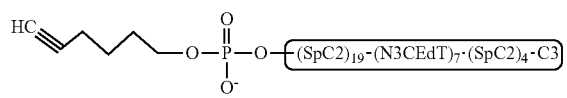

The 5'-propargyl-$(SpC2)_{19}$-$(N3CEdT)_7$-$(SpC2)_4$-C3 oligonucleotide used to prepare the negatively-charged polymer moiety (i.e., "Tag" of formula (II)) was synthesized on an ABI 3900 DNA Synthesizer using standard solid phase phosphoramidite chemistry protocols and commercially available reagents, including the abasic 2 carbon spacer amidite, SpC2, the N3-cyano-modified dT amidite, Scheme 6

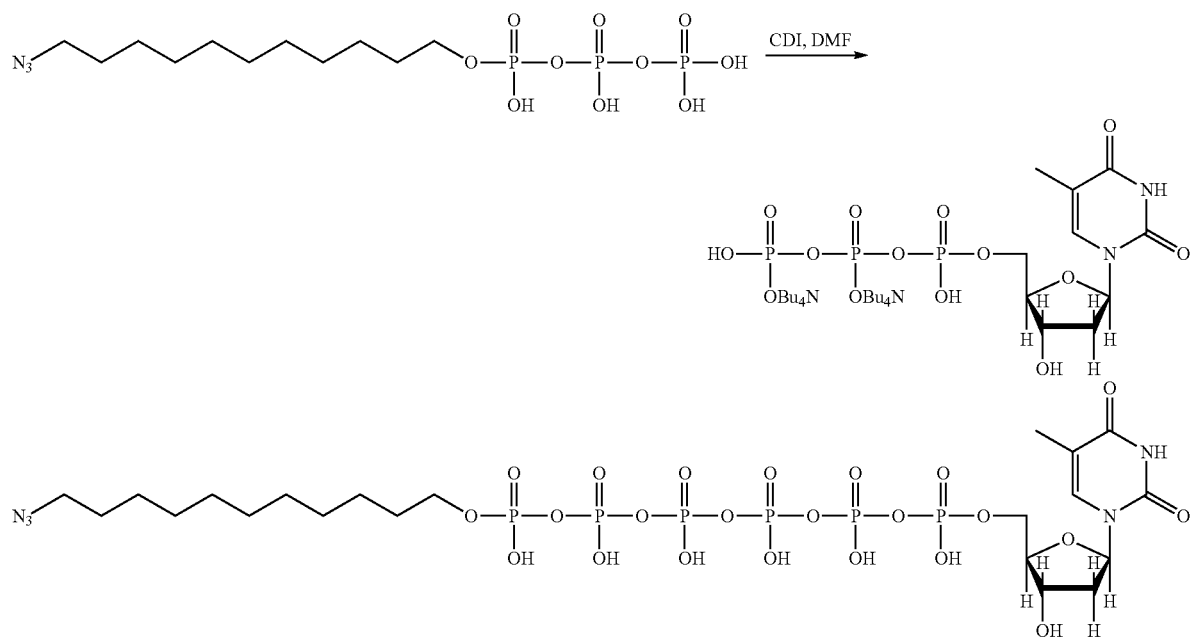

11-azido-1-undecanyl triphosphate (0.091 g, 0.12 mmol) was dissolved in anhydrous DMF (1.5 mL) and was activated with carbonyl diimidazole ("CDI") (0.078 g, 0.48 mmol) for 4 hours at ambient temperature. The excess CDI was quenched with methanol (0.029 mL, 0.72 mmol), stirring additional 30 minutes. Then a solution of dTTP+3Bu$_4$N (0.20 g, 0.17 mmol) in anhydrous DMF (2.0 mL) was added, followed by $MgCl_2$ (0.114 g, 1.20 mmol). The resulting slurry solution was stirred for 24-36 hours at ambient temperature. The reaction was quenched with TEAB 0.1 M (20 mL), stirring for 30 minutes. The crude compound (1) was purified by ion-exchange chromatography (0.1 M to 1 M in 30 minutes), followed by RP-C18 HPLC (10-45% $CH_3CN$ in 35 minutes) to yield 15-30 µmol of product. The N3CEdT, and the 5'-hexynyl amidite reagents (available from e.g., Glen Research, 22825 Davis Drive, Sterling, VA, USA, or ChemGenes Corp., 33 Industrial Way, Wilmington, MA, USA). In the final automated oligonucleotide synthesis step 5'-hexynyl amidite was added to the 5' phosphate of the SpC2 spacer resulting in the propargyl-modified oligonucleotide of compound (2).

C. Click-Reaction to Form Tagged Nucleotide, dT6P-(Linker)-$(SpC2)_{19}$-$(N3CEdT)_7$-$(SpC2)_4$-C3

The click reaction forming tagged nucleotide compound, dT6P-(Linker)-$(SpC2)_{19}$-$(N3CEdT)_7$-$(SpC2)_4$-C3 is carried out according to the reaction of Scheme 3 and the following procedures. In a 2 mL reaction vial, 200 nmol of the 5'-propargyl-$(SpC2)_{19}$-$(N3CEdT)_7$-$(SpC2)_4$-C3 oligonucleotide (compound (2)) is added followed by 40 µL of a 0.10 M solution of THPTA ligand in water and 30 µL of a 0.10 M solution of CuBr in 3:1 DMSO:tBuOH to afford a blue solution. The dT6P-azide is added (compound (1)) (9.2 µL of a 37.9 mM solution=350 nmol) and the resulting solution is allowed to incubate on a thermomixer at 800 rpm, 25 degrees C. for 16 hours. Upon completion, the reaction is filtered through a 0.2 µm syringe filter and purified by reverse phase C18 HPLC using a gradient elution of acetonitrile in 0.10 M triethylammonium acetate, pH 7.5 (5% acetonitrile to 20% acetonitrile over 35 minutes). Product containing fractions are confirmed by mass spectrometry (observed molecular weight 6507.4, calculated 6507.2), combined, diluted with 3 µL of 1.0 M HEPES buffer pH 7.5 and lyophilized to dryness. The resulting product (136 nmol) is resuspended in dionized water and assayed by analytical HPLC-MS (>99% calculated purity, MW obs'd 6507.4, calc'd 6507.2).

Synthesis of the other tagged nucleotides of Table 7 were confirmed by mass spectrometry as shown in Table 8 below.

TABLE 8

| Tagged Nucleotide | Tag SEQ ID NO: | MW Calc/Obsd |
|---|---|---|
| dT6P-(Linker)-(SpC2)$_{19}$-(N3CEdT)$_7$-(SpC2)$_4$-C3 | 5 | 6507.2/6507.4 |
| dT6P-(Linker)-(SpC2)$_{15}$-(N3CEdT)$_7$-(SpC2)$_8$-C3 | 5 | 6507.2/6507.4 |
| dT6P-(Linker)-(SpC2)$_{22}$-(N3CEdT)$_7$-(SpC2)$_1$-C3 | 6 | 6507.2/6507.4 |
| dT6P-(Linker)-(SpC2)$_{27}$-(N3CEdT)$_7$-(SpC2)$_1$-C3 | 7 | 7127.3/7127.4 |
| dT6P-(Linker)-(SpC2)$_{17}$-(N3CEdT)$_{10}$-(SpC2)$_3$-C3 | 4 | 7206.8/7207.0 |
| dT6P-(Linker)-(SpC2)$_{17}$-(SpC2-dT)$_5$-(SpC2)$_3$-C3 | 22 | 5775.4/5775.4 |
| dT6P-(Linker)-(SpC2)$_{17}$-(Tmp-dT)$_5$-(SpC2)$_3$-C3 | 23 | 6666.3/6666.4 |
| dT6P-(Linker)-(SpC2)$_{23}$-(Tmp)$_6$-(SpC2)$_1$-C3 | 10 | 5943.7/5943.6 |
| dT6P-(Linker)-(SpC2)$_{20}$-(Tmp)$_6$-(SpC2)$_4$-C3 | 11 | 5943.7/5943.6 |
| dT6P-(Linker)-(SpC2)$_{17}$-(Tmp)$_6$-(SpC2)$_7$-C3 | 12 | 5943.7/5943.6 |
| dT6P-(Linker)-(SpC2)$_{17}$-(Etheno-dA)$_7$-(SpC2)$_6$-C3 | 13 | 6367.0/6367.5 |
| dT6P-(Linker)-(SpC2)$_{22}$-(Etheno-dA)$_7$-(SpC2)$_1$-C3 | 14 | 6367.0/6367.5 |
| dT6P-(Linker)-(SpC2)$_{17}$-(Imp)$_7$-(SpC2)$_6$-C3 | 15 | 6191.9/6192.5 |
| dT6P-(Linker)-(SpC2)$_{17}$-(dCb)$_7$-(SpC2)$_6$-C3 | 16 | 6830.0/6830.0 |
| dT6P-(Linker)-(SpC2)$_{22}$-(dCb)$_7$-(SpC2)$_1$-C3 | 17 | 6830.0/6830.0 |
| dT6P-(Linker)-(SpC2)$_{17}$-(dA)$_7$-(SpC2)$_6$-C3 | 19 | 6198.8/6199.4 |
| dT6P-(Linker)-(SpC2)$_{22}$-(dA)$_7$-(SpC2)$_1$-C3 | 20 | 6198.8/6199.4 |
| dG6P-(Linker)-(SpC2)$_{14}$-(N3CEdT)$_{10}$-(SpC2)$_6$-C3 | 1 | 7231.9/7231.9 |
| dA6P-(Linker)-(SpC2)$_{22}$-(dCb)$_7$-(SpC2)$_4$-C3 | 18 | 7211.1/7211.1 |
| dG6P-(Linker)-(SpC2)$_{20}$-(Tmp)$_6$-(SpC2)$_4$-C3 | 11 | 6532.3/6532.3 |
| dA6P-(Linker)-(SpC2)$_{17}$-(N3CEdT)$_{10}$-(SpC2)$_3$-C3 | 4 | 7216.0/7215.9 |
| dG6P-(Linker)-(SpC2)$_{15}$-(N3CEdT-5MedC-PhEt)$_5$-(SpC2)$_5$-C3 | 24 | 7409.0/7412.1 |
| dA6P-(Linker)-(SpC2)$_{14}$-(N3CEdT)$_{10}$-(SpC2)$_6$-C3 | 1 | 7216.0/7216.0 |
| dA6P-(Linker)-(SpC2)$_{14}$-(N3CEdT)$_{10}$-(SpC2)$_{11}$-C3 | 2 | 7827.0/7827.0 |
| dT6P-(Linker)-(SpC2)$_{14}$-(N3MedT)$_{10}$-(SpC2)$_6$-C3 | 8 | 6816.0/6816.6 |
| dT6P-(Linker)-(SpC2)$_{19}$-(N3CEdT)$_8$-(SpC2)$_3$-C3 | 25 | 6740.0/6740.7 |

Example 2: Detection of the Tagged Nucleoside Compounds of Formula (II) with a Wide-Pore Mutant Nanopore Device This example illustrates detection of the tagged nucleoside compounds of structural formula (II) (prepared as described Example 1) using a Pol6 polymerase-linked wide-pore mutant nanopore device. The results demonstrate the improved tag current signal characteristics exhibited by the tagged nucleoside compounds of formula (II) when used with wide-pore mutant nanopore devices for which they have been optimized.

Briefly, the nanopore detection of the tagged nucleotides is carried out using an array of wide-pore mutant α-HL nanopores, as described elsewhere herein, each conjugated to a Pol6 polymerase variant, such as an exonuclease deficient Pol6 variant with increased extension rate, as described in US patent publication nos. 2016/0222363A1, 2016/0333327 A1, 2017/0267983A1, 2018/0094249A1, 2018/0245147A1. The α-HL-Pol6 wide-pore mutant nanopore conjugates are embedded in membranes formed over an array of individually addressable integrated circuit chips. This nanopore device is exposed to a DNA template, and at least one tagged nucleoside substrate from those listed in Table 7. In one set of experiments (see Table 9 below) only one tagged dT6P nucleoside was used, the remaining three nucleotide hexaphosphate substrates (i.e., dA6P, dC6P, and dG6P) without tags. In another set of experiments (see Table 10 below), sets of four tagged nucleoside representing four different dN6P substrates (i.e., tagged nucleosides for each of dA6P, dC6P, dG6P, and dT6P) were used. In both experiments, the tagged nucleotide that is complementary to the DNA template is captured and bound to the Pol6 polymerase active site, the tag polymer moiety becomes positioned in the α-HL wide-pore mutant nanopore conjugated nearby. Under the applied AC potential, the presence of the tag in the pore alters the ion flow through the nanopore relative than the O.C. current (i.e., current with no tag in the nanopore) resulting in a distinctive tag level current measured at the nanopore device electrodes. The distinctive tag current level measured as the different tag moieties enter the nanopore during Pol6 synthesis of a complementary DNA extension strand can be used to detect and identify the DNA template.

Nanopore Detection System:

The nanopore ion-flow measurements are performed using a nanopore array microchip comprising a CMOS microchip that has an array of 8,000,000 silver electrodes within shallow wells (chip fabricated by Genia Technologies, Santa Clara, CA, USA). Methods for fabricating and using such nanopore array microchips can also be found in U.S. Patent Application Publication Nos. 2013/0244340 A1, US 2013/0264207 A1, and US2014/0134616 A1 each of which is hereby incorporated by reference herein. Each well in the array is manufactured using a standard CMOS process with surface modifications that allow for constant contact with biological reagents and conductive salts. Each well can support a phospholipid bilayer membrane with a nanopore-polymerase conjugate embedded therein. The electrode at each well is individually addressable by computer interface. All reagents used are introduced into a simple flow cell above the array microchip using a computer-controlled syringe pump. The chip supports analog to digital conversion and reports electrical measurements from all electrodes independently at a rate of over 1000 points per second. Nanopore tag current measurements can be made asynchronously at each of 8 M addressable nanopore-containing membranes in the array at least once every millisecond (msec) and recorded on the interfaced computer.

Formation of Lipid Bilayer on Chip:

The phospholipid bilayer membrane on the chip is prepared using 1,2-diphytanoyl-sn-glycero-3-phosphocholine (Avanti Polar Lipids). The lipid powder is dissolved in decane at 15 mM and then painted in a layer across the wells on the chip. A thinning process then is initiated by pumping air through the cis side of the array wells, thus reducing multi-lamellar lipid membranes to a single bilayer.

Insertion of α-HL-Pol6 Conjugate in Membrane:

After the lipid bilayer forms on the wells of the array chip, 0.1 M of a 6:1 wide-pore mutant α-HL-Pol6 conjugate, 0.4 µM of the desired DNA template, all in a dilution buffer solution of 15 mM MgCl$_2$, 10 mM LiOAc, 5 mM TCEP, 20 mM HEPES, 300 mM potassium glutamate, pH 7.8, at 20° C. is added to the cis side of the chip. The nanopore-polymerase conjugate in the mixture either is electroporated or spontaneously inserts into the lipid bilayer. The non-polymerase modified α-HL subunits (i.e., the 6 subunits of the 6:1 heptamer) include the H144A mutation.

As disclosed in the results below, the wide-pore mutants disclosed in Table 6 above are used in forming the 6:1 heptamers.

The DNA template is a 5466 bp pUC19 dumbbell sequence having the nucleotide sequence shown in FIG. 2 (SEQ ID NO: 33).

Nanopore Ion Flow Measurements:

After insertion of the complex into the membrane, the solution on the cis side is replaced by an osmolarity buffer: 10 mM $MgCl_2$, 15 mM LiOAc, 5 mM TCEP, 0.5 mM EDTA, 20 mM HEPES, 300 mM potassium glutamate, pH 7.8, 20° C. 500 M of each of the set of the 4 different nucleotide substrates is added. The trans side buffer solution is: 10 mM $MgCl_2$, 15 mM LiOAc, 0.5 mM EDTA, 20 mM HEPES, 380 mM potassium glutamate, pH 7.5, 20° C. These buffer solutions are used as the electrolyte solutions for the nanopore ion flow measurements. A Pt/Ag/AgCl electrode setup is used and an AC current of a 210, 230, or 280 mV pk-to-pk waveform applied at 976 Hz. AC current has certain advantages for nanopore detection as it allows for the tag to be repeatedly directed into and then expelled from the nanopore thereby providing more opportunities to measure signals resulting from the ion flow through the nanopore. Also, the ion flow during the positive and negative AC current cycles counteract each other to reduce the net rate of ion depletion from the cis side, and possible detrimental effects on signals resulting from this depletion.

The tag current level signal representing the distinct altered ion-flow event resulting from each different polymer moiety tag is observed as the tagged nucleotide is captured by the α-HL-Pol6 nanopore-polymerase conjugates primed with the DNA template. Plots of these events are recorded over time and analyzed. Generally, events that last longer than 10 ms indicate productive tag capture coincident with polymerase incorporation of the correct base complementary to the template strand.

Results

As shown in Table 9 below, the tag current levels representing the distinct alteration of ion-flow events (relative to O.C.) induced by the different tagged nucleosides were observed as they were captured by the wide-pore mutant P-01, P-05, P-07, or P-08 nanopore polymerase conjugates ("α-HL-Pol6") primed with the DNA template.

TABLE 9

| Tagged Nucleotide | Tag SEQ ID NO: | Avg. Tag Current Level |
|---|---|---|
| dT6P-(Linker)-(SpC2)$_{17}$-(dA)$_7$-(SpC2)$_6$-C3 | 19 | 0.9[1] |
| dT6P-(Linker)-(SpC2)$_{15}$-(N3CEdT)$_7$-(SpC2)$_8$-C3 | 3 | 0.9[1] |
| dT6P-(Linker)-(SpC2)$_{17}$-(Etheno-dA)$_7$-(SpC2)$_6$-C3 | 13 | 0.89[1] |
| dT6P-(Linker)-(SpC2)$_{27}$-(N3CEdT)$_7$-(SpC2)$_1$-C3 | 7 | 0.85[1] |
| dT6P-(Linker)-(SpC2)$_{17}$-(Tmp)$_6$-(SpC2)$_7$-C3 | 12 | 0.85[1] |
| dT6P-(Linker)-(SpC2)$_{17}$-(Imp)$_7$-(SpC2)$_6$-C3 | 15 | 0.85[1] |
| dT6P-(Linker)-(SpC2)$_{17}$-(dCb)$_7$-(SpC2)$_6$-C3 | 16 | 0.85[1] |
| dT6P-(Linker)-(SpC2)$_{22}$-(dA)$_7$-(SpC2)$_1$-C3 | 20 | 0.84[1] |
| dT6P-(Linker)-(SpC2)$_{19}$-(N3CEdT)$_7$-(SpC2)$_4$-C3 | 5 | 0.84[1] |
| dT6P-(Linker)-(SpC2)$_{22}$-(Etheno-dA)$_7$-(SpC2)$_1$-C3 | 14 | 0.79[1] |
| dT6P-(Linker)-(SpC2)$_{23}$-(Tmp)$_6$-(SpC2)$_1$-C3 | 10 | 0.73[1] |
| dT6P-(Linker)-(SpC2)$_{22}$-(N3CEdT)$_7$-(SpC2)$_1$-C3 | 6 | 0.7[1] |
| dT6P-(Linker)-(SpC2)$_{17}$-(N3CEdT)$_{10}$-(SpC2)$_3$-C3 | 4 | 0.7[1] |
| dT6P-(Linker)-(SpC2)$_{22}$-(dCb)$_7$-(SpC2)$_1$-C3 | 17 | 0.62[1] |
| dT6P-(Linker)-(SpC2)$_{17}$-(Tmp-dT)$_5$-(SpC2)$_3$-C3 | 23 | 0.54[1] |

TABLE 9-continued

| Tagged Nucleotide | Tag SEQ ID NO: | Avg. Tag Current Level |
|---|---|---|
| dT6P-(Linker)-(SpC2)$_{20}$-(Tmp)$_6$-(SpC2)$_4$-C3 | 11 | 0.5[1] |
| dG6P-(Linker)-(SpC2)$_{14}$-(N3CEdT)$_{10}$-(SpC2)$_6$-C3 | 1 | 0.35[1] |
| dC6P-(Linker)-(SpC2)$_{21}$-(5MedC-PhEt)$_5$-(SpC2)$_4$-C3 | 21 | 0.75[1] |
| dA6P-(Linker)-(SpC2)$_{22}$-(dCb)$_7$-(SpC2)$_4$-C3 | 18 | 0.6[1] |
| dG6P-(Linker)-(SpC2)$_{20}$-(Tmp)$_6$-(SpC2)$_4$-C3 | 11 | 0.45[1] |
| dA6P-(Linker)-(SpC2)$_{17}$-(N3CEdT)$_{10}$-(SpC2)$_3$-C3 | 4 | 0.7[1,2,3] |
| dG6P-(Linker)-(SpC2)$_{15}$-(N3CEdT-5MedC-PhEt)$_5$-(SpC2)$_5$-C3 | 24 | 0.5[1,2,3] |
| dA6P-(Linker)-(SpC2)$_{14}$-(N3CEdT)$_{10}$-(SpC2)$_6$-C3 | 1 | 0.15[2] |
| dA6P-(Linker)-(SpC2)$_{14}$-(N3CEdT)$_{10}$-(SpC2)$_{11}$-C3 | 2 | 0.15[2] |
| dT6P-(Linker)-(SpC2)$_{14}$-(N3MedT)$_{10}$-(SpC2)$_6$-C3 | 8 | 0.35[2] |
| dT6P-(Linker)-(SpC2)$_{19}$-(N3CEdT)$_8$-(SpC2)$_3$-C3 | 25 | 0.67[2] |

[1]Using wide-pore mutant P-01; 210 mV AC current
[2]Using wide-pore mutant P-05; 230 mV AC current
[3]Using wide-pore mutant P-07 or P-08; 280 mV AC current The tagged nucleosides optimized for the wide-pore mutants exhibited a range detectable tag current level signals depending on the specific structural features. The tag current signals were distinctive and reproducible.

Sets of four differently tagged nucleoside compounds corresponding to the four different nucleoside-hexaphosphate polymerase substrates (dA6P, dC6P, dG6P, dT6P) were assembled and tested with a nanopore device comprising an array of wide-pore mutants (e.g., nanopores P-02, P-03, P-04, P-05, P-06, P-07, P-08). In order to provide a range of tag current levels, some of the sets included nucleotides with tags as disclosed in U.S. Ser. No. 15/684,726, filed Aug. 23, 2017, e.g., -T$_2$-(SpC2)$_{28}$-C3 (SEQ ID NO: 34), and -T$_2$-(dSp)$_{26}$-T$_2$-C3 (SEQ ID NO: 35). As shown in Table 10, the Sets 1, 2, 3, 4, 5, 6, and 7, each provide well-resolved average tag current levels that allow for accurate detection and identification using a nanopore device having an array of wide-pore mutants.

TABLE 10

| Tagged Nucleotide Set | Tag SEQ ID NO: | Avg. Tag Current Level |
|---|---|---|
| Set 1 | | |
| dC6P-(Linker)-T$_2$-(SpC2)$_{28}$-C3 | 34 | 1.15[1] |
| dA6P-(Linker)-T$_2$-(dSp)$_{26}$-T$_2$-C3 | 35 | 0.85[1] |
| dT6P-(Linker)-(SpC2)$_{19}$-(N3CEdT)$_7$-(SpC2)$_4$-C3 | 5 | 0.65[1] |
| dG6P-(Linker)-(SpC2)$_{14}$-(N3CEdT)$_{10}$-(SpC2)$_6$-C3 | 1 | 0.35[1] |
| Set 2 | | |
| dT6P-(Linker)-(SpC2)$_{22}$-(dA)$_7$-(SpC2)-C3 | 20 | 0.88[2] |
| dC6P-(Linker)-(SpC2)$_{24}$-(5MedC-PhEt)$_5$-(SpC2)$_4$-C3 | 21 | 0.76[2] |
| dA6P-(Linker)-(SpC2)$_{22}$-(dCb)$_7$-(SpC2)$_4$-C3 | 18 | 0.61[2] |
| dG6P-(Linker)-(SpC2)$_{20}$-(Tmp)$_6$-(SpC2)$_4$-C3 | 11 | 0.49[2] |
| Set 3 | | |
| dC6P-(Linker)-T$_2$-(SpC2)$_{28}$-C3 | 34 | 1.15[1,3] |
| dT6P-(Linker)-(SpC2)$_{19}$-(N3CEdT)$_7$-(SpC2)$_4$-C3 | 5 | 0.9[1,3] |
| dA6P-(Linker)-(SpC2)$_{17}$-(N3CEdT)$_{10}$-(SpC2)$_3$-C3 | 4 | 0.7[1,3] |
| dG6P-(Linker)-(SpC2)$_{15}$-(N3CEdT-5MedC-PhEt)$_5$-(SpC2)$_5$-C3 | 24 | 0.5[1,3] |
| Set 4 | | |
| dA6P-(Linker)-(SpC2)$_{14}$-(N3CEdT)$_{10}$-(SpC2)$_6$-C3 | 1 | 0.15[1] |
| dC6P-(Linker)-T$_2$-(SpC2)$_{28}$-C3 | 34 | 1.15[1] |
| dG6P-(Linker)-T$_2$-(dSp)$_{26}$-T$_2$-C3 | 35 | 0.80[1] |
| dT6P-(Linker)-(SpC2)$_{14}$-(N3MedT)$_{10}$-(SpC2)$_6$-C3 | 8 | 0.35[1] |

TABLE 10-continued

| Tagged Nucleotide Set | Tag SEQ ID NO: | Avg. Tag Current Level |
|---|---|---|
| Set 5 | | |
| dA6P-(Linker)-(SpC2)$_{14}$-(N3CEdT)$_{10}$-(SpC2)$_6$-C3 | 1 | 0.15[1] |
| dC6P-(Linker)-T$_2$-(SpC2)$_{28}$-C3 | 34 | 1.15[1] |
| dG6P-(Linker)-T$_2$-(dSp)$_{26}$-T$_2$-C3 | 35 | 0.80[1] |
| dT6P-(Linker)-(SpC2)$_{19}$-(N3CEdT)$_7$-(SpC2)$_4$-C3 | 5 | 0.60[1] |
| Set 6 | | |
| dA6P-(Linker)-(SpC2)$_{14}$-(N3CEdT)$_{10}$-(SpC2)$_6$-C3 | 1 | 0.15[1] |
| dC6P-(Linker)-T$_2$-(SpC2)$_{28}$-C3 | 34 | 1.15[1] |
| dG6P-(Linker)-T$_2$-(dSp)$_{26}$-T$_2$-C3 | 35 | 0.80[1] |
| dT6P-(Linker)-(SpC2)$_{19}$-(N3CEdT)$_8$-(SpC2)$_3$-C3 | 25 | 0.67[1] |
| Set 7 | | |
| dA6P-(Linker)-(SpC2)$_{14}$-(N3CEdT)$_{10}$-(SpC2)$_{11}$-C3 | 2 | 0.15[1] |
| dC6P-(Linker)-T$_2$-(SpC2)$_{28}$-C3 | 34 | 1.15[1] |
| dG6P-(Linker)-T$_2$-(dSp)$_{26}$-T$_2$-C3 | 35 | 0.80[1] |
| dT6P-(Linker)-(SpC2)$_{19}$-(N3CEdT)$_8$-(SpC2)$_3$-C3 | 25 | 0.67[1] |

[1]Using wide-port mutant P-05; 230 mV AC current;
[2]Using wide-pore mutant P-01; 210 mV AC current;
[3]Using wide-pore mutant P-07 or P-0219, 280 mV current Because the wide-pore mutants have lifetimes in a nanopore device that is approximately double that of non-wide-pore α-HL, the sets of wide-pore optimized tagged nucleotides allow for nucleic acid nanopore sequence reads that are approximately twice as long. For example, in a typical 45 minute nanopore sequencing experiment, the wide-pore optimized tagged nucleotides used with a wide-pore mutant array allows for a 1600 bp read-length rather than an 800 bp read length with the shorter lifetime non-wide-pore array.

The invention claimed is:

1. A compound comprising a nucleoside-5'-oligophosphate moiety covalently linked through the terminal phosphate group of the oligophosphate to the 5'-end of a negatively charged polymer moiety of structural formula (I)

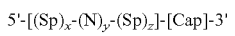   (I)

wherein,
x=12-24; y=5-15; z=1-8; x+y+z=27-35;
Sp is a monomer unit of formula (1a)

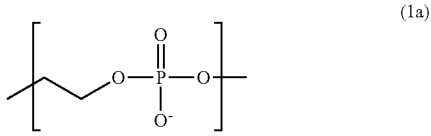   (1a)

N is a unit of formula (2a), (2b), or (2c)

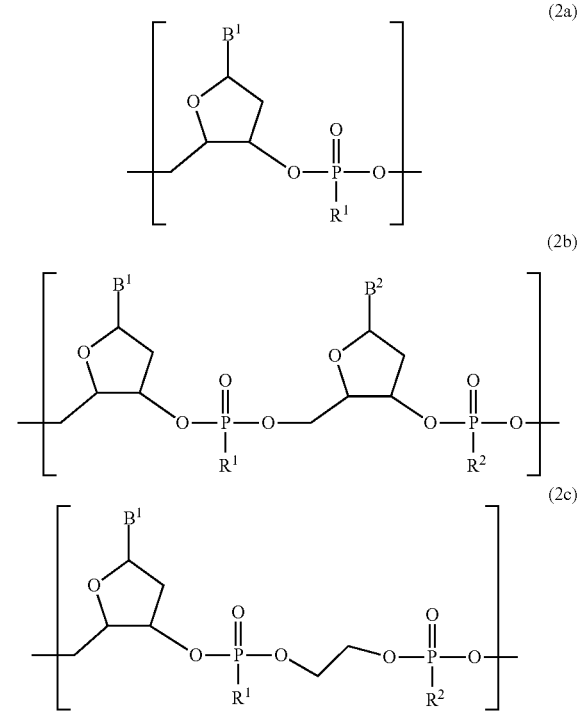

wherein,
B¹ and B² are independently selected from a natural nucleobase, a modified nucleobase comprising 3-N-cyanoethyl-dT amidite (N3CEdT), 3-N-methyl-dT amidite (N3MedT), 1,N6-etheno-dA amidite (etheno-dA), 5-methyl-dC amidite (5MedC), N4-phenylethyl-5-methyl-dC amidite (5MedC-PhEt), and N4-(O-Levulinyl-6-oxyhexyl)-5-methyl-dC amidite (dCb), and H; and R¹ and R² are independently selected from O⁻, CH₃, and H;
Cap is a 3'-end capping unit.

2. The compound of claim 1, wherein the compound is a substrate for a polymerase linked to a nanopore.

3. The compound of claim 1, wherein x+y+z=30.

4. The compound of claim 1, wherein x=14-22.

5. The compound of claim 1, wherein R¹ and/or R² are independently selected from O⁻ and CH₃.

6. The compound of claim 1, wherein B¹ and/or B² are independently selected from the group consisting of adenine, cytosine, guanine, thymine, uracil, hypoxanthine, N3CEdT, N3MedT, etheno-dA, 5MedC, 5MedC-PhEt, and dCb.

7. The compound of claim 1, wherein Cap is a 3'-propanol group.

8. The compound of claim 1, wherein N is a unit of formula (2a).

9. The compound of claim 1, wherein x=13-21, y=6-10, z=3-6, x+y+z=30, N is a unit of formula (2a), and Cap is a 3'-propanol group.

10. The compound of claim 9, wherein R¹ is O⁻ and B¹ is a modified nucleobase.

11. The compound of claim 9, wherein R¹ is CH₃ and B¹ is thymine or hypoxanthine.

12. The compound of claim 1, wherein the compound has a structural formula (II)

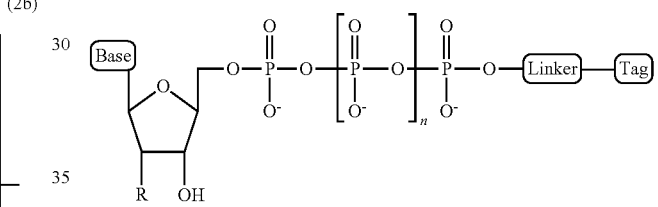   (II)

wherein,
Base is selected from adenine, cytosine, guanine, thymine, and uracil;
R is selected from H and OH;
n is from 1 to 4;
Linker is a linker comprising a covalently bonded chain of 2 to 100 atoms; and
Tag is the negatively charged polymer moiety of structural formula (I).

13. The compound of claim 12, wherein the linker comprises a chemical group selected from the group consisting of: ester, ether, thioether, amine, amide, imide, carbonate, carbamate, squarate, thiazole, thiazolidine, hydrazone, oxime, triazole, dihydropyridazine, phosphodiester, polyethylene glycol (PEG), Pictet-Spengler adduct, and any combination thereof.

14. The compound of claim 12, wherein R=H, n=4, and p=5.

15. The compound of claim 1, wherein the compound has a structural formula (IIa)

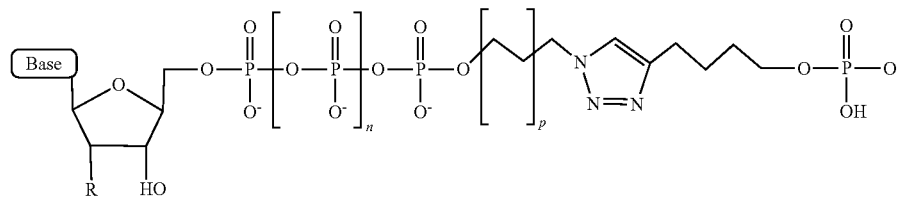   (IIa)

wherein,
  Base is selected from adenine, cytosine, guanine, thymine, and uracil;
  R is selected from H and OH;
  n is from 1 to 4;
  p is from 2 to 10; and
  Tag is the polymer moiety of structural formula (I).

16. The compound of claim 1, wherein the compound has a structural formula (IIb)

wherein,
  Base is selected from adenine, cytosine, guanine, thymine, and uracil;
  R is selected from H and OH;
  n is from 1 to 4;
  Linker is a linker comprising a covalently bonded chain of 2 to 100 atoms; and
  Tag is the polymer moiety of structural formula (I)

$$5'\text{-}[(Sp)_x\text{-}(N)_y\text{-}(Sp)_z]\text{-}[Cap]\text{-}3' \tag{I}$$

(IIb)

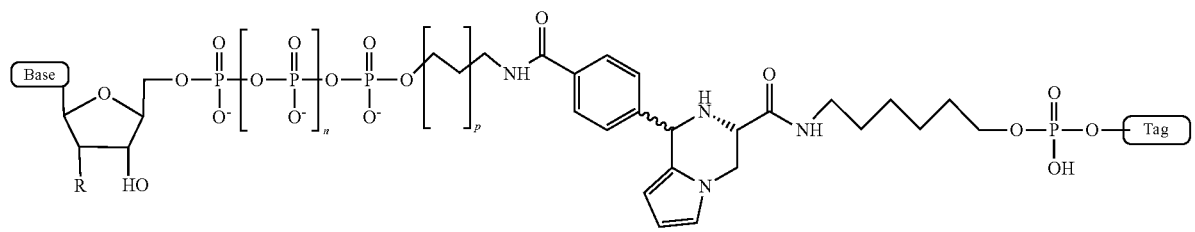

wherein,
  Base is selected from adenine, cytosine, guanine, thymine, and uracil;
  R is selected from H and OH;
  n is from 1 to 4;
  p is from 2 to 10; and
  Tag is the polymer moiety of structural formula (I).

17. The compound of claim 1, wherein the polymer moiety is capable of entering the cis opening of a nanopore and altering the flow of ions through the nanopore, wherein the nanopore has a constriction site that is approximately 13 angstroms in diameter and which is located approximately 65 angstroms from the cis opening of the pore.

18. The compound of claim 17, wherein the nanopore comprises a 6:1 ratio of α-HL subunits, wherein the subunits comprise amino acid substitutions E111N and M113A.

19. The compound of claim 18, wherein the subunits further comprise amino acid substitutions selected from D128K, K147N, and V149K.

20. The compound of claim 18, wherein the 6:1 ratio comprises 6× subunits comprising an amino acid substitution H144A.

21. The compound of claim 18, wherein the 6:1 ratio comprises a 1× subunit comprising a C-terminal fusion to a polymerase.

22. A composition comprising a set of compounds, each compound of the set comprising a different tag which results in a different altering of the flow of ions through a nanopore when the tag enters the nanopore, wherein at least one of the compounds of the set is a compound according to claim 1.

23. A composition comprising a set of compounds, each compound of the set comprising a different tag which results in a different altering of the flow of ions through a nanopore when the tag enters the nanopore, wherein at least one of the compounds has a structural formula (II)

wherein,
  x=12-24; y=5-15; z=1-8; x+y+z=27-35;
  Sp is a monomer unit of formula (1a)

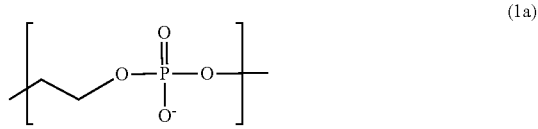

N is a unit of formula (2a), (2b), or (2c)

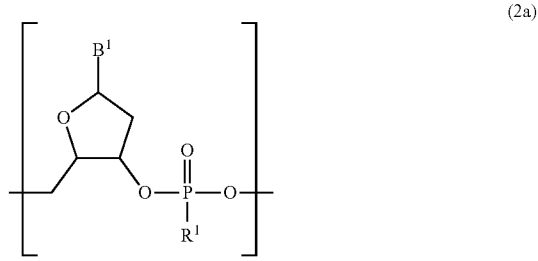

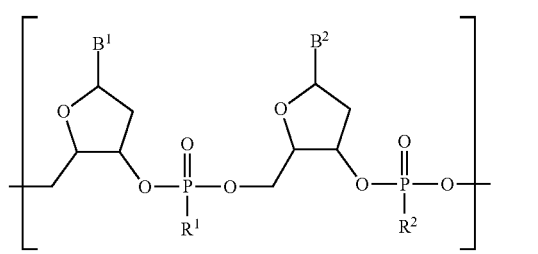

(II)

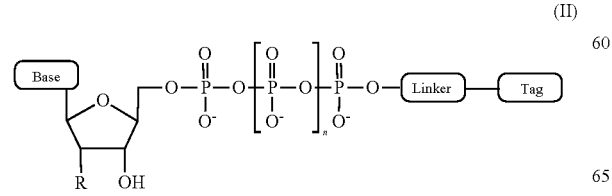

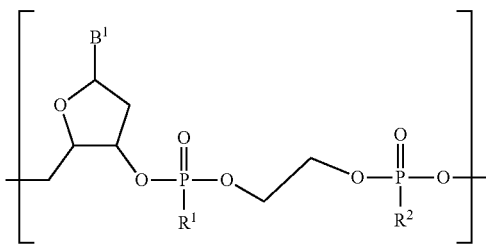

(2c)

wherein,
B¹ and B² are independently selected from a natural nucleobase, a modified nucleobase comprising 3-N-cyanoethyl-dT amidite (N3CEdT), 3-N-methyl-dT amidite (N3MedT), 1,N6-etheno-dA amidite (etheno-dA), 5-methyl-dC amidite (5MedC), N4-phenylethyl-5-methyl-dC amidite (5MedC-PhEt), and N4-(O-Levulinyl-6-oxy-hexyl)-5-methyl-dC amidite (dCb), and H; and R¹ and R² are independently selected from O⁻, CH₃, and H;

Cap is a 3'-end capping unit.

24. The composition of claim 23, wherein the at least one compound having a structural formula (II) comprises a polymer moiety of formula (I) selected from group consisting of:

---

-(SpC2)$_{14}$-(N3CEdT)$_{10}$-(SpC2)$_{6}$-C3
(SEQ ID NO: 1)
-(SpC2)$_{14}$-(N3CEdT)$_{10}$-(SpC2)$_{11}$-C3
(SEQ ID NO: 2)
-(SpC2)$_{15}$-(N3CEdT)$_{7}$-(SpC2)$_{8}$-C3
(SEQ ID NO: 3)
-(SpC2)$_{17}$-(N3CEdT)$_{10}$-(SpC2)$_{3}$-C3
(SEQ ID NO: 4)
-(SpC2)$_{19}$-(N3CEdT)$_{7}$-(SpC2)$_{4}$-C3
(SEQ ID NO: 5)
-(SpC2)$_{22}$-(N3CEdT)$_{7}$-(SpC2)$_{1}$-C3
(SEQ ID NO: 6)
-(SpC2)$_{27}$-(N3CEdT)$_{7}$-(SpC2)$_{1}$-C3
(SEQ ID NO: 7)
-(SpC2)$_{14}$-(N3MedT)$_{10}$-(SpC2)$_{6}$-C3
(SEQ ID NO: 8)
-(SpC2)$_{17}$-(dT)$_{10}$-(SpC2)$_{3}$-C3
(SEQ ID NO: 9)
-(SpC2)$_{23}$-(Tmp)$_{6}$-(SpC2)$_{1}$-C3
(SEQ ID NO: 10)
-(SpC2)$_{20}$-(Tmp)$_{6}$-(SpC2)$_{4}$-C3
(SEQ ID NO: 11)
-(SpC2)$_{17}$-(Tmp)$_{6}$-(SpC2)$_{7}$-C3
(SEQ ID NO: 12)
-(SpC2)$_{17}$-(Etheno-dA)$_{7}$-(SpC2)$_{6}$-C3
(SEQ ID NO: 13)
-(SpC2)$_{22}$-(Etheno-dA)$_{7}$-(SpC2)$_{1}$-C3
(SEQ ID NO: 14)
-(SpC2)$_{17}$-(Imp)$_{7}$-(SpC2)$_{6}$-C3
(SEQ ID NO: 15)
-(SpC2)$_{17}$-(dCb)$_{7}$-(SpC2)$_{6}$-C3
(SEQ ID NO: 16)
-(SpC2)$_{22}$-(dCb)$_{7}$-(SpC2)$_{1}$-C3
(SEQ ID NO: 17)
-(SpC2)$_{22}$-(dCb)$_{7}$-(SpC2)$_{4}$-C3
(SEQ ID NO: 18)
-(SpC2)$_{17}$-(dA)$_{7}$-(SpC2)$_{6}$-C3
(SEQ ID NO: 19)
-(SpC2)$_{22}$-(dA)$_{7}$-(SpC2)$_{1}$-C3
(SEQ ID NO: 20)
-(SpC2)$_{21}$-(5MedC-PhEt)$_{5}$-(SpC2)$_{4}$-C3
(SEQ ID NO: 21)
-(SpC2)$_{17}$-(SpC2-dT)$_{5}$-(SpC2)$_{3}$-C3
(SEQ ID NO: 22)
-(SpC2)$_{17}$-(Tmp-dT)$_{5}$-(SpC2)$_{3}$-C3
(SEQ ID NO: 23)
-(SpC2)$_{15}$-(N3CEdT-5MedC-PhEt)$_{5}$-(SpC2)$_{5}$-C3
(SEQ ID NO: 24)
-(SpC2)$_{19}$-(N3CEdT)$_{8}$-(SpC2)$_{3}$-C3
(SEQ ID NO: 25)

---

25. The composition of claim 23, wherein the set of compounds is selected from Set 1, Set 2, Set 3, Set 4, Set 5, Set 6, and Set 7:

---

Set 1 dC6P-(Linker)-T$_{2}$-(SpC2)$_{28}$-C3
dA6P-(Linker)-T$_{2}$-(dSp)$_{26}$-T$_{2}$-C3
dT6P-(Linker)-(SpC2)$_{19}$-(N3CEdT)$_{7}$-(SpC2)$_{4}$-C3
dG6P-(Linker)-(SpC2)$_{14}$-(N3CEdT)$_{10}$-(SpC2)$_{6}$-C3

Set 2 dT6P-(Linker)-(SpC2)$_{22}$-dA7-(SpC2)-C3
dC6P-(Linker)-(SpC2)$_{21}$-(5MedC-PhEt)$_{5}$-(SpC2)$_{4}$-C3
dA6P-(Linker)-(SpC2)$_{22}$-(dCb)$_{7}$-(SpC2)$_{4}$-C3
dG6P-(Linker)-(SpC2)$_{20}$-(Tmp)$_{6}$-(SpC2)$_{4}$-C3

Set 3 dC6P-(Linker)-T$_{2}$-(SpC2)$_{28}$-C3
dT6P-(Linker)-(SpC2)$_{19}$-(N3CEdT)$_{7}$-(SpC2)$_{4}$-C3
dA6P-(Linker)-(SpC2)$_{17}$-(N3CEdT)$_{10}$-(SpC2)$_{3}$-C3
dG6P-(Linker)-(SpC2)$_{15}$-(N3CEdT-5MedC-PhEt)$_{5}$-(SpC2)$_{5}$-C3

Set 4 dA6P-(Linker)-(SpC2)$_{14}$-(N3CEdT)$_{10}$-(SpC2)$_{6}$-C3
dC6P-(Linker)-T$_{2}$-(SpC2)$_{28}$-C3
dG6P-(Linker)-T$_{2}$-(dSp)$_{26}$-T$_{2}$-C3
dT6P-(Linker)-(SpC2)$_{14}$-(N3MedT)$_{10}$-(SpC2)$_{6}$-C3

Set 5 dA6P-(Linker)-(SpC2)$_{14}$-(N3CEdT)$_{10}$-(SpC2)$_{6}$-C3
dC6P-(Linker)-T$_{2}$-(SpC2)$_{28}$-C3
dG6P-(Linker)-T$_{2}$-(dSp)$_{26}$-T$_{2}$-C3
dT6P-(Linker)-(SpC2)$_{19}$-(N3CEdT)$_{7}$-(SpC2)$_{4}$-C3

Set 6 dA6P-(Linker)-(SpC2)$_{14}$-(N3CEdT)$_{10}$-(SpC2)$_{6}$-C3
dC6P-(Linker)-T$_{2}$-(SpC2)$_{28}$-C3
dG6P-(Linker)-T$_{2}$-(dSp)$_{26}$-T$_{2}$-C3
dT6P-(Linker)-(SpC2)$_{19}$-(N3CEdT)$_{8}$-(SpC2)$_{3}$-C3

Set 7 dA6P-(Linker)-(SpC2)$_{14}$-(N3CEdT)$_{10}$-(SpC2)$_{11}$-C3
dC6P-(Linker)-T$_{2}$-(SpC2)$_{28}$-C3
dG6P-(Linker)-T$_{2}$-(dSp)$_{26}$-T$_{2}$-C3
dT6P-(Linker)-(SpC2)$_{19}$-(N3CEdT)$_{8}$-(SpC2)$_{3}$-C3

---

26. A method for determining the sequence of a nucleic acid comprising:

(a) providing a nanopore sequencing composition comprising: a membrane, an electrode on the cis side and the trans side of the membrane, a wide-pore mutant a-HL nanopore with its pore extending through the membrane, an electrolyte solution comprising ions in contact with both electrodes, an active polymerase situated adjacent to the nanopore, and a primer strand complexed with the polymerase;

(b) contacting the nanopore sequencing composition with
   (i) a strand of the nucleic acid; and
   (ii) a set of compounds each comprising a different nucleoside-5'-oligophosphate moiety covalently linked to a tag, wherein each member of the set of compounds has a different tag which results in a different altering of the flow of ions through a nanopore when the tag enters the nanopore, wherein at least one of the compounds of the set is a compound according to claim 1; and
(c) detecting the different altering of the flows of ions resulting from the entry of the different tags in the nanopore over time and correlating to each of the different compounds incorporated by the polymerase which are complementary to the nucleic acid sequence, and thereby determining the nucleic acid sequence.

* * * * *